United States Patent
Freeman et al.

(10) Patent No.: US 10,702,166 B1
(45) Date of Patent: *Jul. 7, 2020

(54) DEVICES AND METHODS FOR RESPIRATORY VARIATION MONITORING BY MEASUREMENT OF RESPIRATORY VOLUMES, MOTION AND VARIABILITY

(71) Applicant: Respiratory Motion, Inc., Lexington, MA (US)

(72) Inventors: Jenny E. Freeman, WEston, MA (US); Michael Lalli, Haverhill, MA (US); Alexander Panasyuk, Lexington, MA (US); Malcolm G. Bock, Medfield, MA (US); Jordan Brayanov, Medford, MA (US)

(73) Assignee: Respiratory Motion, Inc., Watertown, MA (US)

(*) Notice: Subject to any disclaimer, the term of this patent is extended or adjusted under 35 U.S.C. 154(b) by 1 day.

This patent is subject to a terminal disclaimer.

(21) Appl. No.: 14/246,862

(22) Filed: Apr. 7, 2014

Related U.S. Application Data

(63) Continuation-in-part of application No. 13/554,346, filed on Jul. 20, 2012, and a continuation-in-part of
(Continued)

(51) Int. Cl.
*A61B 5/0205* (2006.01)
*A61B 5/0402* (2006.01)
(Continued)

(52) U.S. Cl.
CPC .......... *A61B 5/0205* (2013.01); *A61B 5/0402* (2013.01); *A61B 5/1128* (2013.01);
(Continued)

(58) Field of Classification Search
USPC ................................. 600/529, 484, 538, 534
See application file for complete search history.

(56) References Cited

U.S. PATENT DOCUMENTS

| 3,433,217 A | 3/1969 | Rieke et al. |
| 3,690,143 A | 9/1972 | Day et al. |

(Continued)

FOREIGN PATENT DOCUMENTS

| CN | 1034665 | 8/1989 |
| CN | 101496767 | 8/2010 |

(Continued)

OTHER PUBLICATIONS

Aroom, Kevin R., et al. "Bioimpedance analysis: a guide to simple design and implementation." Journal of Surgical Research 153.1 (2009): 23-30 (Aroom).*

(Continued)

*Primary Examiner* — Christian Jang
*Assistant Examiner* — Mitchell E Alter
(74) *Attorney, Agent, or Firm* — Remenick PLLC

(57) ABSTRACT

This invention is directed to devices and methods for assessing a patient. The devices have at least one impedance measuring element functionally connected to a programmable element, programmed to analyze an impedance measurement, and to provide an assessment of at least one respiratory parameter of the patient. Preferably the device includes electronics which aid in calibration, signal acquisition, conditioning, and filtering.

25 Claims, 26 Drawing Sheets

Related U.S. Application Data application No. 13/210,360, filed on Aug. 15, 2011, now Pat. No. 10,271,739.

(60) Provisional application No. 61/809,025, filed on Apr. 5, 2013, provisional application No. 61/509,952, filed on Jul. 20, 2011, provisional application No. 61/480,105, filed on Apr. 28, 2011, provisional application No. 61/449,811, filed on Mar. 7, 2011, provisional application No. 61/373,548, filed on Aug. 13, 2010.

(51) Int. Cl.
| | | |
|---|---|---|
| *A61B 5/00* | (2006.01) | |
| *A61B 5/113* | (2006.01) | |
| *A61B 5/11* | (2006.01) | |
| *A61M 16/00* | (2006.01) | |
| *A61M 16/04* | (2006.01) | |
| *A61B 5/1455* | (2006.01) | |
| *A61B 5/087* | (2006.01) | |
| *A61B 5/053* | (2006.01) | |
| *A61B 5/08* | (2006.01) | |
| *A61B 5/083* | (2006.01) | |
| *A61B 5/091* | (2006.01) | |
| *A61B 5/085* | (2006.01) | |
| *A61B 5/024* | (2006.01) | |

(52) U.S. Cl.
CPC ........ *A61B 5/1135* (2013.01); *A61B 5/14551* (2013.01); *A61B 5/4821* (2013.01); *A61B 5/4839* (2013.01); *A61B 5/4848* (2013.01); *A61B 5/686* (2013.01); *A61B 5/7203* (2013.01); *A61B 5/7275* (2013.01); *A61B 5/7278* (2013.01); *A61M 16/0003* (2014.02); *A61M 16/0051* (2013.01); *A61M 16/0057* (2013.01); *A61M 16/04* (2013.01); *A61B 5/02416* (2013.01); *A61B 5/053* (2013.01); *A61B 5/085* (2013.01); *A61B 5/0809* (2013.01); *A61B 5/0816* (2013.01); *A61B 5/0836* (2013.01); *A61B 5/0871* (2013.01); *A61B 5/091* (2013.01)

(56) References Cited

U.S. PATENT DOCUMENTS

| | | | |
|---|---|---|---|
| 3,742,936 | A | 7/1973 | Blanie et al. |
| 4,036,217 | A | 7/1977 | Ito et al. |
| 5,058,583 | A | 10/1991 | Geddes et al. |
| 5,469,859 | A * | 11/1995 | Tsoglin .............. A61B 5/0535 600/536 |
| 5,735,284 | A | 4/1998 | Tsoglin et al. |
| 6,168,568 | B1 | 1/2001 | Gavriely |
| 6,173,198 | B1 | 1/2001 | Schulze et al. |
| 6,286,806 | B1 | 9/2001 | Corcoran |
| 6,366,803 | B1 | 4/2002 | Fee |
| 6,402,969 | B1 | 6/2002 | Rodgers et al. |
| 6,809,462 | B2 | 10/2004 | Pelrine et al. |
| 6,976,963 | B2 | 12/2005 | Clift |
| 7,196,317 | B1 | 3/2007 | Meissner, II et al. |
| 7,361,146 | B1 * | 4/2008 | Bharmi .............. A61B 5/02405 600/481 |
| 7,530,956 | B2 | 5/2009 | Lewicke et al. |
| 7,668,579 | B2 * | 2/2010 | Lynn ................... A61B 5/412 600/323 |
| 8,096,962 | B2 | 1/2012 | Palazzolo et al. |
| 8,306,611 | B2 | 11/2012 | Granov et al. |
| 2002/0032383 | A1 | 3/2002 | Weil et al. |
| 2004/0071337 | A1 | 4/2004 | Jeung et al. |
| 2004/0123667 | A1 | 7/2004 | McGrath |
| 2005/0033198 | A1 | 2/2005 | Kehyayan et al. |
| 2005/0090753 | A1 | 4/2005 | Goor et al. |
| 2005/0107719 | A1 | 5/2005 | Arad (Abbound) |
| 2005/0113702 | A1 | 5/2005 | Salla et al. |
| 2006/0058600 | A1 | 3/2006 | Eichler |
| 2006/0241506 | A1 | 10/2006 | Melker et al. |
| 2006/0241513 | A1 * | 10/2006 | Hatlestad ............ A61B 5/0809 600/547 |
| 2007/0010764 | A1 | 1/2007 | Palazzolo et al. |
| 2007/0152678 | A1 * | 7/2007 | Matoba ................ H01J 37/321 324/601 |
| 2007/0276300 | A1 | 11/2007 | Olson et al. |
| 2008/0312565 | A1 | 12/2008 | Celik-Butler et al. |
| 2009/0062672 | A1 | 3/2009 | Sly et al. |
| 2009/0149748 | A1 | 6/2009 | Lenhardt et al. |
| 2009/0227849 | A1 | 9/2009 | Goor et al. |
| 2009/0264789 | A1 * | 10/2009 | Molnar .............. A61N 1/36135 600/544 |
| 2009/0326253 | A1 | 12/2009 | Iding et al. |
| 2009/0326353 | A1 | 12/2009 | Watson et al. |
| 2010/0049071 | A1 * | 2/2010 | Goor ................. A61B 5/02028 600/526 |
| 2010/0152600 | A1 | 6/2010 | Droitcour et al. |
| 2010/0204585 | A1 * | 8/2010 | Zhang ................. A61B 5/0452 600/483 |
| 2010/0228166 | A1 | 9/2010 | Centen |
| 2010/0241181 | A1 | 9/2010 | Savage et al. |
| 2010/0324437 | A1 * | 12/2010 | Freeman ................ A61B 5/085 600/529 |
| 2011/0077497 | A1 | 3/2011 | Oster et al. |
| 2011/0218450 | A1 * | 9/2011 | Haefner ................ A61B 5/085 600/533 |
| 2011/0243285 | A1 * | 10/2011 | Kenington ......... H04B 17/0085 375/349 |
| 2011/0245712 | A1 | 10/2011 | Patterson et al. |
| 2011/0306850 | A1 | 12/2011 | Hatlestad et al. |
| 2012/0041279 | A1 * | 2/2012 | Freeman .............. A61B 5/0205 600/301 |
| 2012/0165883 | A1 | 6/2012 | Kalgren et al. |
| 2013/0187941 | A1 | 7/2013 | Noon |
| 2013/0296823 | A1 | 11/2013 | Melker et al. |
| 2014/0073895 | A1 | 3/2014 | Freeman et al. |

FOREIGN PATENT DOCUMENTS

| | | |
|---|---|---|
| EP | 1302217 | 4/2003 |
| EP | 2008581 | 12/2008 |
| EP | 2018825 | 1/2009 |
| JP | 200070370 | 3/2000 |
| JP | 2007203041 | 8/2007 |
| JP | 2009240752 | 10/2009 |
| WO | WO0033733 | 6/2000 |
| WO | WO 2006/006871 | 1/2006 |
| WO | WO2007064682 | 6/2007 |
| WO | WO2007147505 | 12/2007 |
| WO | WO2008130549 | 10/2008 |
| WO | WO2009035965 | 3/2009 |
| WO | WO2009036312 | 3/2009 |
| WO | WO2010059049 | 5/2010 |

OTHER PUBLICATIONS

U.S. App. No. 12/677,216, Freeman et al.
U.S. App. No. 13/210,360, Freeman et al.
U.S. App. No. 13/554,346, Freeman et al.
U.S. App. No. 14/021,939, Freeman et al.
Zulkarneev R Kh. Et al., A Hardware-Software System for Volumetric Calibration of Impedance Pneumograms, Biomedical Engineering, vol. 35, No. 1, 2001, pp. 48-51.
Pajic, et al, Model-driven safety analysis of closed-loop medical systems, IEEE Trans Industr Inform. vol. 10, pp. 1-35, p. 4, para. 1-2, Oct. 28, 2013.
Aroom, Kevin R. Et al. "Bioimpedance Analysis: A Guide to Simple Design and Implementation," Journal of Surgical Research 153, 23-30 (2009), Dec. 17, 2007.

\* cited by examiner

DEVICES AND METHODS FOR RESPIRATORY VARIATION MONITORING BY MEASUREMENT OF RESPIRATORY VOLUMES, MOTION AND VARIABILITY

REFERENCE TO RELATED APPLICATIONS

The present application is a continuation in part of U.S. application Ser. No. 13/210,360, filed Aug. 15, 2011, and entitled "Devices And Methods For Respiratory Variation Monitoring by Measurement of Respiratory Volumes, Motion and Variability," which claims priority to Provisional U.S. Application Nos. 61/373,548, filed Aug. 13, 2010 and entitled "Devices and Methods for Respiratory Variation Monitoring by Measurement of Respiratory Volumes, Motion and Variability," 61/449,811, filed Mar. 7, 2011 and entitled "Respiratory Variation Monitoring Instrument," 61/480,105 filed Apr. 28, 2011 and entitled "Systems and Methods of Respiratory Monitoring," and 61/509,952, filed Jul. 20, 2011 and entitled "Use of Impedance Measurements for Measuring Intrathoracic Volume in Emergency Cardiovascular Care," the present application is also a continuation in part of U.S. application Ser. No. 13/554,346, filed Jul. 20, 2012, and entitled "Impedance Measuring Device and Methods for Emergency Cardiovascular Care," which claims priority to Provisional U.S. Application No. 61/509,952, filed Jul. 20, 2011 and entitled "Use of Impedance Measurements for Measuring Intrathoracic Volume in Emergency Cardiovascular Care," the present application also claims priority to Provisional U.S. Application No. 61/809,025, filed Apr. 5, 2013, and entitled "Devices And Methods For Respiratory Variation Monitoring by Measurement of Respiratory Volumes, Motion and Variability," all of which are incorporated in their entirety.

BACKGROUND OF THE INVENTION

1. Field of the Invention

This invention is directed to methods and devices for collecting and analyzing data to assess the respiratory status and health of human and/or animal subjects. The invention incorporates and builds off of the fields of impedance plethysmography, impedance pneumography, acoustics and data analysis of the electrical impedance signal.

2. Description of the Background

Physiological Monitoring—History and Evolution

Patient monitoring is essential because it provides warning to patient deterioration and allows for the opportunity of early intervention, greatly improving patient outcomes. For example, modern monitoring devices can detect abnormal heart rhythms, blood oxygen saturation, and body temperature, which can alert clinicians of a deterioration that would otherwise go unnoticed.

The earliest records of patient monitoring reveal that ancient Egyptians were aware of the correlation between peripheral pulse and the heart beat as early as 1550 BC. Three millennia passed before the next significant advancement in monitoring was made, with Galileo using a pendulum to measure pulse rate. In 1887, Waller determined that he could passively record electrical activity across the chest by using electrodes and correlated the signal to activity from the heart. Waller's discovery paved the way for the use of electrical signals as a method to measure physiological signals. However, it would still take time before scientists recognized the advantages of monitoring a physiological signal in a clinical environment.

In 1925, MacKenzie emphasized the importance of continuous recording and monitoring of physiological signals such as the pulse rate and blood pressure. He specifically stressed that the graphical representation of these signals is important in the assessment of a patient's condition. In the 1960s, with the advent of computers, patient monitors improved with the addition of a real-time graphical display of multiple vital signs being recorded simultaneously. Alarms were also incorporated into monitors and were triggered when signals, such as a pulse rate or blood pressure, reached a certain threshold.

The first patient monitors were used on patients during surgery. As patient outcomes were shown to improve, monitoring of vital signs spread to other areas of the hospital such as the intensive care unit and the emergency department. For instance, pulse oximetry was first widely used in operating rooms as a method to continuously measure a patient's oxygenation non-invasively. Pulse oximetry quickly became the standard of care for the administration of general anesthetic and subsequently spread to other parts of the hospital, including the recovery room and intensive care units.

The Growing Need for Improved Patient Monitoring

The number of critically ill patients presenting to the emergency department is increasing at a great rate, and these patients require close monitoring. It has been estimated that between 1-8% of patients in the emergency department require a critical care procedure to be performed, such as a cardiovascular procedure or a thoracic and respiratory procedure (mechanical ventilation, catheter insertion, arterial cannulation).

Physiological scores, such as the Mortality Probability Model (MPM), the Acute Physiology and Chronic Health Education (APACHE), the Simplified Acute Physiological Score (SAPS) and the Therapeutic Intervention Scoring System (TISS) have shown significant improvements in patient outcomes. Monitoring sick patients by using physiological scores and vital signs in their early stages of illness, even prior to organ failure or shock, improves outcomes. Close monitoring of patients allows for recognition of patient degeneration and the administration of the appropriate therapy.

However, current scoring methods do not accurately predict patient outcomes in approximately 15% of ICU patients, and it may be worse for patients in a respiratory intensive care unit, which provide care in hospitals with large number of patients with acute respiratory failure. Furthermore, differences in currently monitored vital signs such as blood oxygenation occur late in the progression of respiratory or circulatory compromise. Often the earliest sign of patient degradation is a change in a patient's breathing effort or respiratory pattern.

Respiratory rate is recognized as a vital indicator of patient health and is used to assess patient status. However, respiratory rate alone fails to indicate important physiological changes, such as changes in respiratory volumes. Metrics derived from continuous volume measurements have been shown to have great potential for determining patient status in a wide range of clinical applications. However, there are currently no adequate systems that can accurately and conveniently determine respiratory volumes, which motivates the need for a non-invasive respiratory monitor that can trace changes in breath volume.

Shortcomings of Current Methods

Currently, a patient's respiratory status is monitored with methods such as spirometry and end tidal $CO_2$ measurements. These methods are often inconvenient to use and inaccurate. While end tidal $CO_2$ monitoring is useful during anesthesia and in the evaluation of intubated patients in a variety of environments, it is inaccurate for non-ventilated patients. The spirometer and pneumotachometer are limited in their measurements are highly dependent on patient effort and proper coaching by the clinician. Effective training and quality assurance are a necessity for successful spirometry. However, these two prerequisites are not necessarily enforced in clinical practice like they are in research studies and pulmonary function labs. Therefore quality assurance is essential to prevent misleading results.

Spirometry is the most commonly performed pulmonary function test. The spirometer and pneumotachometer can give a direct measurement of respiratory volume. It involves assessing a patient's breathing patterns by measuring the volume or the flow of air as it enters and leaves the patient's body. Spirometry procedures and maneuvers are standardized by the American Thoracic Society (ATS) and the European Respiratory Society (ERS). Spirometry can provide important metrics for evaluating respiratory health and diagnosing respiratory pathologies. The major drawback of mainstream spirometers is that they require the patient to breathe through a tube so that the volume and/or flow rate of his breath can be measured. Breathing through the apparatus introduces resistance to the flow of breath and changes the patient's breathing pattern. Thus it is impossible to use these devices to accurately measure a patient's normal breathing. Breathing through the apparatus requires a conscious, compliant patient. Also, in order to record the metrics suggested by the ATS and ERS, patients must undergo taxing breathing maneuvers, which excludes most elderly, neonatal, and COPD patients from being able to undergo such an examination. The outcomes of the procedures are also highly variable dependent on patient effort and coaching, and operator skill and experience. The ATS also recommends extensive training for healthcare professionals who practice spirometry. Also, many physicians do not have the skills needed to accurately interpret the data gained from pulmonary function tests. According to the American Thoracic Society, the largest source of intrasubject variability is improper performance of test. Therefore much of the intrapatient and interpatient variability in pulmonary function testing is produced by human error. Impedance-based respiratory monitoring fills an important void because current spirometry measurements are unable to provide continuous measurements because of the requirement for patient cooperation and breathing through a tube. Therefore there is a need for a device that provides near-real-time information over extended periods of time (vs. spirometry tests which last a minute or less) in non-intubated patients that can show changes in respiration related to a provocative test or therapeutic intervention.

In order to acquire acceptable spirometry measurements, as dictated by ATS standards, healthcare professionals must have extensive training and take refresher courses. A group showed that the amount of acceptable spirometry measurements was significantly greater for those who did a training workshop (41% vs. 17%). Even with acceptable spirometry measurements, the interpretations of the data by primary physicians were deemed as incorrect 50% of the time by pulmonologists. However, it was noted that aid from computer algorithms showed improvement in interpreting spirograms when adequate spirometry measurements were collected.

Rigorous training is needed for primary care clinics to acquire acceptable spirometry measurements and make accurate interpretations. However, resources to train a large number of people and enforce satisfactory quality assurance are unreasonable and inefficient. Even in a dedicated research setting, technician performance falls over time.

In addition to human error due to the patient and healthcare provider, spirometry contains systematic errors that ruin breathing variability measurements. Useful measurements of breath by breath patterns and variability have been shown to be compounded by airway attachments such as a facemask or mouthpiece. Also, the discomfort and inconvenience involved during measurement with these devices prevents them from being used for routine measurements or as long-term monitors. Other less intrusive techniques such as thermistors or strain gauges have been used to predict changes in volume, but these methods provide poor information on respiratory volume. Respiratory belts have also shown promise in measuring respiration volume, but groups have shown that they are less accurate and have a greater variability than measurements from impedance pneumography. Therefore, a system that can measure volume for long periods of time with minimal patient and clinician interaction is needed.

Pulmonary Function Testing and Preoperative, Postoperative Care

Preoperative care is centered on identifying what patient characteristics may put the patient at risk during an operation and minimizing those risks. Medical history, smoking history, age, and other parameters dictate the steps taken in preoperative care. Specifically, elderly patients and patients with pulmonary diseases may be at risk for respiratory complications when placed under a ventilator for surgery. In order to clear these patients for surgery, pulmonary function tests such as spirometry are performed which give the more information to determine whether the patient can utilize the ventilator. Chest x-rays may also be taken. However, these tests cannot be replicated mid-surgery, or in narcotized patients or those who cannot or will not cooperate. Testing may be uncomfortable in a postoperative setting and disruptive to patient recovery.

End Tidal $CO_2$ and Patient Monitoring

End tidal $CO_2$ is another useful metric for determining pulmonary state of a patient. The value is presented as a percentage or partial pressure and is measured continuously using a capnograph monitor, which may be coupled with other patient monitoring devices. These instruments produce a capnogram, which represents a waveform of $CO_2$ concentration. Capnography compares carbon dioxide concentrations within expired air and arterial blood. The capnogram is then analyzed to diagnose problems with respiration such as hyperventilation and hypoventilation. Trends in end tidal $CO_2$ are particularly useful for evaluating ventilator performance and identifying drug activity, technical problems with intubation, and airway obstruction. The American Society of Anesthesiologists (ASA) mandates that end-tidal $CO_2$ be monitored any time an endotracheal tube or laryngeal mask is used, and is also highly encouraged for any treatment that involves general anesthesia. Capnography has also been proven to be more useful than pulse oximetry for monitoring of patient ventilation. Unfortunately, it is generally inaccurate and difficult to implement in the non-ventilated patient, and other complementary respiratory monitoring methods would have great utility.

Echocardiograms

Fenichel et al. determined that respiratory motion can cause interference with echocardiograms if it is not controlled for. Respiratory motion can block anterior echoes through pulmonary expansion and it chances the angle of incidence of the transducer ray relative to the heart. These effects on the echocardiography signal can decrease the accuracy of measurements recorded or inferred from echocardiograms. Combining echocardiography with accurate measurement of the respiratory cycle can allow an imaging device to compensate for respiratory motion.

Impedance Pneumography

Impedance pneumography is a simple method that can yield respiratory volume tracings without impeding airflow, does not require contact with the airstream, and does not restrict body movements. Furthermore, it may be able to make measurements that reflect functional residual capacity of the lungs.

While attempting to measure cardiac activity, Atzler and Lehmann noted transthoracic electrical impedance changed with respiration. They regarded the respiratory impedance changes as artifacts and asked the patients to stop breathing while measurements were made. In 1940, while also studying cardiac impedance, Nyboer noticed the same respiratory impedance artifact in his measurement. He confirmed the origin of the artifact by being the first person to relate changes in transthoracic impedance to changes in volume using a spirometer by simultaneously recording both. Goldensohn and Zablow took impedance pneumography a step further by being the first investigators to quantitatively relate respired volume and transthoracic impedance. They reported difficulty in separating the cardiac signal artifacts and also noted artifacts during body movements. However, after comparing the impedance changes and respired volume changes by a least squares regression, they importantly determined that the two are linearly related. Other groups have confirmed the linear relationship between transthoracic impedance changes and respiratory breaths and have found that approximately 90% of the spirometric signal can be explained by the thoracic impedance signal. While the relationship has been shown to be linear, many groups found the calibration constants for intrapatient and interpatient to be highly variable between trials. These differences in calibration constants can be attributed to a variety of physiological and electrode characteristics, which must be taken into account.

Transthoracic Impedance Theory

Electrical impedance is a complex quantity defined as the sum of the resistance (R), the real component, and the reactance (X), the imaginary component ($Z=R+jX=|Z|e^{j\Theta}$). It is used as the measurement of opposition to an alternating current. Mathematically, impedance is measured by the following equation, which is analogous to Ohm's law:

$$Z=V/I \quad (1)$$

Where voltage=V, current=I, and impedance=Z. An object that conducts electricity with unknown impedance can be determined from a simple circuit. Applying a known alternating current across the object while simultaneously measuring the voltage across it and using equation (1) yields the impedance. The thorax represents a volume conductor, and because of that, the laws governing ionic conductors can be applied. In addition, the movement of organs and the enlargement of the thoracic cage during breathing create a change in conductivity, which can be measured. Impedance across the thorax can be measured by introducing a known current and measuring the change in voltage across the thorax with electrodes.

Origins of the Transthoracic Impedance Signal

The tissue layers that makeup the thorax and the abdomen, all influence the measurement of transthoracic impedance. Each tissue has a different conductivity that influences the direction of current flow between electrodes. Beginning with the outermost layer, the surface of the body is covered by skin, which presents a high resistivity but is only about 1 mm thick. Under the skin is a layer of fat, which also has a high resistivity. However, the thickness of this layer is highly variable and depends on body location and the body type of the subject. Moving posterior to anterior, below the layer of skin and fat are the postural muscles, which are anisotropic. They have a low resistivity in the longitudinal direction but a high resistivity in all other directions, which leads to a tendency to conduct current in a direction that is parallel to the skin. Below the muscle are the ribs, which, as bone, are highly insulating. Therefore, current through the thorax can only flow between bones. Once current reaches the lungs, it is hypothesized that current travels through the blood, which has one of the lowest resistances of any body tissue. Aeration of the lungs changes the size of the lung and the pathway of current flow, and manifests itself as a change in resistance or impedance that can be measured.

Due to the anisotropic properties of the tissues, radial current flow through the chest is much less than would be expected. Much of the current goes around the chest rather than through it. As a result, impedance changes come from changes in thoracic circumference, changes in lung size, and movement of the diaphragm-liver mass. Measurements at lower thoracic levels are attributed to movement of the diaphragm and liver, and at higher thoracic levels they are attributed to aeration and expansion of the lungs. Therefore, the impedance signal is the sum of the change from the expansion and aeration of the lungs and the movement of the diaphragm-liver mass. Both the abdominal and thoracic components are needed in order to observe a normal respiratory signal. In addition, the different origins of impedance changes in the upper and lower thorax could explain why greater linearity is observed at higher thoracic levels.

Influences of Electrode Placement

Transthoracic impedance is measured with electrodes attached to the patient's skin. Geddes et al. determined that the electrode stimulation frequency should not be below 20 kHz because of physiological tissue considerations. It is a matter of safety and eliminating interference from bioelectric events. In addition, impedance measurements of a subject were found to differ depending on subject position, including sitting, supine, and standing. It was shown that for a given change in volume, laying supine yielded the greatest signal amplitude and lowest signal to noise during respiration.

Another potential signal artifact comes from subject movements, which may move electrodes and disturb calibrations. Furthermore, electrode movements may be more prevalent in obese and elderly patients, which may require repetitive lead recalibration during periods of long-term monitoring. Because of the calibration variability between trials, some have suggested that calibration should be performed for each individual for a given subject posture and electrode placement. However, a group was able to show that careful intrapatient electrode placement can reduce impedance differences between measurements to around 1%.

Despite having the same electrode placements, calibration constants and signal amplitudes for individuals of different sizes showed variability. It was determined that the change in impedance for a given change in volume is the largest for thin-chested people and smaller for people who are more amply sized. These observed differences may be due to the greater amount of resistive tissue, such as adipose tissue and muscle, between the electrodes and lungs in larger subjects, yielding an overall smaller percent change in impedance for a given change in volume for larger subjects. On the other hand, it is noticeable that in children the cardiac component of the impedance trace is greater than in adults. This may be due to greater fat deposition around the heart in adults than in children, which serves to shield the heart from being incorporated into the impedance measurement.

Electrodes attached to the mid-axillary line at the level of the sixth rib yielded the maximum impedance change during respiration. However, the greatest linearity between the two variables was attained by placing the electrodes higher on the thorax. Despite the high degree of linearity reported, large standard deviations of impedance changes during respiration have been reported. However, the variability observed in impedance measurements is comparable to those seen in measurements of other vital signs, such as blood pressure. Groups have shown that impedance pneumography methods are sufficiently accurate for clinical purposes. Furthermore, in the 40 years since these studies, electrode materials and signal processing of the impedance measurements have greatly improved, yielding even more reliable measurements. Digital signal processing allows for the near instantaneous filtering and smoothing of real-time impedance measurements, which allows for the minimization of artifacts and noise. More recently, respiratory impedance has been used successfully in long-term patient monitoring. As long as the electrodes remain relatively unmoved, the relationship of change in impedance to change in volume is stable for long periods of time.

Active Acoustic System

The most common use of acoustics in relationship to the lungs is to evaluate sounds that originate in the lungs acquired by the use of a stethoscope. One frequently overlooked property of lung tissue is its ability to act as an acoustic filter. It attenuates various frequencies of sound that pass through them to different extents. There is a relationship between the level of attenuation and the amount of air in the lungs. Motion of the chest wall also results in frequency shift of acoustic signals passing through the thorax.

Potential for Detecting Abnormalities

Many useful indicators, such as the forced vital capacity (FVC) and forced expiratory volume in one second ($FEV_1$), can be extracted from monitoring the volume trace of a patient's respiration with impedance pneumography. The FVC and FEV1 are two benchmark indicators typically measured by a spirometer and are used to diagnose and monitor diseases such as COPD, asthma, and emphysema. In addition to monitoring the respiration, impedance pneumography can also simultaneously record the electrocardiogram from the same electrodes.

Breath-to-Breath Variability

Calculations such as breath to breath variability, coefficient of variance, standard deviation, and symmetry of a tidal volume histogram have been shown to be dependent on age and respiratory health. Compared to normal subjects it has been shown that some of these parameters, particularly coefficient of variance, are significantly different in patients with tuberculosis, pneumonitis, emphysema, and asthma. Furthermore, it has been noted in the literature that impedance measurements were satisfactory as long as the electrodes did not move on the patient. In general, it has been determined by many groups that healthy subjects show greater variability in breathing patterns than subjects in a pulmonary disease state.

The nonlinear analysis of respiratory waveforms has been used in a wide array of applications. In examining the regularity of nonlinear, physiologic data, studies have shown that within pulmonary disease states, patients exhibit a decrease in breath-to-breath complexity. This decrease in complexity has been demonstrated within chronic obstructive pulmonary disease, restrictive lung disease, and within patients that fail extubation from mechanical ventilation. Reduced variability has also been determined to be a result of sedation and analgesia. In broad terms, normal patients have greater breath to breath variability than those afflicted by some form of pulmonary disease or compromise.

The respiratory pattern is nonlinear, like any physiologic data, as it is influenced by a multitude of regulatory agents within the body. Within the analysis of breath-to-breath variability, various entropy metrics are used to measure the amount of irregularity and reproducibility within the signal. These metrics can be used within the analysis of RVM tidal volume tracings in assessing not only breath-to-breath changes, but intrabreath variability, as well as magnitude, periodicity, and spatial location of the curve.

Universal calibration of the system based off standardized patient characteristic data (Crapo) allows for the creation of a complexity index, and comparison of a single patient to what is defined as a normal level of complexity. This index would be used to aid clinicians in determining the appropriate time to extubate, determining the severity of cardiopulmonary disease, and also within the assessment of therapeutics. This index would be independent of the method in which data is collected, whether through an impedance based device, accelerometers, a ventilator, or an imaging device. The system could also be calibrated to a specific patient and focus on intra-subject variability while detecting rapid changes within any of the respiratory parameters.

Nonlinear Analysis of Interbreath Intervals

In addition to variability metrics, some groups have found that nonlinear analysis of instantaneous interbreath intervals are highly correlated to the success of weaning from a mechanical ventilator. These metrics are useful indicators of pulmonary health and can assist in clinical decisions. The inability for a patient to separate from a mechanical ventilator occurs in approximately 20% of patientsand current methods to predict successful separation are poor and add little to a physician's decision. In a study with 33 subjects under mechanical ventilation for greater than 24 hours, it was found that 24 subjects were successfully weaned from ventilation while 8 subjects failed (data from one subject was removed). The reasons of failure were cited as hypoxia in five subjects, and tachypnea, hypercapnia, and upper airway edema for the remaining three, all of which are diseases that can be potentially identified by an impedance pneumography system. The primary finding in this study was that the nonlinear analysis of instantaneous breath intervals for those who failed to separate from the mechanical ventilator was significantly more regular than those who separated successfully. Furthermore, it was shown that the respiratory rate did not differ between the two groups. The metrics derived from nonlinear analysis of impedance pneumography measurements can successfully predict patient outcomes. In addition, these metrics have been shown to be robust and did not significantly change when artifacts such as coughing were introduced.

Detection of Decreased Ventilation States

The respiratory trace produced by impedance pneumography as well as the average impedance of a subject can indicate states of decreased ventilation or changes in fluid volume in the thorax. This type of monitoring would be useful for the care of anesthetized patients. Respiratory monitoring with impedance pneumography in anaesthetized or immobile patients is shown to be accurate and reliable for long periods, especially during the critical period in the recovery room after surgery. Investigators have determined that fluid in the thorax or lungs can lead to measurable changes in impedance, which can be used to determine common problems for patients in the recovery room such as pulmonary edema or pneumonia.

In addition to measuring changes in fluid volume in the thorax, changes in tidal volume and upper airway resistance are immediately apparent in impedance measurements. Investigators found that endotracheal clamping of anaesthetized patients still produced a diminished impedance signal despite the patient's effort to breathe, thereby giving a correct indication of ventilation. It has also been shown that impedance measurements provide quantitative assessment of the ventilation of each lung. Differences in impedance measurements were observed in patients with unilateral pulmonary lesions, with a pair of electrodes on the injured side of the thorax producing a less pronounced signal than the normal side.

Respiratory Monitors

While certain contact probes record respiratory rate, to date, no device or method has been specifically devised to record or to analyze respiratory patterns or variability, to correlate respiratory patterns or variability with physiologic condition or viability, or to use respiratory patterns or variability to predict impending collapse. Heart rate variability algorithms only report on variations in heart rate, beat-to-beat. It is desirable to use respiratory rate variability algorithms to incorporate variability in respiratory intensity, rate, and location of respiratory motion. Marked abnormalities in respiration as noted by changes in intensity, in rate, in localization of respiratory effort, or in variability of any of these parameters provide an early warning of respiratory or cardiovascular failure and may present an opportunity for early intervention. Development of a device to record these changes and creation of algorithms that correlate these respiratory changes with severity of illness or injury would provide not only a useful battlefield tool, but also one of importance in the hospital critical care setting to help evaluate and treat critically ill patients. Use in the clinic or home setting could be of use to less critically ill patients that nonetheless would benefit from such monitoring. For example, respiratory rate drops and respirations become "shallow" if a patient is overly narcotized. Respiratory rate and respiratory effort rise with stiff lungs and poor air exchange due to pulmonary edema or other reasons for loss of pulmonary compliance. However, the implications of the rate, which is the only parameter objectively monitored is frequently not identified soon enough to best treat the patient. A system that could provide a real time, quantitative assessment of work of breathing and analyze the trend of respiratory rate, intensity, localization, or variability in any or all of these parameters is needed for early diagnosis and intervention as well as therapeutic monitoring. Such a system is needed to judge the depth of anesthesia, or the adequacy or overdose of narcotic or other pain relieving medications.

PCA and Feedback Controls

Patient Controlled Analgesia (PCA) is a method of post-operative pain control that includes patient feedback. The administration of opiates can suppress respiration, heart rate, and blood pressure, hence the need for careful and close monitoring. The system comprises a computerized pump that contains pain medication that can be pumped into the patient's IV line. Generally, in addition to a constant dose of pain medication, the patient may press a button to receive care in the form of additional medication. However, patients are discouraged from pressing the button if they are getting too drowsy as this may prevent therapy for quicker recovery. There are also safeguards in place that limit the amount of medication given to a patient in a given amount of time to prevent overdose. Pulse oximeters, respiratory rate and capnograph monitors may be used to warn of respiratory depression caused by pain medication and cut off the PCA dose, but each has serious limitations regarding at least accuracy, validity, and implementation.

SUMMARY OF THE INVENTION

The methods and devices described below provide for techniques that accurately calculate breathing volumes, measure a variety of respiratory parameters and detect respiratory abnormalities. Patient or subject monitoring is essential and is rapidly spreading throughout hospital divisions. Specifically, respiratory monitoring is necessary in intensive care units, during anesthesia procedures, and post-operative periods. Respiratory rate is already used to assess patient status, but respiratory rate alone does not indicate important respiratory changes, and therefore it is necessary to monitor other respiratory parameters. Current methods that can indicate additional respiratory parameters, such as spirometry and end tidal $CO_2$ measurements, are inconvenient or inaccurate or impossible to implement on sedated patients or those who cannot or will not cooperate. A respiratory monitoring device that can detect additional respiratory parameters in a convenient and accurate manner would greatly benefit patient monitoring and detection of pathologies.

Preferably, the device provides the measurements of at least one additional respiratory parameter. This respiratory parameter is reflected though a measurement that reports, that correlates with, or that measures the subject's respiratory rate, the subject's respiratory pressure, the subject's respiratory flow, the subject's end tidal $CO_2$, the subject's sublingual $CO_2$, the subject's intensity of respiration.

One embodiment of the device provides data, based on measurements, that reports, correlates with, or measures the following parameters or that reports, correlates with, or measures variability, variation, or complexity in the following parameters: shape of the subject's respiratory curve, change in shape of the subject's respiratory curve, a respiratory curve based on the subject's inhaled volume, a respiratory curve based on the subject's exhaled volume, a respiratory curve based on the subject's inhaled pressure, a respiratory curve based on the subject's exhaled pressure, a respiratory curve based on the subject's inhaled flow, a respiratory curve based on the subject's exhaled flow, a respiratory curve based on motion of the subject's chest as measured by imaging, a respiratory curve based on motion of the subject's chest as measured by contact sensors placed on the chest, a respiratory curve based on motion of the subject's abdomen as measured by imaging, a respiratory curve based on motion of the subject's abdomen as measured by contact sensors placed on the abdomen, a respiratory curve based on motion of both the subject's chest and abdomen as measured by imaging, a respiratory curve based on motion of the subject's chest and abdomen as measured by contact sensors placed on the chest and abdomen, variation of the subject's interbreath intervals, phase lag between the subject's impedance and volume signal, variation of phase lag between the subject's impedance and volume signal, and combinations thereof.

In a preferred embodiment, the device provides a measurement of variation, variability or complexity in the respiratory parameter of at least one additional respiratory parameter. This respiratory parameter is reflected through a measurement that reports, that correlates with or that measures: the subject's respiratory rate, the subject's respiratory pressure, the subject's respiratory flow, a measurement that correlates with a subject's end tidal $CO_2$, a measurement that correlates with the subject's sublingual $CO_2$, the subject's intensity of respiration, depth of the subject's respiration, localization of the subject's respiration, One embodiment of the device provides a measurement that reports, that correlates with or that measures: variation of the subject's interbreath intervals, phase lag between the subject's impedance and volume signal, variation of phase lag between the subject's impedance and volume signal, and combinations thereof.

Preferably, the monitoring device will use one or more of the following: impedance pneumography, acoustics, end tidal $CO_2$ measurements, pulse oximetry to measure respiratory volumes and other respiratory parameters. Preferably, the device will utilize signal processing algorithms to minimize noise and electrical interference of raw impedance data to produce a smooth, clear trace that will be known henceforth as a Respiratory Variation Monitoring (RVM) measurement, trace, or curve. Preferably, the respiratory parameters are used to calculate ATS standardized values for spirometry tests, including but not limited to Forced Vital Capacity (FVC), Forced Expiratory Volume for one second (FEV1), Forced Expiratory Volume for six seconds, (FEV6), Forced Expiratory Flow (FEF), Peak Expiratory Flow (PEF), Forced Inspiratory Vital Capacity (FIVC), Peak Inspiratory Flow (PIF), Tidal Volume (TV), Inspiratory Capacity (IC), Expiratory Reserve Volume (ERV), Inspiratory Reserve Volume (IRV), Slow Vital Capacity (SVC), Maximum Ventilatory Volume (MVV), Vital Capacity (VC), and Breaths Per Minute (BPM).

More preferably the device will be used to monitor tidal volume, respiratory rate and minute ventilation over time most preferably for over one hour, over 4, 6, 8, 12, 24 hours. Most preferably, the device will be able to adjust to and report changes in respiratory paramenters or variation, variability or complexity thereof over time.

Preferably the device will be able to measure respirations that are erratic and not smooth and consistent. Preferably these measurements will be reported in near-real time, under 10 seconds, under 20 seconds under 30 seconds under 1 minute, under 2 minutes.

Preferably, the device will input measured parameters to calculate a unique index for respiratory sufficiency, a respiratory sufficiency index (RSI) which is utilized in patient diagnostics and monitoring. In particular, for patients who are unable to comply with the procedure, a simple tidal breathing sample will be taken, which requires no coaching or compliance. RSI measurement will be utilized by caregivers to adjust care plans.

In one embodiment, Respiratory Variation Monitoring uses impedance pneumograph to provide a similar type of respiratory assessment found in a pulmonary function lab. Though the spirometry metrics recommended by the American Thoracic Society (ATS) cannot be directly calculated without undergoing prescribed maneuvers, other information in the impedance trace can be used in place of, or as a supplement to these metrics when diagnosing a range of pulmonary disease states. Respiratory variation monitoring by impedance plethysmography offers a novel non-invasive, non-obstructive alternative to spirometry, with the additional advantage that unconscious or noncompliant patients may be examined. Although patients cannot perform the same maneuvers as in spirometry while in such a state, respiratory parameters that are given by a spirometry test, such as FEV1 (forced expiratory volume over one second) and FVC (forced vital capacity), may be measured or estimated utilizing an impedance trace of tidal volume. Moreover, the utility of the FEV1 and FVC measurement is to provide a metric useful in quantifying the level of pulmonary function and differentiating between obstructive and restrictive lung disorders. In asthma (an obstructive lung disorder) the forced expiratory volume in 1 second (FEV1) is usually decreased, the forced vital capacity (FVC) is usually normal and the ratio FEV1/FVC is decreased. In restrictive disorders the FEV1 and FVC are both decreased, leaving a normal FEV1/FVC. RVM measurements can deliver FEV1 and FVC measurements without requiring the patient to breathe into a machine that had a mouthpiece that requires attention to hold in the mouth which impacts results. RVM does not have any device in the respiratory pathway of inspired or expired air that could impede or alter the flow or volume of respiration or could contaminate the airstream. In reality, it is the measurements of pulmonary sufficiency and adequacy of ventilation that are of interest, and using RVM, a different parameter, or different parameters, other than FEV1 or FVC provide similar or better data to assist in measuring or monitoring lung function to aid in the diagnosis and management of restrictive or obstructive airway disease. These data are obtained from analysis of the shape of the respiratory curve, the phase shift, or breath-to-breath variability.

Another method uses acoustics to provide Respiratory Variation Monitoring. An apparatus comprising speakers and microphones on the chest of a patient can be used to monitor the acoustic properties of the lungs and thorax to estimate lung volumes. As with impedance pneumography, acoustic respiratory monitoring does not impede airflow and can be used with unconscious and noncompliant patients. Besides estimating lung volumes, the microphones can also be used to assess the other parameters associated with the condition of the patient and detect signs of respiratory degradation.

Impedance plethysmography has been researched for about half a century. An effort of particular interest is the ability to produce volume curves from impedance data given a "scaling factor". This scaling factor has previously been derived by comparing the impedance trace to volume data recorded simultaneously using a spirometer. However, the novel approach taken is to calculate instead an "RVM calibration coefficient" given patient physiology and history and other measurable parameters, such as height, weight, BMI, BSA, age, gender, ethnicity, and other physical characteristics or physiologic, metabolic or laboratory parameters. This strategy separates the importance of relative impedance for volume change from the overall impedance of the thorax. The noninvasive impedance-based device monitors respiratory frequency and tidal volume and serves in lieu of standard spirometry-based values which are useful for both diagnostics and patient monitoring and less reliant on operator skill. The RVM calibration coefficient can also be derived from measurements taken during standard pulmonary function testing with a spirometer, pneumotachometer or other pneumograph or from readings off of a ventilator for an intubated patient.

One new RVM measurement that is useful for physicians and diagnostics is a novel approach to RVM known as a Respiratory Health Index (RHI). This index utilizes RVM data and patient parameters to create a percentage value for respiratory health. The value is derived from utilizing the tables of normal spirometry figures for varying patient demographics found in the work of Knudsen, Crapo, and others. For example, for tidal breathing the normal values for a person of the same height, weight, gender, and ethnicity as the patient are found and then compared to the real values by dividing the real values by the tabulated values to create a percentage. The peak-to peak change in RHI should be close to 100% to indicate good health.

Preferably, the analysis of the at least one respiratory parameter comprises correlating the at least one respiratory parameter with a predefined respiratory condition. Preferably the analysis provides an adjunct to diagnosis. More preferably the analysis provides a diagnosis. Preferably the analysis provides a information to be integrated with other monitoring or clinical data to serve as an adjunct in the management of therapeutics.

Preferably the analysis provides information to guide the management of therapeutics. Preferably, the device provides a prediction of future patient status. More preferably, the prediction is a prediction of the subject's viability, a prediction of injury severity, a prediction of the subject's likelihood of collapsing, a prediction of the subject's likelihood of suffering respiratory failure, a prediction of the subject's depth of anesthesia, a prediction of the subject's drug dosage level, a prediction of the subject's likelihood of cardiopulmonary failure, a prediction of the likelihood of equipment failure for equipment associated with treating the patient, a prediction of the adequacy or inadequacy of ongoing therapy, or combinations thereof.

Preferably, the device recognizes respiratory patterns associated with pathologies such as COPD, asthma, emphysema, tuberculosis, pneumonitis, tachypnea, hypercapnia, pulmonary edema, pneumonia, unilateral pulmonary lesions, impending or existing respiratory failure and airway obstruction.

Preferably the device recognizes respiratory patterns associated with pathologies such as cardiac, neurologic or metabolic such as congestive heart failure, cardiomyopathy, diabetic ketoacidosis, cerebral edema.

DESCRIPTION OF THE INVENTION

Figure 1:
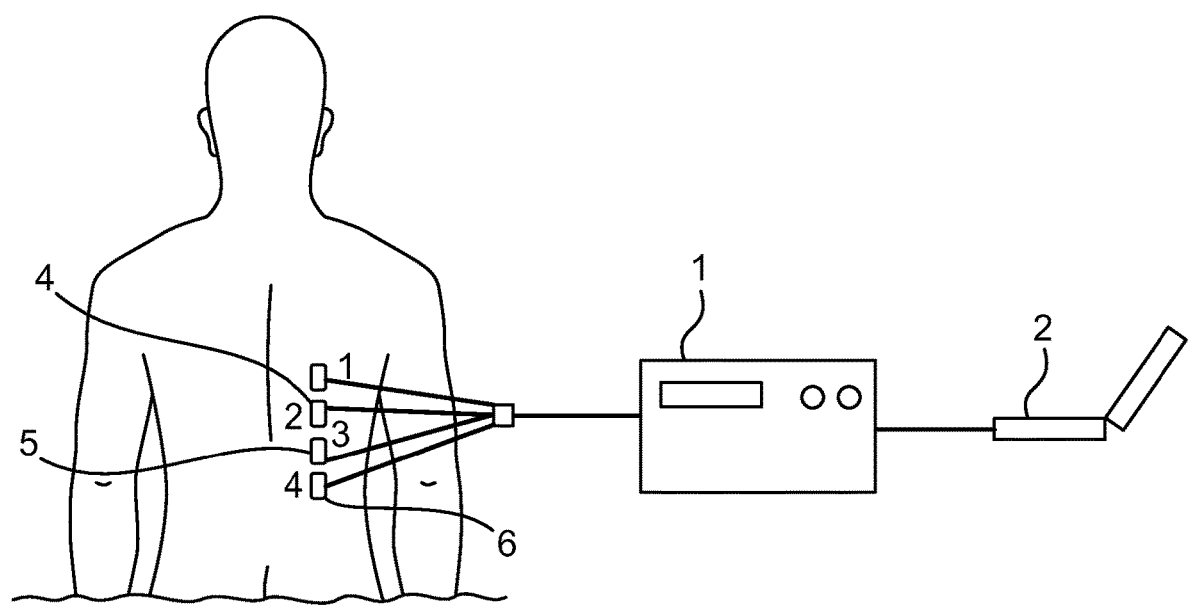
FIG. 1 is a perspective view of a four-lead embodiment of the invention.

One embodiment of the present invention is directed to a device for assessing a patient, individual or animal that collects impedance measurements by placing multiple electrode leads and/or speakers and microphones on the body. Preferably at least one impedance measuring element and a microphone/speaker functionally connected to a programmable element, programmed to provide an assessment of at least one respiratory parameter of the subject.

Preferably, the impedance measurement is based on a plurality of remote probe data sets, and wherein the programmable element is further programmed to enhance at least one of the plurality of remote probe data sets; or to stabilize at least one of the plurality of remote probe data sets; or to analyze each of the plurality of remote probe data sets for dynamic range and signal to noise ratio (SNR) values. Preferably, the device probes are maintained in several lead configurations. In one embodiment, variations in lead configuration allow for flexibility depending on the subject and test being performed. In other embodiments, variations in lead configuration allow for variability in patient anatomy. Preferably, the device maintains settings to identify valid lead configurations. Preferably, the device maintains settings to identify valid lead attachment.

Preferably, the device or method as described in a protocol embedded in the machine instructs as to lead placement. Preferably, appropriate lead contact is verified by the device. Preferably, the device alerts the operator as to inadequate or inappropriate lead placement.

Preferably, the device monitors continuously or intermittently and maintains alarms to indicate when a respiratory parameter reflects a loss in ventilation or other vital function. The alarm is set based on a respiratory sufficiency index, on minute ventilation, on respiratory rate, on tidal volume, on an inspiratory volume or flow parameter, on an expiratory volume or flow parameter, on variability of respiratory rate, volume, flow or other parameter generated. For example, the alarm goes off if the monitor detects a decrease in either respiratory frequency or depth or minute ventilation associated with hypoventilation or detects an increase in any or all of these parameters that would suggest hyperventilation. An alarm is used on a hospital floor in comparing the patient's current respiratory status with a baseline level based on specific individual calibration to ventilator or spirometer. Preferably, the alarm is set based on parameters taken for the given individual from a ventilator or spirometer. More preferably the baseline level is based on one or more of the following: demographic, physiologic and body type parameters. An alarm is also used to alert for narcotic induced respiratory depression at a point that is determined to be detrimental to the patient. Preferably, the ranges of values beyond which alarms will be triggered are chosen by the physician or care giver for one or more of the following: respiratory rate, tidal volume, minute ventilation, respiratory sufficiency index, shape of the respiratory curve, entropy, fractal or other analysis parameters associated with respiratory variability or complexity.

In another embodiment, the RVM measurements taken at any given point in time is recorded as baseline. These recorded values are correlated to subjective impression by a physician or other health care worker of patient status. Subsequently, RVM is monitored and an alarm set to alert health care staff if a 10%, 20% or other selected percentage change in respiratory volumes, minute ventilation curve characteristics, or variability is noted. The following illustrate embodiments of the invention, but should not be viewed as limiting the scope of the invention.

Impedance Plethysmograph

As embodied and broadly described herein are provided detailed embodiments of the invention. The embodiments are merely exemplary of the invention that may be embodied in various and alternative forms. Therefore, there is no intent that specific structural and functional details should be limiting, but rather the intention is that they provide a basis for the claims and as a representative basis for teaching one skilled in the art to variously employ the present invention.

The invention preferably comprises an impedance pneumograph with integrated electronics to convert measured impedance values to volume and display the volume to an end-user through an electronic interface or printed reports employing numerical or graphical representations of the data. The impedance measuring device comprises circuitry, at least one microprocessor and preferably at least four leads. Preferably, where at least two leads are used for injecting current into the subject's body and at least two are used for reading the voltage response of said patient's body.

In one embodiment, the device preferably comprises an integrated module to simulate a patient and allow for automated system testing and demonstrations. Automated system tests improve the performance of the device and ensure that it is functioning correctly before use.

In the preferred embodiment, the device utilizes an analog divider to compensate for slight deviations in the injected current and increase the accuracy of acquired data. The analog divider in the preferred embodiment would be placed after the demodulator and before the rectifier. In other embodiments the analog divider may be placed in other locations in the circuit including, but not limited to, after the precision rectifier or before the demodulator.

In the preferred embodiment, the device utilizes adaptive electronics driven by a microprocessor to maintain the appropriate gains on the different amplifiers in the circuit to prevent the signal from going out of range. The microprocessor tracks the set gains at each of the hardware amplifiers and compensates appropriately during its calculations so that it always outputs an appropriate value.

The impedance measuring device is preferably connected to computer via a digital interface (e.g. USB, Fire wire, serial, parallel, or other kind of digital interface). The digital interface is used to prevent data from corruption during transfer. Communication over this interface is preferably encrypted to further ensure data integrity as well as protect the invention from usage of counterfeit modules (either measuring device or computer).

Referring now to a preferred embodiment of the invention in more detail, in FIG. 1 there is shown an impedance plethysmograph, comprising a radio frequency impedance meter 1, a programmable element 2 contained on a PC linked to the meter, which is connected to the patient by four leads, namely a first lead 3, a second lead 4, a third lead 5, and a fourth lead 6. Each lead is preferably connected to a surface electrode, namely a first surface electrode, a second surface electrode, a third surface electrode, and a fourth surface electrode.

In further detail, still referring to the embodiment of FIG. 1, the electrodes can be made of a conductive material such as AgCl, coated with an adhesive, conductive material such as a hydrogel or hydrocolloid. The leads can be made of any conductive material such as copper wire and are preferably coated with insulating material such as rubber. In a preferred embodiment, wireless electrodes are utilized to provide current and collect and transmit data. Preferably, this lead composition is coupled with Bluetooth technology and a receiver.

Leads 1 and 4 are connected to a current source with a constant frequency preferably greater than 20 KHz, which is great enough to avoid interfering with biological signaling. The amplitude of the current source is preferably less than 50 mA, and below the level that would cause fibrillation at the chosen frequency. The differential voltage between leads 2 and 3 is used to calculate the impedance according to ohm's law. By sampling the voltage measurements taken by the impedance meter, the programmable element (such as a PC) tracks and plots changes in thoracic impedance that correspond to biological functions such as heartbeat and breathing. The changes in impedance are then used to monitor pulmonary function. Preferably, the device is calibrated by a method laid out herein to calculate the lung volumes and display them to an operator.

Figure 28:
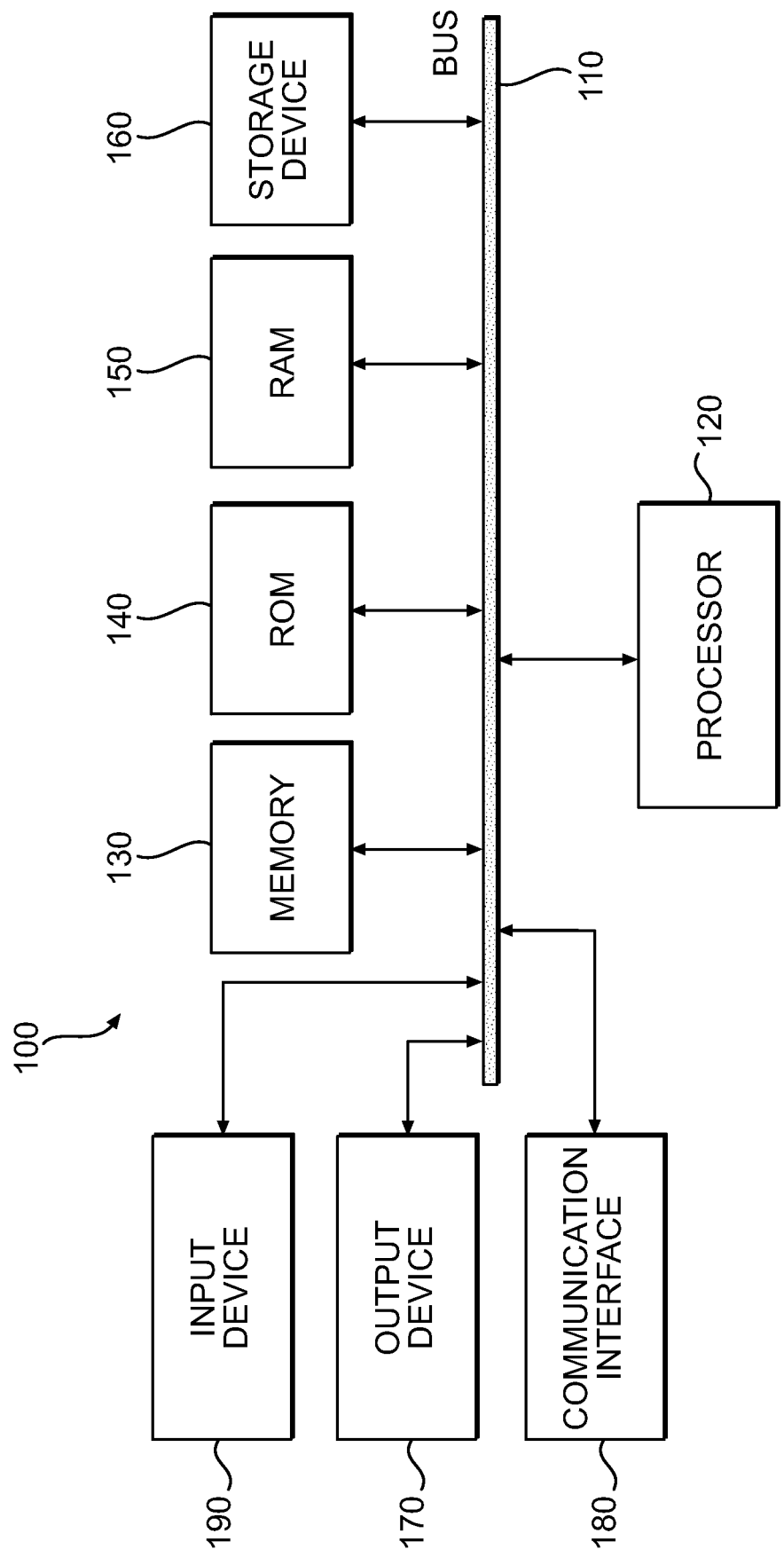
FIG. 28 illustrates an embodiment of a system of the invention.
Figure 29:
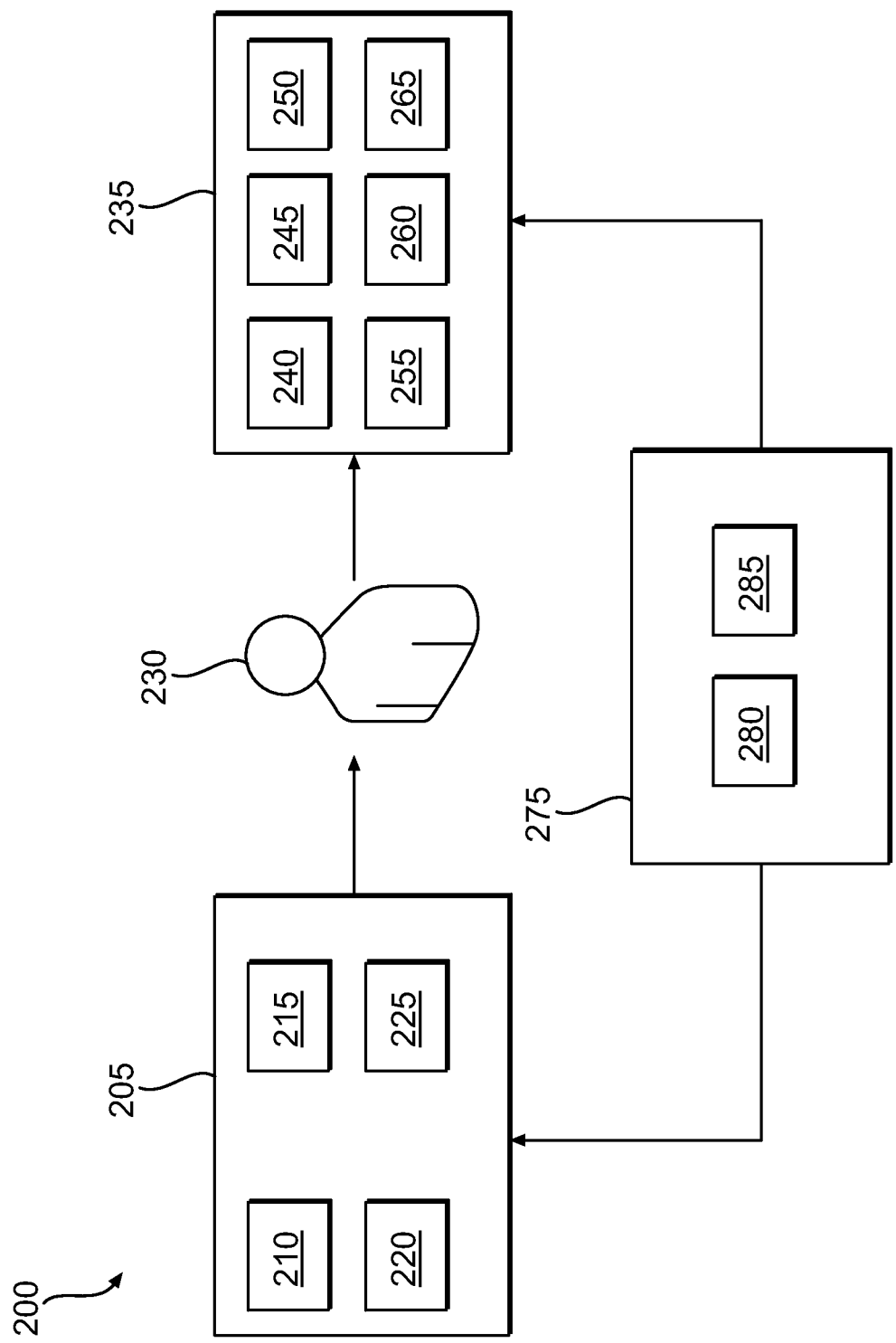
FIG. 29 illustrates an embodiment of the device of the invention.

With reference to FIG. 28, an exemplary and preferred system includes at least one general-purpose computing device 100, including a processing unit (CPU) 120, and a system bus 110 that couples various system components including the system memory such as read only memory (ROM) 140 and random access memory (RAM) 150 to the processing 25 unit 120. Other system memory 130 may be available for use as well. The invention preferably operates on a computing device with more than one CPU 120 or on a group or cluster of computing devices networked together to provide greater processing capability. The system bus 110 may be any of several types of bus structures including a memory bus or memory controller, a peripheral bus, and a local bus using any of a variety of bus architectures. A basic input/output (BIOS) stored in ROM 140 or the like, preferably provides the basic routine that helps to transfer information between elements within the computing device 100, such as during start-up. The computing device 100 further preferably includes storage devices such as a hard disk drive 160, a magnetic disk drive, an optical disk drive, tape drive or the like. The storage device 160 is connected to the system bus 110 by a drive interface. The drives and the associated computer readable media provide nonvolatile storage of computer readable instructions, data structures, program modules and other data for the computing device 100. The basic components are known to those of skill in the art and appropriate variations are contemplated depending on the type of device, such as whether the device is a small, handheld computing device, a desktop computer, a laptop computer, a computer server, a wireless devices, web-enabled devices, or wireless phones, etc.

In some embodiments, the system is preferably controlled by a single CPU, however, in other embodiments, one or more components of the system is controlled by one or more microprocessors (MP). Additionally, combinations of CPUs and MPs can be used. Preferably, the MP is an embedded microcontroller, however other devices capable of processing commands can also be used.

Although the exemplary environment described herein employs the hard disk, it should be appreciated by those skilled in the art that other types of computer readable media which can store data that are accessible by a computer, such as magnetic cassettes, flash memory cards, digital versatile disks, cartridges, random access memories (RAMs), read only memory (ROM), a cable or wireless signal containing a bit stream and the like, may also be used in the exemplary operating environment. To enable user interaction with the computing device 100, an input device 190 represents any number of input mechanisms, such as a microphone for speech, a touch sensitive screen for gesture or graphical input, electrical signal sensors, keyboard, mouse, motion input, speech and so forth. The device output 170 can be one or more of a number of output mechanisms known to those of skill in the art, for example, printers, monitors, projectors, speakers, and plotters. In some embodiments, the output can be via a network interface, for example uploading to a website, emailing, attached to or placed within other electronic files, and sending an SMS or MMS message. In some instances, multimodal systems enable a user to provide multiple types of input to communicate with the computing device 100. The communications interface 180 generally governs and manages the user input and system output. There is no restriction on the invention operating on any particular hardware arrangement and therefore the basic features here may easily be substituted for improved hardware or firmware arrangements as they are developed.

Embodiments within the scope of the present invention may also include computer readable media for carrying or having computer-executable instructions or data structures stored thereon. Such computer-readable media can be any available media that can be accessed by a general purpose or special purpose computer. By way of example, and not limitation, such computer-readable media can comprise RAM, ROM, EEPROM, CD-ROM or other optical disk storage, magnetic disk storage or other magnetic storage devices, or any other medium which can be used to carry or store desired program code means in the form of computer-executable instructions or data structures. When information is transferred or provided over a network or another communications connection (either hardwired, wireless, or combination thereof) to a computer, the computer properly views the connection as a computer-readable medium. Thus, any such connection is properly termed a computer readable medium. Combinations of the above should also be included within the scope of the computer-readable media.

Computer-executable instructions include, for example, instructions and data which cause a general purpose computer, special purpose computer, or special purpose processing device to perform a certain function or group of functions. Computer-executable instructions also include program modules that are executed by computers in stand-alone or network environments. Generally, program modules include routines, programs, objects, components, and data structures, etc. that perform particular tasks or implement particular abstract data types. Computer-executable instructions, associated data structures, and program modules represent examples of the program code means for executing steps of the methods disclosed herein. The particular sequence of such executable instructions or associated data structures represents examples of corresponding acts for implementing the functions described in such steps.

Those of skill in the art will appreciate that other embodiments of the invention may be practiced in network computing environments with many types of computer system configurations, including personal computers, hand-held devices, multi-processor systems, microprocessor-based or programmable consumer electronics, network PCs, mini-computers, mainframe computers, and the like. Networks may include the Internet, one or more Local Area Networks ("LANs"), one or more Metropolitan Area Networks ("MANs"), one or more Wide Area Networks ("WANs"), one or more Intranets, etc. Embodiments may also be practiced in distributed computing environments where tasks are performed by local and remote processing devices that are linked (either by hardwired links, wireless links, or by a combination thereof) through a communications network. In a distributed computing environment, program modules may be located in both local and remote memory storage devices.

Figure 2:
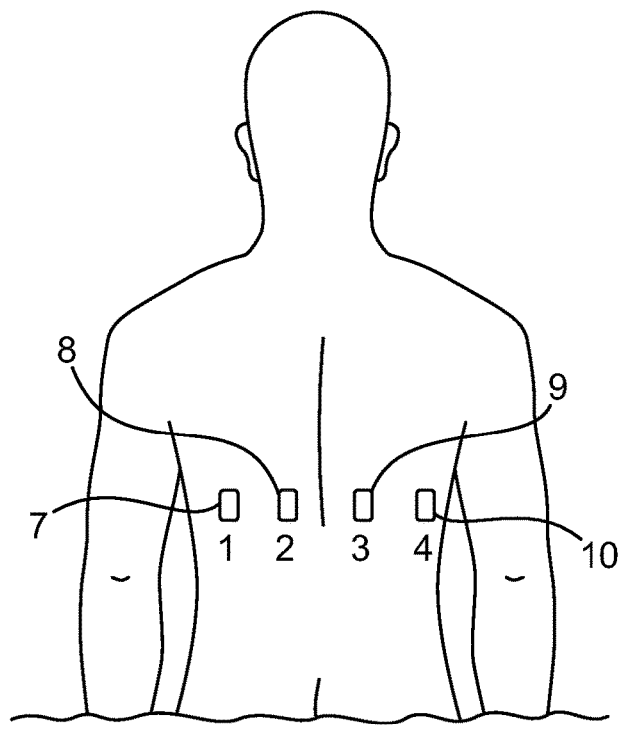
FIG. 2 is a diagram of the Posterior Left to Right electrode configuration.

FIG. 2 is a schematic of an embodiment of a system 200 of the invention. The electrical source originates from signal source 205. Preferably, an adjustable function generator 210 (e.g. a XR2206 chip) is used to generate the electrical source. The function generator 210 is preferably adjustable via a microprocessor (MP) 275 or manually. In some embodiments, the function generator can be tuned in order to improve the signal. Tuning can occur once or multiple times. Bio-impedance spectroscopy can be used to detect levels of hydration at different frequencies, which can be used to calibrate function generator 210. Similarly, body fat percentages can be calculated. Signal source 205 also comprises a current generator 215 (e.g. a Howland circuit). Current generator 215 preferably keeps the source current constant despite changes in pad contact (unless the contact is totally broken). In the preferred embodiment, current generator 215 can be tuned to improve performance, which can be done manually or automatically by the MP 275. The impedance measuring subsystem may utilize current generating components at one or more frequencies, which may be active simultaneously, or sequentially. Voltage measuring components may be functionally connected to one or more electrodes. The impedance measuring subsystem may utilize non-sinusoidal current, such as narrow current pulses. The system may integrate additional sensors, such as accelerometers, moisture and acoustics sensors, capnography or oximetry sensors.

In preferred embodiments, the pad contact quality is monitored and a warning is produced when the pad contact is broken or too poor quality for the electronics to compensate. Signal source 205 may also comprise a current monitor 220 to calculate impedance. In a preferred embodiment, signal source 205 also comprises a patient simulator 225. Patient simulator 225 can simulate changes in the impedance with parameters similar to a real patient. Patient simulator 225 can be used for testing system 200 as well as calibration of the circuitry.

Figure 30:
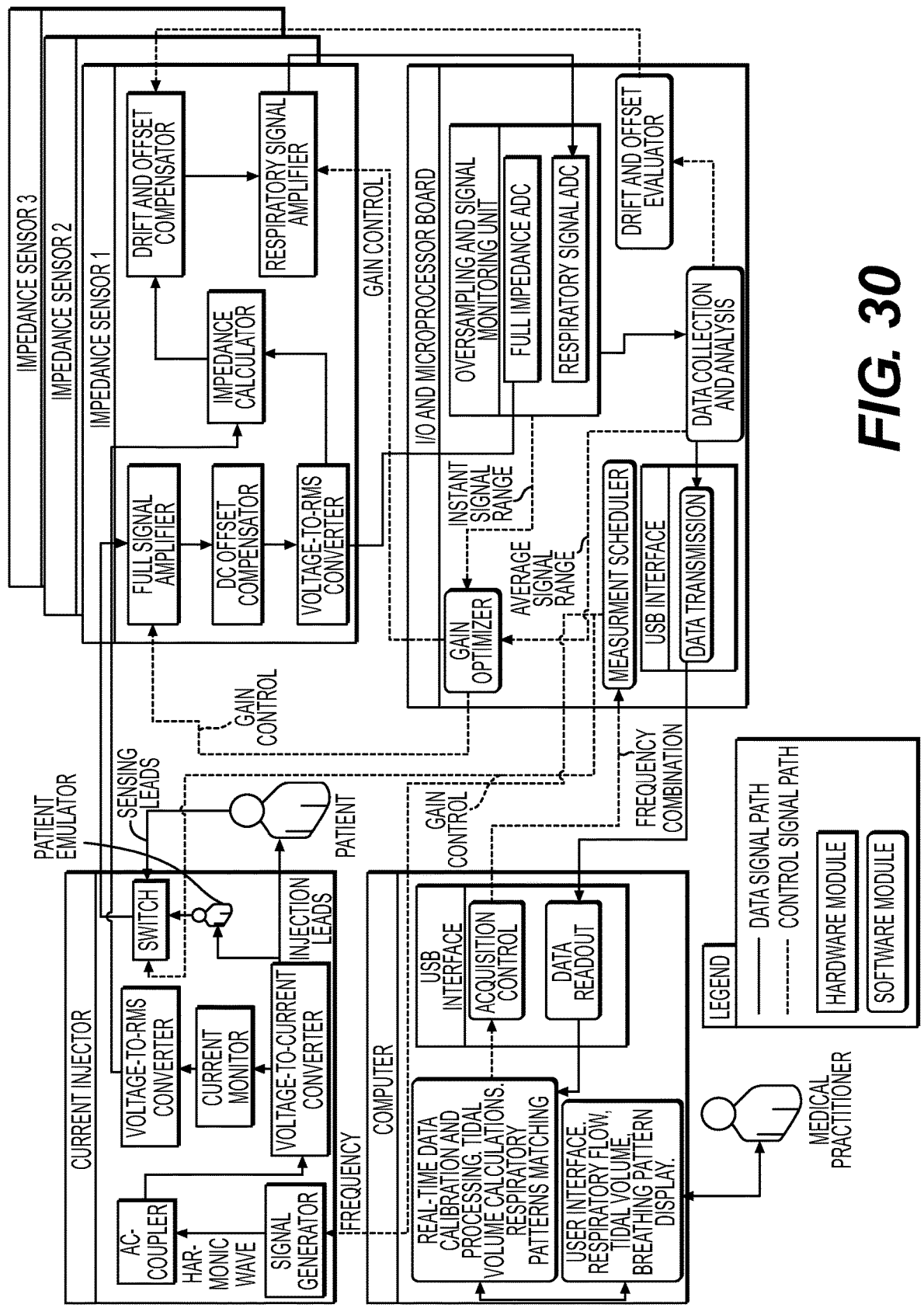
FIGS. 30-32 illustrate preferred embodiments of devices of the invention.
Figure 31:
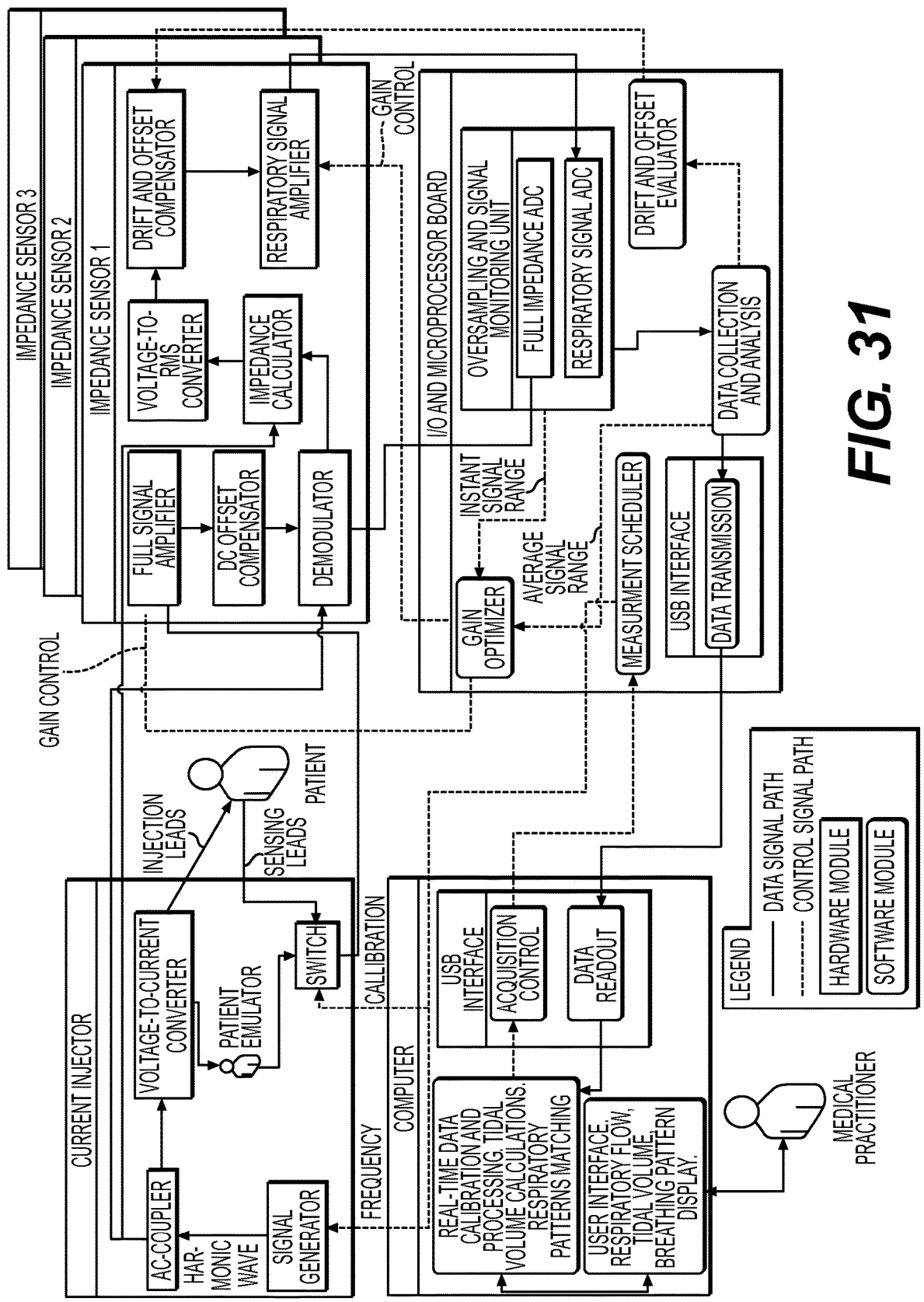

The signal from signal source 205 passes through patient 230 and is received by sensor 235. Preferably, sensor 230 comprises an input amplifier 240. Input amplifier 240 suppresses the effect of poor or variable pad contact on measurement. The gain of input amplifier 240 is preferably controlled by the MP 275 to provide an enhanced signal to the other modules. Sensor 230 preferably also comprises a signal filter 245 to remove interference from the power grid, etc. Signal filter 245 may be a standard high-pass filter (as on FIG. 30), a demodulator (as on FIG. 31), or another signal filter. Synchronous demodulators are often used for detecting bio-impedance changes and stripping out motion artifacts in the signal.

Figure 32:
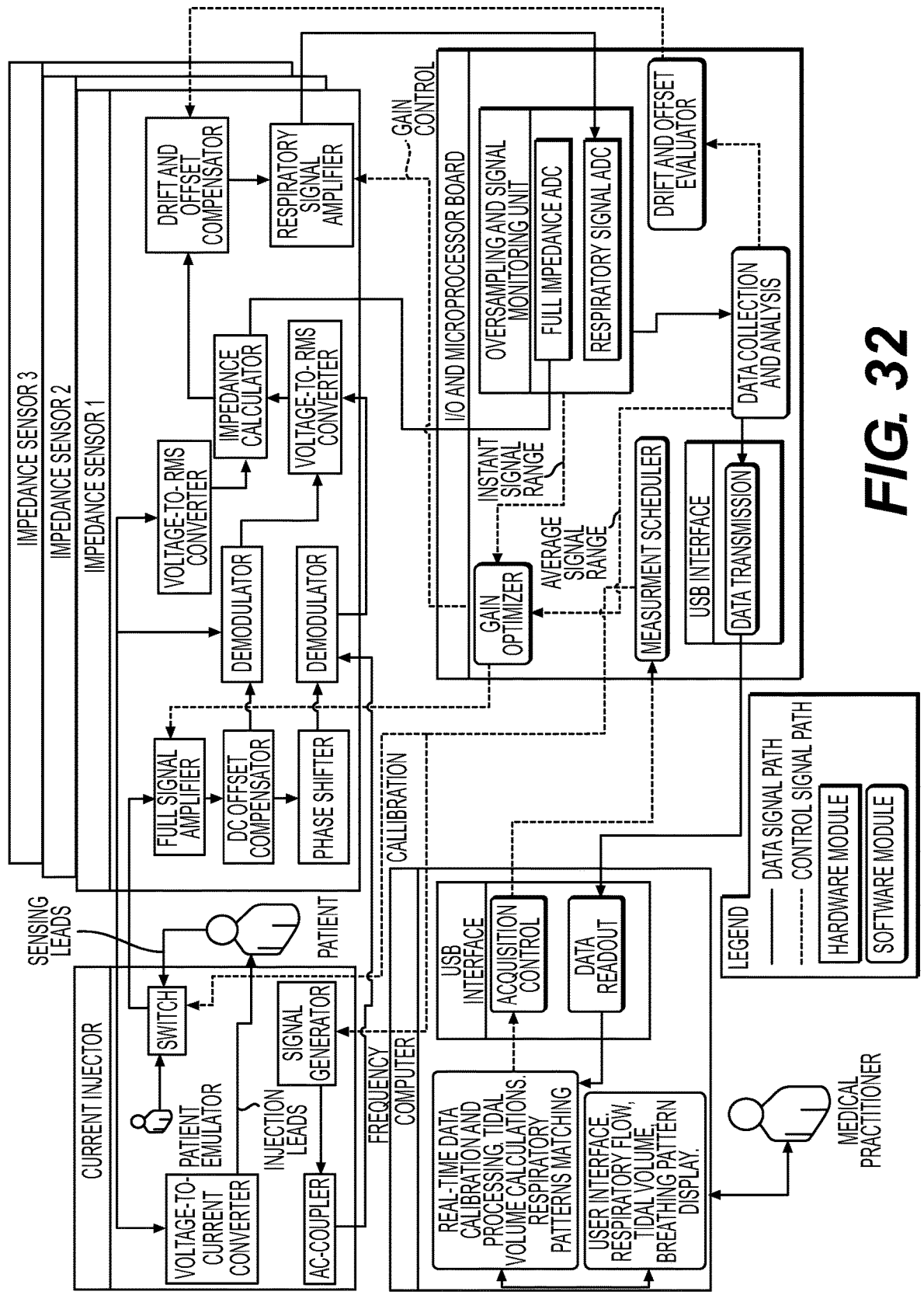

In a preferred embodiment, the signal is split into two paths (as on FIG. 32). The first path demodulates the measured signal using the generator signal as a carrier. The second path uses a 90-degree phase rotating circuitry before demodulation. Both demodulated signals can be converted into RMS values using voltage-to-RMS converters. Measured separately, the signals are summed and then the square root is calculated. This allows for compensation for any phase shift in the subject and for separate measurements of resistance and reactance, which provides valuable information for motion artifact compensation as well as hydration levels, fat percentages, and calibration coefficient calculations.

Additionally, sensor 230 may comprise an analog divider 250, which divides the measured voltage signal by the signal from the current monitoring circuit to calculate impedance. Sensor 230 preferably also comprises a precision rectifier or root mean square to direct current (RMS-to-DC) chip 255 with a low pass filter to remove the carrier frequency. The output of sensor 230 is preferably a DC signal proportional to the patient's impedance. Sensor 230 may also comprise a band-pass filter 260 to select only the respiratory rates by filtering out the portion of the signal not corresponding to the respiration. Band-pass filter 260 may be calibrated manually or automatically by the MP 275. Preferably, sensor 230 comprises a multiplexor 265 controlled by the MP 275 to accommodate multiple probe pairs. Preferably there are 2 probe pairs, however more or fewer probe pairs are contemplated. Sensor 230 may also comprise an output amplifier 270. Output amplifier 270 is preferably controlled by the MP 275 and provides a signal to an analog-to-digital converter (ADC) 280 for high precision digitization. Oversampling is used to reduce measurement noise which may originate from different sources (e.g., thermal, electronic, biological, or EM interference). MP 275 commands ADC to take measurements with as high a cadence as possible and then averages the obtained data over the time intervals corresponding to the sampling frequency. The sampling frequency is the frequency of the impedance sampling as it is presented to the computer by the impedance measuring device. The frequency is preferably set sufficiently high to monitor all the minute features of respiration.

Using controllable gains and oversampling preferably allows the system to measure the impedance with extremely high effective precision (estimated 28-bit for current implementation, or 4 parts per billion).

Both signal source 205 and sensor 230 are controlled by MP 275. MP 275 preferably comprises at least one ADC 280 monitoring the signal processing, and at least one digital output 285 to control the digital potentiometers, multiplexors, op-amps, signal generator, and other devices. Preferably, MP 275 and a computer interface (e.g., via a USB interface, a serial interface, or a wireless interface).

Preferably, the MP computes values for respiratory rate (RR), tidal volume (TV) and minute ventilation (MV) as well as, tracks the trends in computed RR, TV, or MV values and performs statistical, factor, or fractal analysis on trends in real-time. The MP may tracks instantaneous and cumulative deviations from predicted adequate values for RR, TV, or MV and computes a respiratory sufficiency index (RSI).

In a preferred embodiment, the device has the capability to measure and record other parameters including but not limited to: cardiac output, end tidal CO2, oxygen perfusion, ECG and other electrophysiologic measurements of the heart. In a preferred embodiment, the impedance measuring device measures impedance cardiography and impedance pneumography simultaneously. Preferably, the additional parameters are displayed on-screen. Preferably, the respiratory impedance data are combined with the additional parameters in a meaningful way to act as an adjunct to diagnosis. Preferably, the impedance data alone, or combined with one or more additional parameters are used to provide a diagnosis of a disease state.

In one embodiment, measurements are taken from each side of the chest independently and used to evaluate both general pulmonary status and differences between right and left lung aeration or chest expansion. An example of this is, in the case of rib fractures, where there can be changes attributed to damage including pulmonary contusion, decrease in motion due to splinting or pneumothorax where both sides of the chest are monitored independently to provide side specific data. Other sources of localized pulmonary pathology can be evaluated including pneumonia, hydrothorax, chylothorax, hemothorax, hemo/pneumothorax, atelectasis, tumor, and radiation injury.

In another embodiment, information from the device is used with information from an echocardiogram, radionuclide study or other method of imaging the heart. In a preferred embodiment the device assists in the diagnosis of myocardial ischemia with one of the following: ekg, advanced electrophysiologic studies, cardiac catheterization, echocardiogram, stress testing, radionuclide testing, CT, MRI, cardiac output monitoring by impedance measurement. In one embodiment the device provides information that is used to help with collection of other signals that vary with respiration such as respiratory sounds, cardiac information, radiation detection devices, radiation therapy devices, ablation devices. In a preferred embodiment the device can assist with the timing or data collection by another modality and/or using characteristics of the respiratory curve to correct data that is collected.

In one embodiment, the device provides information about breath-to-breath variability or respiratory complexity to be used in conjunction with cardiac beat to beat variability or complexity to provide otherwise unavailable information about cardiac, pulmonary systems, or overall metabolic or neurologic status.

Lead Configuration

The proposed respiratory parameters evaluation technique relies on a highly linear relation between the parameters and measured impedance. It is not true for every electrode placement. Extensive research was conducted to select best electrode placement which preferably satisfies following conditions:

1) Highly linear relation between respiratory volume and measured impedance variations (i.e. correlation values above 96%).
2) Low level of artifacts due to patient motion.
3) Low variation between repetitive electrode applications.
4) Easy application in common clinical situation.

Capability for use with "universal calibration," which reliably determines scaling factors that depend on measurable patient body parameters without preliminary calibration with ventilator/spirometer.

Preferably, electrodes are attached horizontally to the mid-axillary line at the level of the sixth rib. Preferably, one electrode is placed at a stable location, such as immediately below the clavicle or at the sternal notch, and another electrode is place at the bottom of the ribcage or at the level of the xiphoid at the midaxillary line. However, the electrodes can be placed higher or lower on the thorax. Furthermore, electrodes may be placed in other locations and configurations (e.g. vertically along the thorax, at an angle across the thorax, or from a position on the front of the patient to a position on the back of the patent), depending on the subject to be tested, the test to be preformed, and other physiological concerns (e.g. if the patient has a pacemaker or other artificial device).

Preferably at least one impedance measuring element is present on one or more electrode leads. Preferably, two or more electrodes are arranged in a linear array, grid-like pattern, or in an anatomically influenced configuration. Preferably, four remote probes are arranged in a linear array. In another embodiment, multiple electrode leads are arranged as a net, vest, or array. Preferably, the one or more probes, electrode leads or sensors are placed on the thorax or abdomen of the subject. Preferably, the device uses single use electrodes. In other embodiments, the electrodes are hydrogel, hydrocolloids, or solid gels. Preferably, the electrode utilizes AgCl, nickel, or carbon sensors. Preferably, the electrodes come with soft cloth, foam, microporous tape, clear tape backing or another adhesive. Preferably, different, size appropriate electrodes exist for adults and neonates, with the adult electrodes larger than the neonatal ones, which are preferably 1" by ⅜" or less (2.54 cm by 0.95 cm or less). In other embodiments, sensor electrodes are the same as the probes that deliver electrical impulses to the body, or are different from the delivery electrodes, or are wireless and transmit data to a remote sensor. In another embodiment, the delivery probes are themselves sensors. In one embodiment, the stimulating electrode is battery powered. Preferably, the at least one respiratory parameter is recorded for a duration of 30 seconds, continuously, intermittently, for up to at least 3, 5, 10, 20, or 50 of the subject's breaths, for up to at least 100 of the subject's breaths, for up to at least 1000 of the subject's breaths, or for another duration. Preferably, the subject's impedance cardiogram is simultaneously recorded.

Preferably, the at least one impedance measuring element comprises one or more remote probes or electrode leads, or leads similar to standard EKG leads or similar to the leads used for measuring cardiac impedance, and wherein the programmable element is further programmed to analyze one or more remote probe or electrode lead data sets collected from the one or more remote probes or electrode leads.

In one embodiment of the invention, the impedance measurement subsystem reads impedance from multiple channels. In a preferred embodiment, a secondary voltage sensing channel is arranged at an angle to a primary voltage sensing channel. In one embodiment, the two channels share current generating electrodes. In one embodiment, the two channels also share one of the voltage sensing electrodes. Data from the two or more channels may be used in an adaptive algorithm to determine and suppress noise from motion.

Lead configuration is critical for the performance of the device in any embodiment. Preferably, one or more leads are placed on the thorax. In one embodiment, leads are placed on the thorax and abdomen to measure breathing from different regions of the body such as the thorax or the abdomen. Differences in the location of body motion associated with breathing produces information that is useful clinically for diagnosis of physiologic state and monitoring of disease and can be compensated for in calculations. Leads are placed on the thorax, neck and head in alternate configurations. In one embodiment, leads are placed in different configurations based on anatomic locations and spaced either according to specific measured distances or anatomic landmarks or a combination of both. In one embodiment, modifications of the spacing relative to body size are implemented. Preferably these modifications are related to anatomic landmarks. In a preferred embodiment, the spacings remain relatively the same for patients of all sizes from neonates to obese patients, ranging from 250 g to 400 kg. In another embodiment, the spacings vary based on an algorithm reflecting body size and habitus. Other configurations have the advantage of determining differential motion of one hemithorax vs. the other which is useful in diagnosing or monitoring unilateral or asymmetric pathology such as pneumothorax, hemothorax, empyema, cancer.

Referring now to FIG. 2, there is shown one embodiment with a specific electrode configuration called Posterior Left to Right (PLR), in which the first electrode 7 is placed 6 inches to the left of the spine at the level of the xiphoid process, the second electrode 8 is placed 2 inches to the left of the spine at the level of the xiphoid process, the third electrode 9 is placed 2 inches to the right of the spine at the level of the xiphoid process, and the fourth electrode 10 is placed six inches to the right of the spine level with the xiphoid process. The advantage of placing the electrodes in this configuration is that both lungs are factored into the reading and high level of signal.

Figure 3:
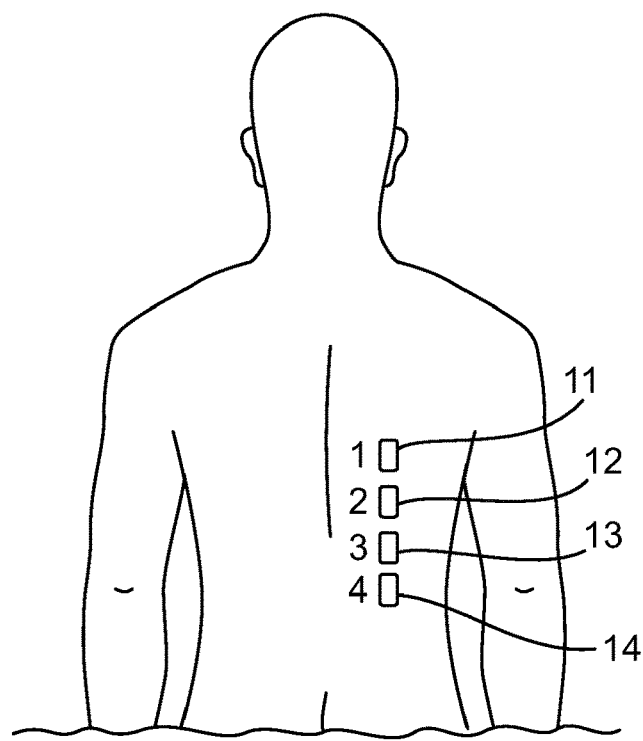
FIG. 3 is a diagram of the Posterior Right Vertical electrode configuration.

Referring to FIG. 3, there is shown the second specific electrode configuration called Posterior Vertical Right (PVR), in which the first electrode 11 is placed midway between the midaxillary line and the spine just beneath the scapula, the second electrode 12 is placed two inches beneath electrode 1, the third 13 electrode is placed two inches beneath electrode 2, and the fourth electrode 14 is placed beneath electrode 3. The advantages of this configuration are the reduction of electrode movement due to thoracic expansion and less cardiac interference. This position has the benefit of little to no volume change between electrodes and less heart noise.

Figure 4:
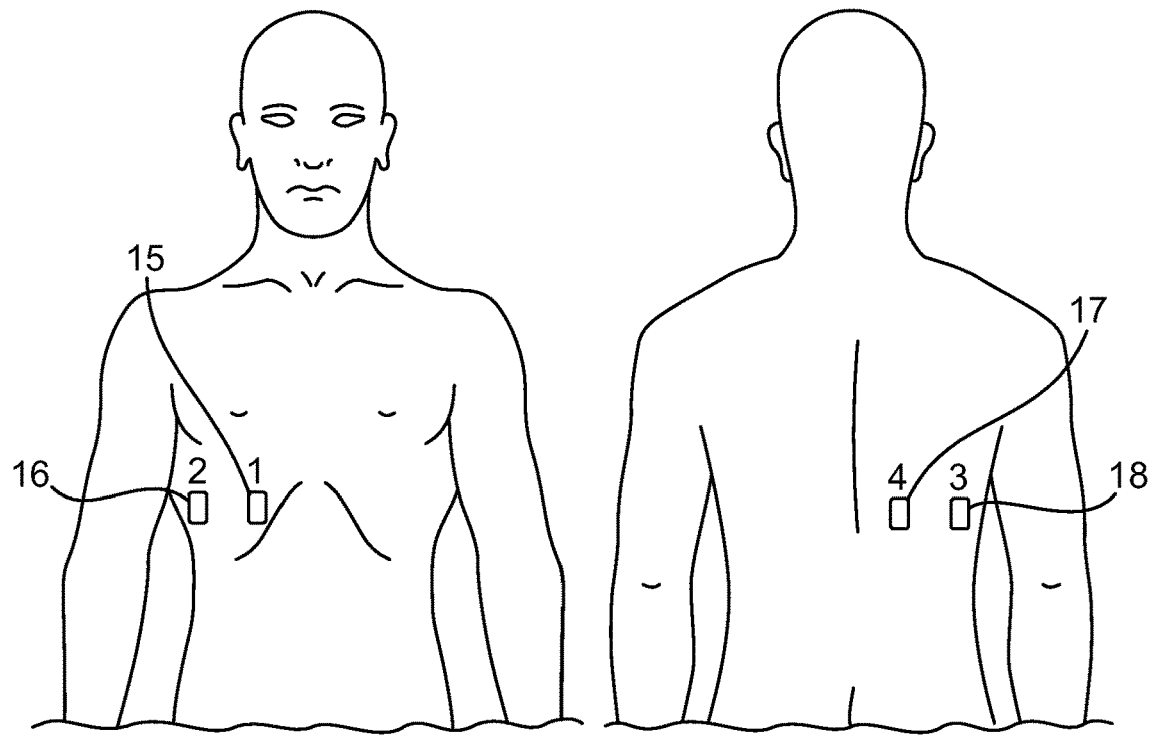
FIG. 4 is a diagram of the Anterior-Posterior electrode configuration.

Referring to FIG. 4, there is shown the third specific electrode configuration called Anterior to Posterior (AP), in which the first electrode 15 is placed 6 inches to the right of the right midaxillary line at the level of the xiphoid process, the second electrode 16 is placed 2 inches to the right of the right midaxillary line at the level of the xiphoid process, the third electrode 17 is placed 2 inches to the left of the right midaxillary line at the level of the xiphoid process, and the fourth electrode 18 is placed 2 inches to the left of the right midaxillary line at the level of the xiphoid process. This position captures the most volume change, which is useful for determination of localization of breathing.

Figure 5:
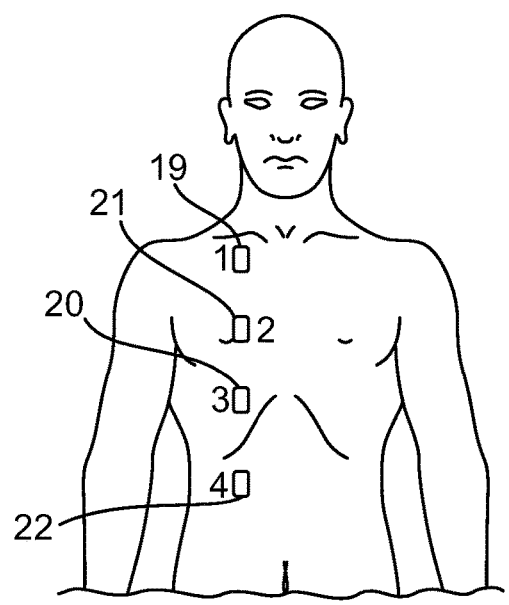
FIG. 5 is a diagram of the Anterior Right Vertical electrode configuration.

Referring to FIG. 5, there is shown the fourth specific electrode placement called Anterior Vertical Right (AVR), in which the first electrode 19 is placed immediately beneath the clavicle midway between the xiphoid and midaxillary line, the third electrode 20 is placed at the level of the xiphoid in line with the first electrode, the second electrode 21 is placed 4 inches above the third electrode, and the fourth electrode 22 is placed 4 inches below the third electrode. This position is useful for neonates and other patients whose characteristics prevent the operator from placing leads on the posterior. Other four-probe positions are placed vertically and horizontally on the abdomen and thorax, equidistant from each other or at specifically measured distances. Probe positions are also placed at physiological landmarks such as the iliac crest or third intercostal space. Probe placement on both the abdomen and thorax allows the relationship between chest and abdominal breathing to be determined. This relationship assists in diagnosis and monitoring of therapeutics.

In addition to the aforementioned four-probe configurations, these configurations can be modified to include more probes by adding probes equidistant between the positions, for example, by adding electrodes in between electrodes 1 and 2, 2 and 3, 3 and 4 in the AP configuration two inches from each electrode in line with the placement. With a large number of electrodes, they can be placed in a grid pattern equidistant from each other; this configuration will be further discussed below. Other placements for 2 or more leads include around the thorax at equidistant points at a constant height such as the xiphoid process. The specific placement for the 24 lead system is within a linear array with 12 leads equally spaced in a linear on the chest and back respectively. Such a grid or array can be implemented within a net or vest to be worn by the patient. In one embodiment, the device provides a table describing lead placement alternatives and provides a measurement device to assist in probe placement. In one embodiment, measured distances between leads are confirmed automatically by the leads which have positioning sensors and/or sensors which can determine distance from one sensor to another sensor or sensors.

Figure 6:
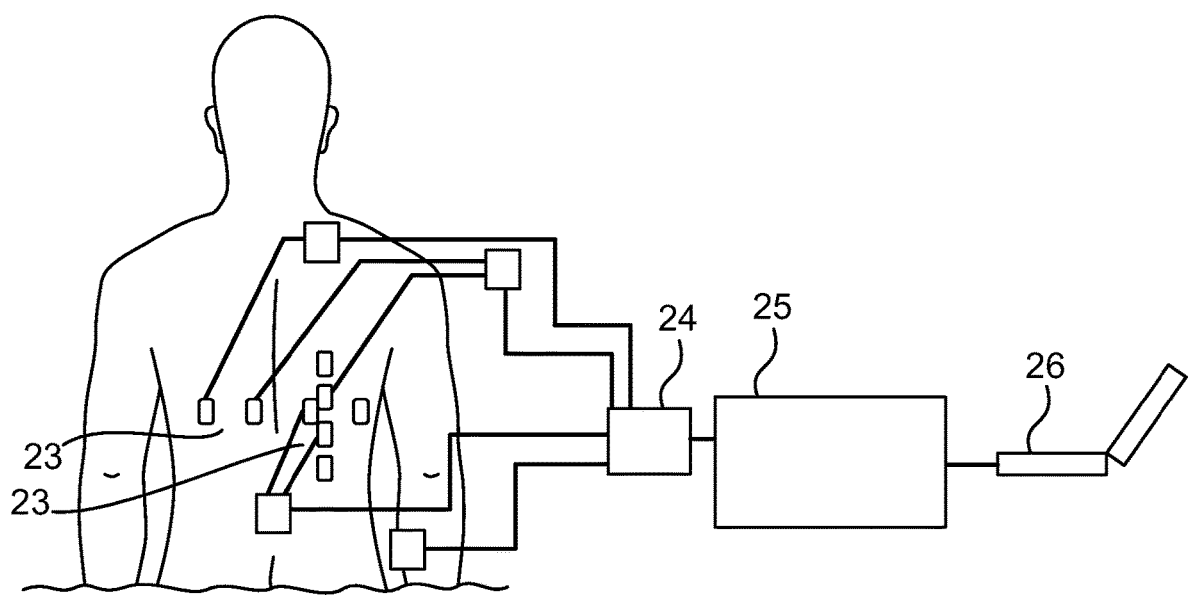
FIG. 6 is a perspective view of two four-lead configurations connected to each other by a multiplexer.

Referring now to FIG. 6, there is shown several electrode configurations 23, connected together by means of an analog multiplexer 24 and connected to a radio frequency impedance meter 25 and a programmable element 26 such as a PC. There is shown an embodiment of the device implementing the lead and multiplexor configurations shown in the previous figures, FIGS. 2 and 3. In FIG. 6, each lead is connected to several different electrodes by means of a multiplexer. The advantage of this configuration is that it allows the device to digitally switch the electronic inputs and outputs of the DAS and effectively switch the electrode configuration in order to gather data on impedance in several directions nearly simultaneously. For example, a 12-electrode system is comprised of four different sets of leads, with the first set going to the corresponding first electrode in each configuration, the second set of leads going to the corresponding second electrode in each configuration, and so forth.

Figure 7:
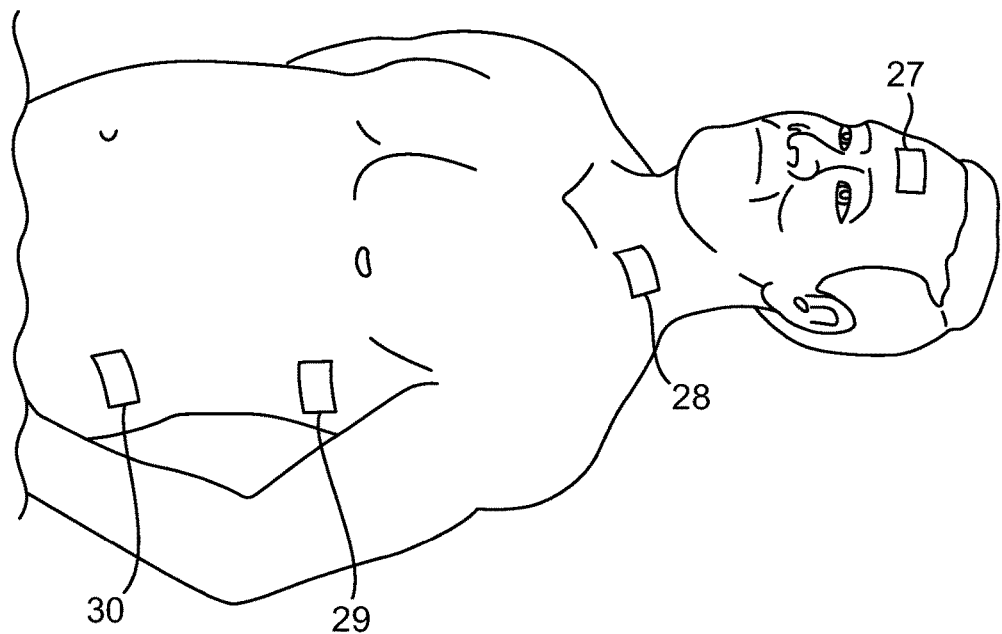
FIG. 7 is a diagram of the ICG electrode configuration.

Electrode configurations are also made to correspond with anatomic positions on the thorax, abdomen, and limbs, such as a resting ICG position shown in FIG. 7 where the first electrode 27 is place on the forehead, the second 28 above the left clavicle, the third 29 on the midaxillary line level with the xiphoid, and the fourth 30 on the midaxillary line immediately above the iliac crest.

Each electrode configuration will be affected by motion in different ways. For instance, movement of the right arm will cause a motion artifact on any lead placement which traces impedance across the right pectoral, latissimus, trapezius muscles, and other muscles of the chest and upper back. By noting differences between the shapes, derivatives or magnitudes of simultaneously recorded signals from different lead placements, local motion artifacts can be identified and subtracted from the impedance signal.

In one embodiment, the probes are manufactured in a linear strip with a delivery and sensor pair at each end and having a fixed distance between the delivery and sensor electrode to form a discrete pad. In a preferred embodiment, there is a compliant strip in-between the two pads that can be stretched to permit appropriate patient specific positioning based on anatomic landmarks. Preferably the material, once stretched, will maintain its extended configuration.

Probes

Figure 23:
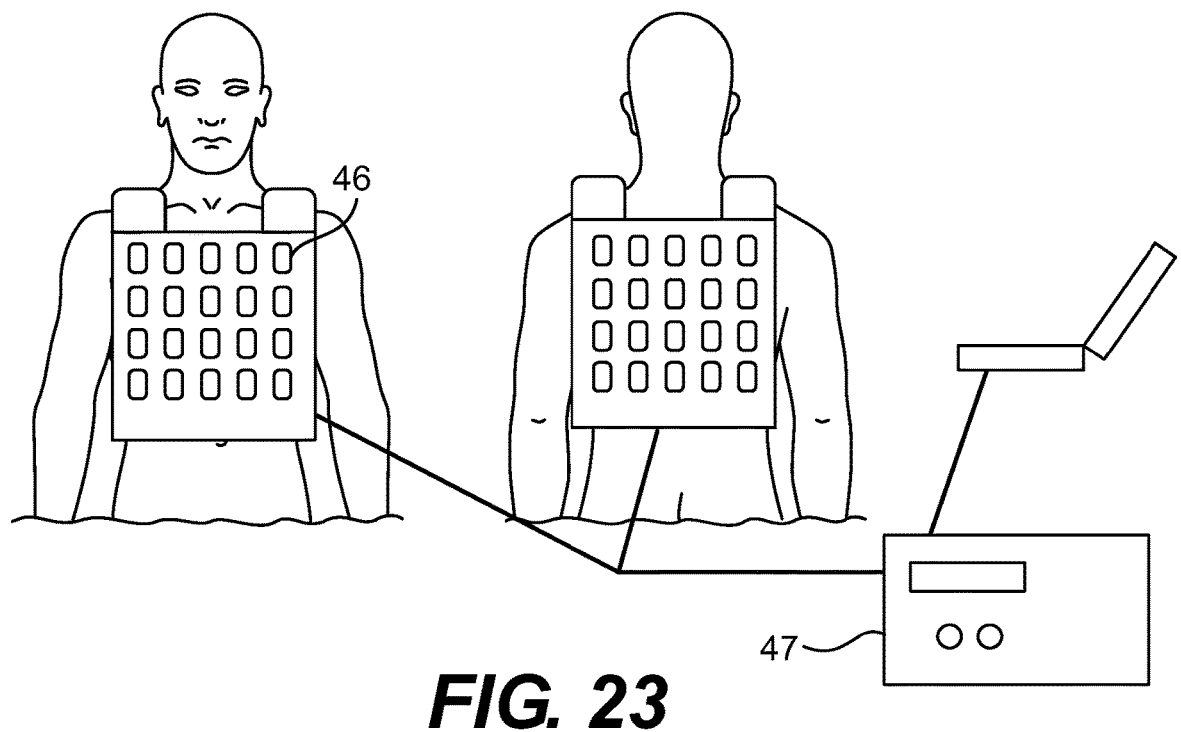
FIG. 23 is a preferred embodiment of the invention that utilizes a vest for the sensors.

Referring now to FIG. 23, there is shown an embodiment of the device in which the one or more remote probes, which are embodied as surface electrodes, speakers and/or microphones, are integrated into a vest 46 connected to an impedance plethysmograph 47 using a cable. The advantage of this embodiment is that the position of leads is determined by the manufacturer of the vest, and thus they are standardized. That is, the use of the vest eliminates operator error with respect to lead configuration. In an alternate embodiment, the probes and actuators are wireless. In an alternate embodiment, the vest also includes leads that cover the abdomen.

Figure 24:
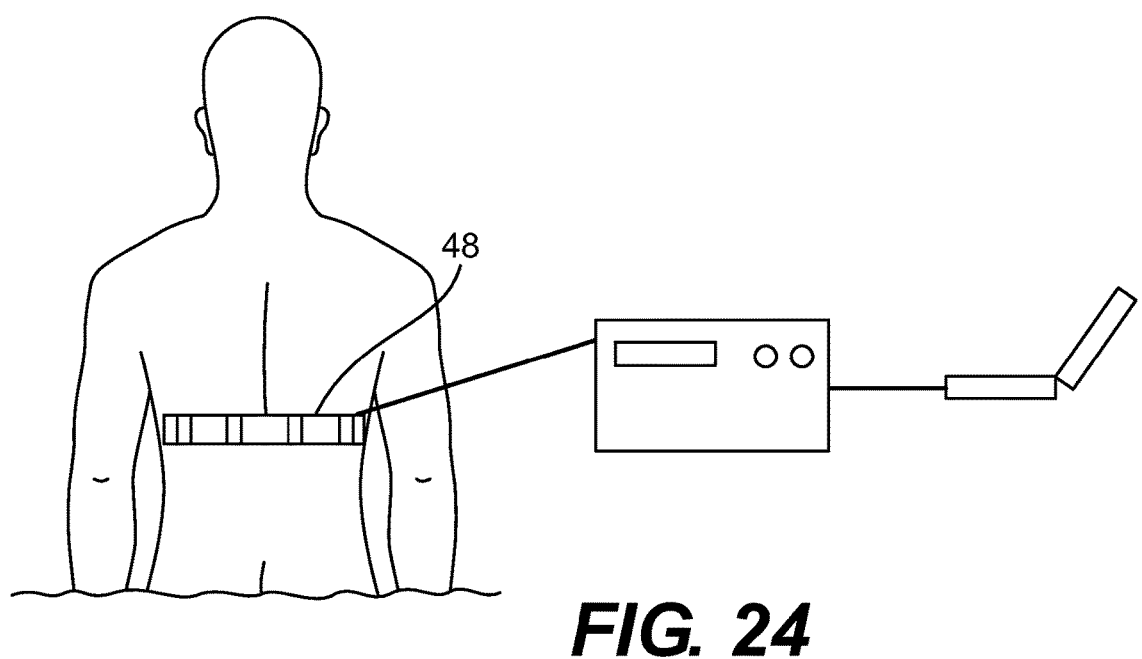
FIG. 24 is a preferred embodiment of the invention that utilizes an array built into a piece of cloth for the sensors.

Referring now to FIG. 24, there is shown an embodiment of the device in which the one or more remote probes are integrated into an array 48 where the electrodes are connected by a compliant piece of cloth or netting which is be pressed gently onto the patient's skin. The benefit of this configuration is that the inter-electrode distance is standardized by the array manufacturer, thus lessening operator dependent error with respect to electrode configuration.

Figure 25:
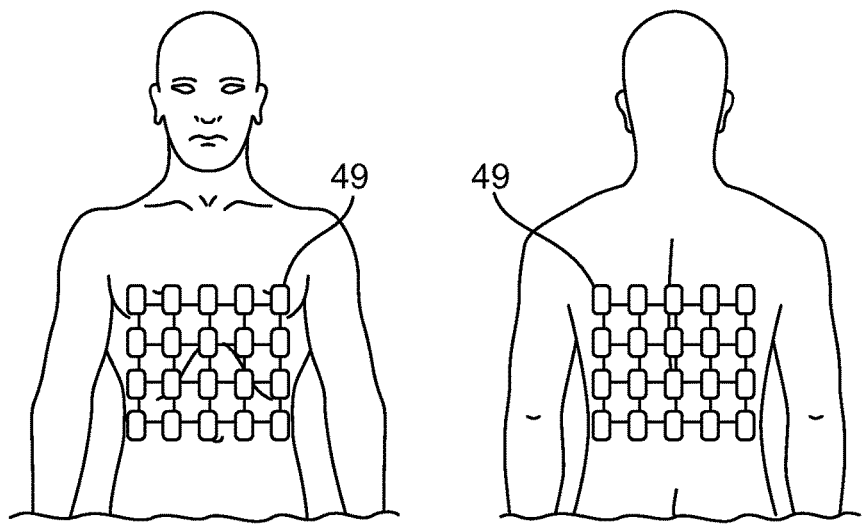
FIG. 25 is a preferred embodiment of the invention that utilizes a net of sensors.

Referring now to FIG. 25, there is shown an embodiment of the device in which the one or more remote probes are connected to each other by strings, forming a net 49 which can be applied to the patient's skin quickly and effectively. The benefit of said embodiment is that the inter-electrode distance as well as the relative positions of electrodes to one another are standardized, thus lessening the effects of operator dependent error. In another embodiment, elastic stretch of the strings provides probe adjustment for different body habitus. Preferably, the stretch material would provide a measurement of the distance either to be read on the material or by relaying information relative to stretch to the device. Preferably, the strings would have attached displacement sensors such as linear displacement transducers or strain gauges functionally connected to the programmable element to relay information about the length each string of the net is stretched. Preferably, the programmable element is further programmed to account for changes in lead placement relayed to it from the displacement sensors.

Figure 26:
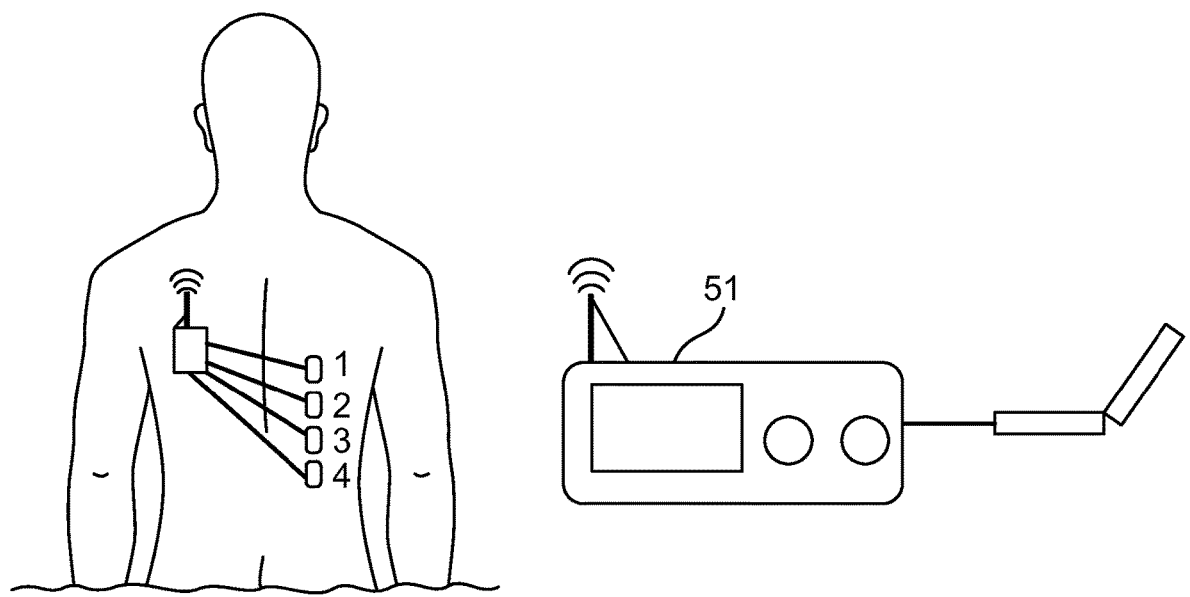
FIG. 26 is a preferred embodiment of the invention that utilizes a wireless transmitter and receiver.

Referring now to FIG. 26, there is shown an embodiment of the device in which the one or more remote probes are functionally connected to a remote transmitter 50, and in which the programmable element 51 is connected to a remote receiver. The communication protocols proposed for the system range from a limited scope to a vastly networked system of several nodes. This provides a foundation for an unlimited number of use cases. In one embodiment of the remote communication protocol a close range high frequency system such as Bluetooth v4.0 is used. This emulates a wireless solution of what a RS-232 wired connection would provide. This enables the communication of two devices in close range quickly and securely. In another embodiment a roughly 802.11 compliant protocol is used to generate a mesh network comprised of the nearest devices. This mesh network incorporates all of the devices in a given unit. The unit size is without bound since the addition of individual nodes increases the range (range and unit size are directly proportional since the network is comprised and governed by the nodes themselves—no underlying infrastructure is required). Only a vast outlier is left out of this network. This means that in order for the outlier to be omitted the nearest currently connected node must be unequivocally out of range for the outlier to communicate with. These services, specifically the hardware, are capable of running/polling without the usage of a main CPU (minimizes battery usage). This is useful because when a device is not being read it can just act as a relay node. The nature of the system minimizes power requirements (increasing longevity of service), supports asymmetric links/paths, and enables each node to play multiple roles in order to benefit the network.

Another embodiment requires connection to a LAN or WAN network, the remote procedure is catalyzed by a user-driven event (button press, etc). This generates a unique identifier, for a digital receipt of the data transaction, on each phone coupled with device specific information. This information is supplemented with a GPS location to distinguish the devices locations. Since the data transmission was initiated by both parties at a precise time, coupled with GPS information, the system is capable of securely identifying both parties by location, UID, and device identifier. All methods are secured with anonymity heuristics and encryption. This will prevent snooping of data, a problem presented by a "man-in-the-middle" attack.

Another embodiment of the device utilizes one or more electrical probes implanted in the body. In one embodiment of the invention, the implanted probes are connected to a cardiac pacemaker. In another embodiment, the implanted probes are connected to an internal automated defibrillator. In another embodiment, the implanted probes are connected to a phrenic nerve stimulator. In another embodiment the implanted probes are connected to a delivery pump for pain medication, local anesthesia, baclofen, or other medication. In another embodiment, the implanted probes are connected to another implanted electronic device. Preferably the connections are wireless.

Figure 33:
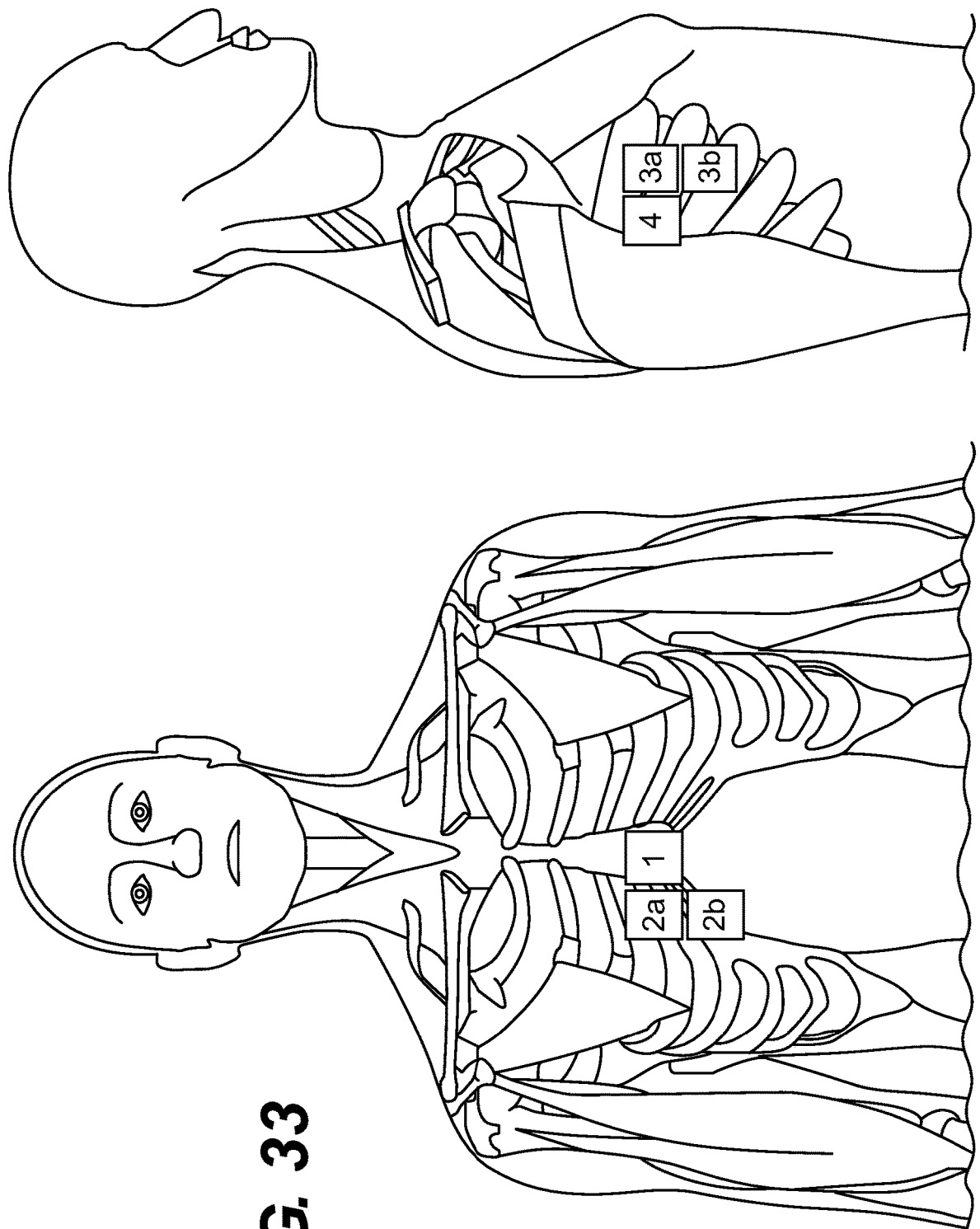
FIGS. 33-38 depict different embodiments of lead placement.

Referring now to FIG. 33, electrode configuration XidMar is show. Configuration XidMar is a two channel configuration with electrode 1 on the xiphoid process and electrode 4 on the right midaxillary line, horizontally aligned with electrode 1. Electrode 2a is 1 inch to the left of electrode 1, while electrode 3a is 1 inch to the right of electrode 4. Electrodes 2a and 3a are used to record the voltage signal on channel a. Channel b is recorded using electrodes 2b and 3b which are found 1 inch below the corresponding channel a electrodes.

Figure 34:
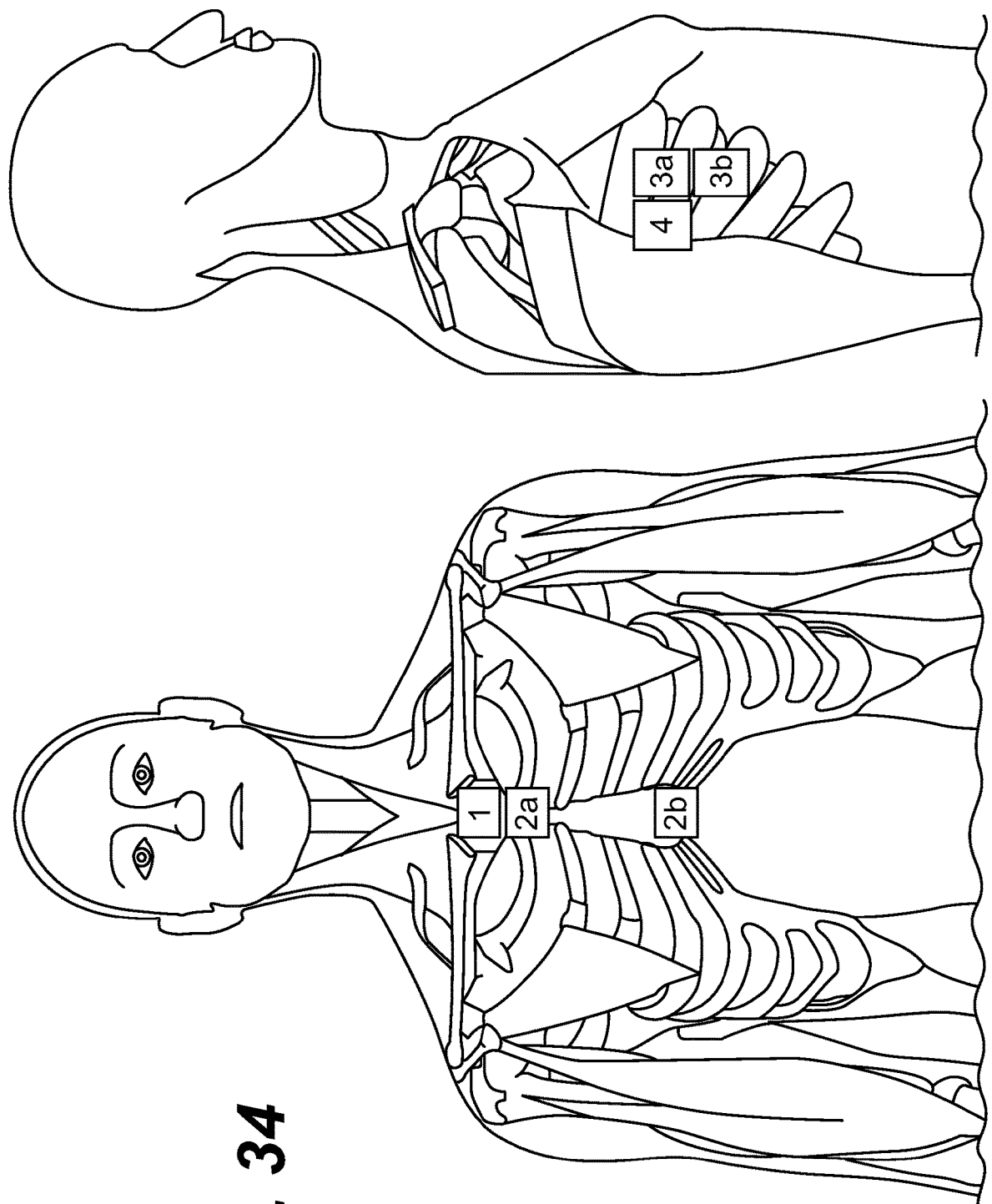

FIG. 34 shows the StnMar electrode configuration in which electrode 1 is located just below the sternal notch and electrode 4 is located on the right midaxillary line, horizontally aligned with the xiphoid process. Electrode 2a is located 1 inch below electrode 1, and electrode 3a is located 1 inch to the right of electrode 4. Channel b is at an angle approximately 45 degrees to channel a. Electrode 2b is located on the xiphoid process and electrode 3b is located 1 inch below electrode 3a.

Figure 35:
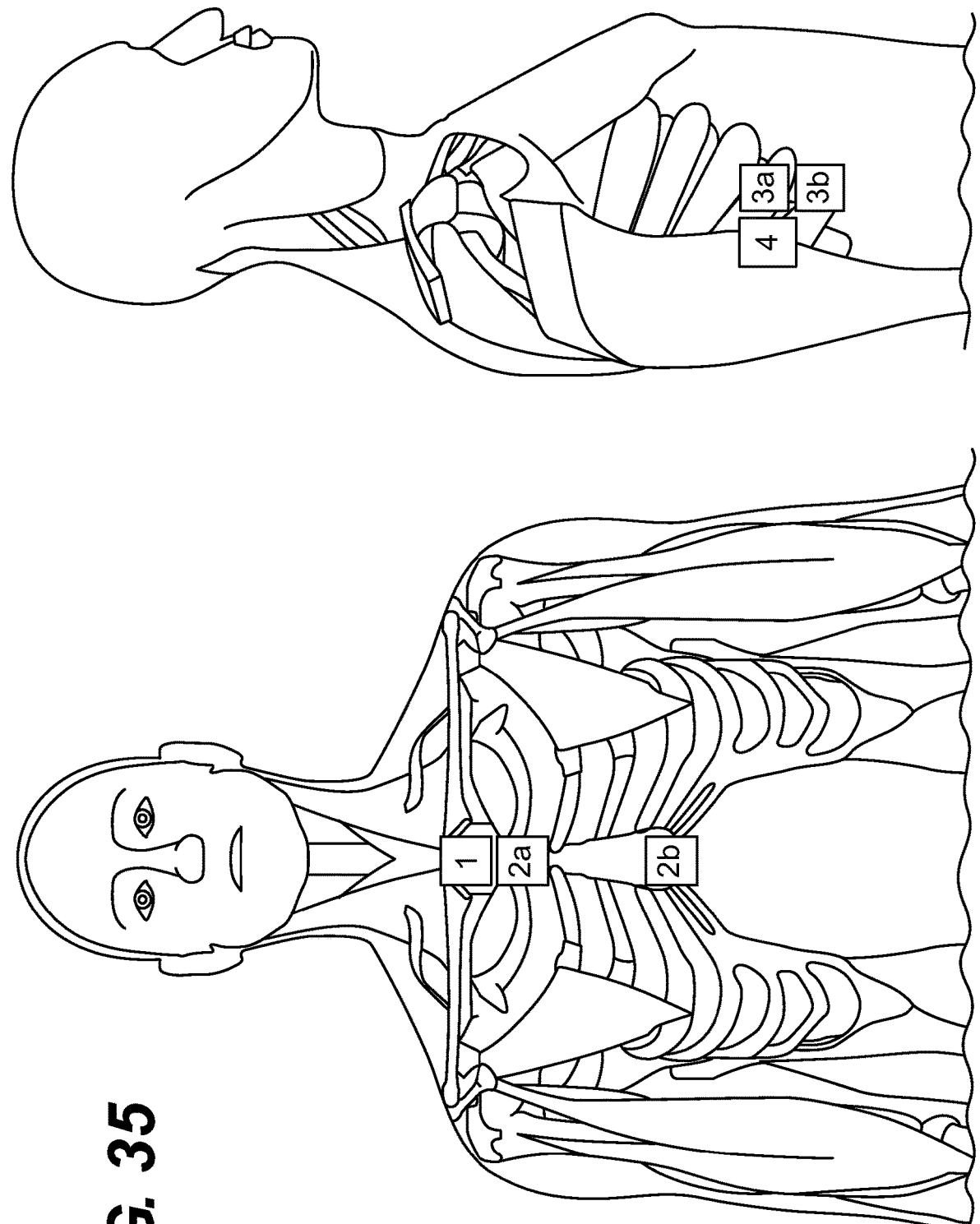

FIG. 35 shows the StnIMar electrode location in which electrode 1 is located just below the sternal notch and electrode 4 is located on the inferior right midaxillary line at the bottom of the rib cage. Electrode 2a is located 1 inch below electrode 1, and 3a is located 1 inch to the right of 4. Electrode 2b is located on the xiphoid process and electrode 3b is located 1 inch below electrode 3a.

Figure 36:
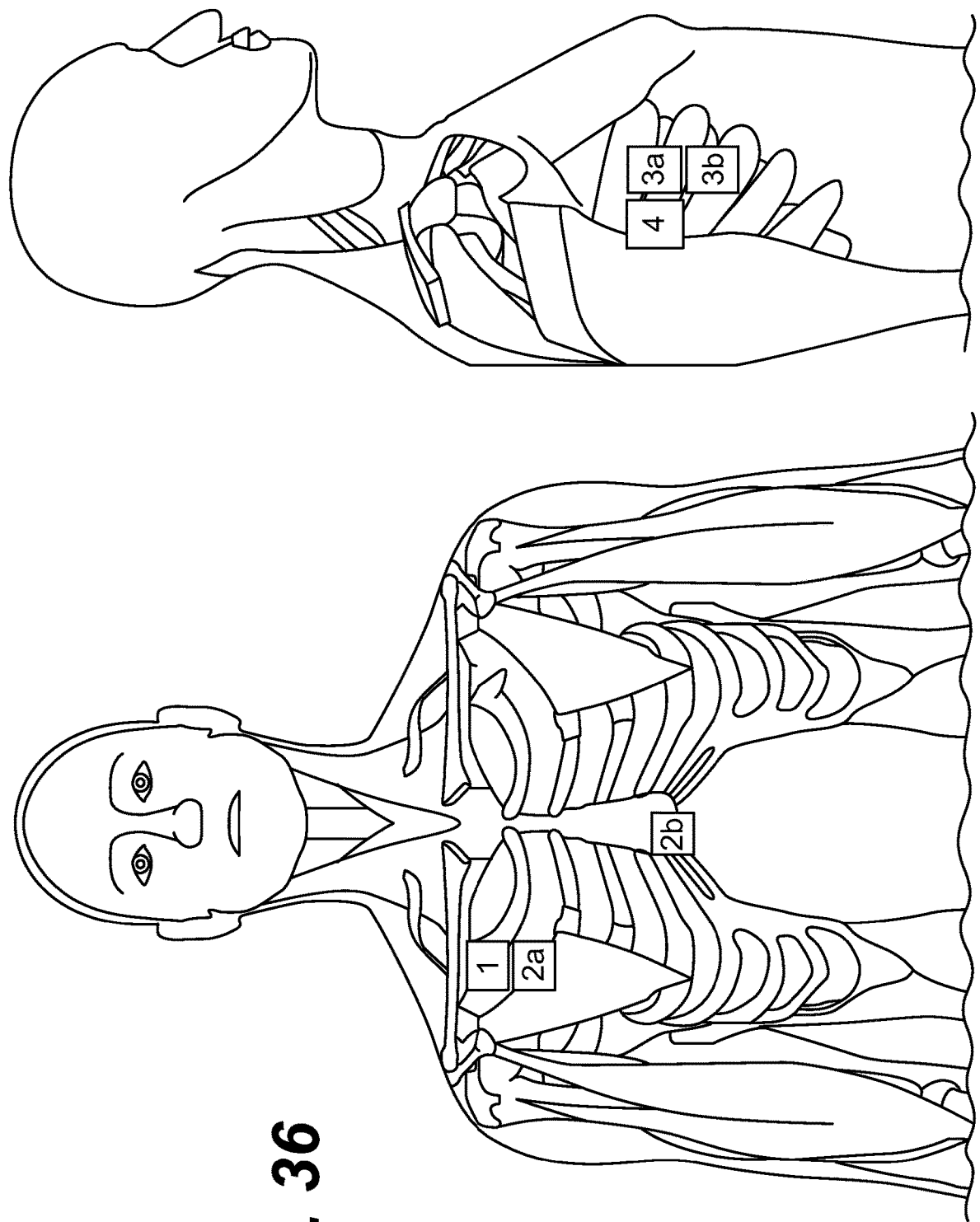

FIG. 36 shows the McrMar electrode configuration in which electrode 1 is located on the right midclavicular line just below the clavicle and electrode 4 is located on the right midaxillary line horizontally aligned with the xiphoid process. Electrode 2a is located 1 inch below electrode 1 and electrode 3a is located 1 inch to the right of electrode 4. Electrode 2b is located on the xiphoid process, and electrode 3b is located 1 inch below electrode 3a.

Figure 37:
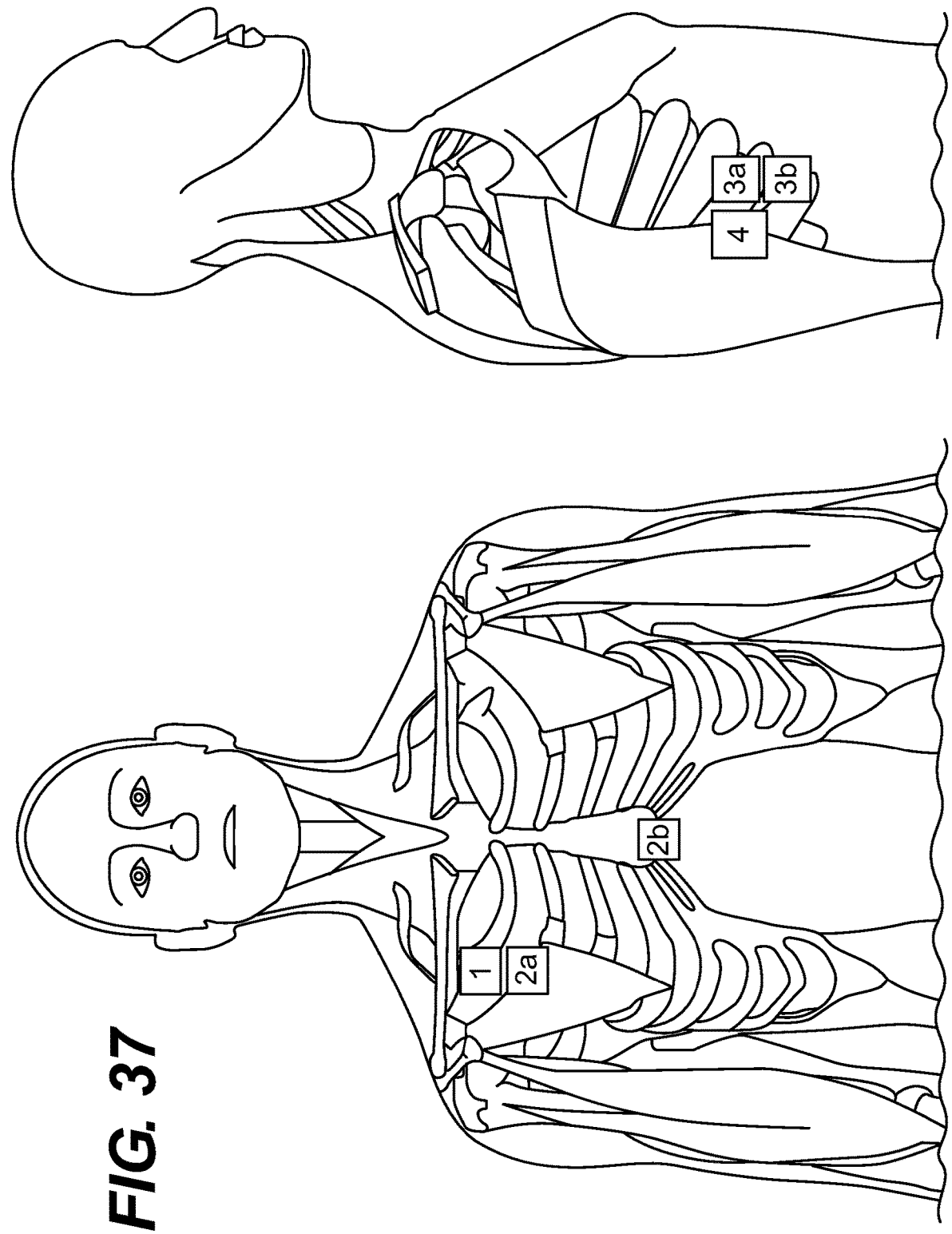

FIG. 37 shows the McrIMar electrode configuration in which electrode 1 is located on the right midclavicular line just below the clavicle and electrode 4 is located on the inferior midaxillary line approximately at the bottom of the ribcage. Electrode 2a is located 1 inch below electrode 1 and electrode 3a is located 1 inch to the right of electrode 4. Electrode 2b is located on the xiphoid process and electrode 3b is located 1 inch below electrode 3a.

Figure 38:
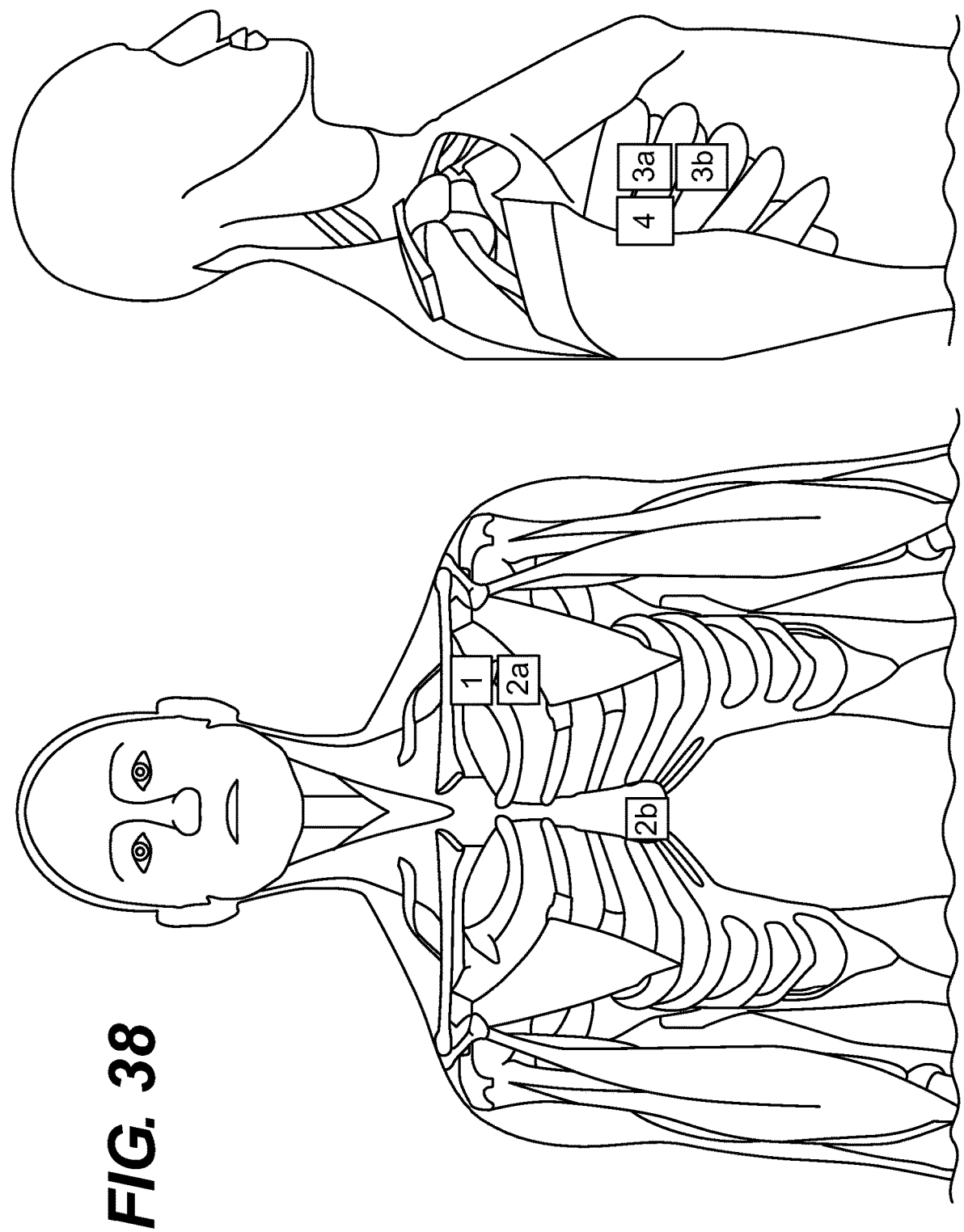

FIG. 38 shows the McIMar electrode configuration in which electrode 1 is located on the left mixclavicular line just below the clavicle and electrode 4 is located on the right midaxillary line, horizontally aligned with the xiphoid process. Electrode 2a is located 1 inch below electrode 1 and electrode 3a is located 1 inch to the right of electrode 4. Electrode 2b is located on the xiphoid process and electrode 3b is located 1 inch below electrode 3a.

The electrode configurations shown in FIGS. 34-38 can utilize either channel a, channel b, or both simultaneously to measure data.

In one embodiment of the invention, the system is adapted to perform an impedance tomography scan utilizing a one or more pairs of source electrodes and one or more voltage sensing electrodes. The scan is completed by taking a series of measurements with a movable electrode which is applied to the skin. The movable electrode forms a voltage measuring pair for impedance reading with at least one other electrode. The movable electrode may be coated in hydrogel which may be applied multiple times. In another embodiment of the invention, the electrode contains a hydrogel dispenser for each application. In this embodiment, hydrogel is stored in an internal pouch or syringe and there are devices, such as a mechanical button or squeeze tube, which allows the user to dispense hydrogel onto the electrode. In one embodiment of the device of the invention, the system directs the user to sweep the movable electrode between predetermined points on the body as indicated on the user interface or on a reference card. In another embodiment, the user may place the movable electrode from point to point and the system senses the location of the electrode using a camera, sonar, radar or other device.

The secure adhesion of electrodes is determines the quality of impedance readings. In one embodiment of the invention, the system detects the quality of adhesion and reports an index of adhesion to the user. In another embodiment, the system reports problems with adhesion if the index crosses a specific threshold. In a preferred embodiment of the invention, there are multiple voltage sensing channels arranged in a straight line. This can be accomplished using five electrodes arranged in a line. Referring to the five electrodes by letter, electrodes A and B are placed close together on one end of the line, electrodes D and E are placed close together on the other end of the line. Pair A-B and pair D-E may be placed 3-24″ apart from each other. Electrode C is placed somewhere between the two pairs. Impedance is measured on three channels, B-C, C-D and B-D. If all the electrodes are adhered well, the sum of $Z_{BC}$ and $Z_{CD}$ should be close to $Z_{BD}$. The difference between the measures, or the ratio of the difference to the full measurement can be used to determine the index of adhesion quality.

In one embodiment of the invention, Electrode C is not placed in a straight line with the other pairs of electrodes. In this case, impedance is measured on channels B-C and B-D. The ratio between the impedance on the two channels $Z_{BC}$ and $Z_{BD}$ is used to determine the index of adhesion quality. In another embodiment of the invention, the current driven through electrodes A and E is measured. The current measurement or variability in the current measurement can be used to determine the index of adhesion for electrodes A and E.

Figure 39:
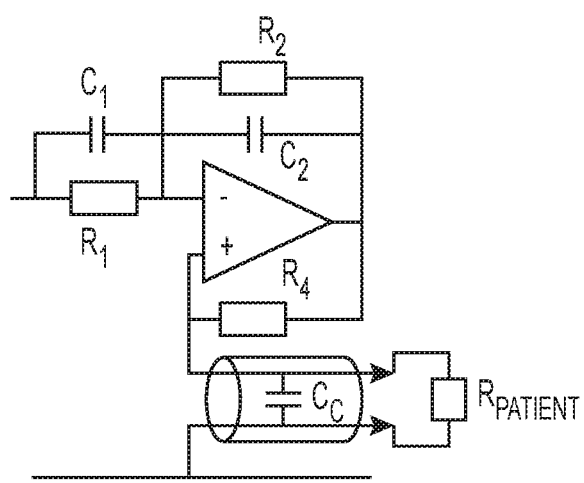
FIG. 39 depicts an embodiment of a modified Howland circuit for compensating for parasitic capacitances.

Electrical connectors have inherent capacitance which can affect impedance measurements. In one embodiment of the invention, the system compensates for the capacitance of cables, leads or other electrical connection between the impedance measuring subsystem and the patient-connected electrodes. In one embodiment, this is accomplished by an inductor within the impedance measuring subsystem. In another embodiment, a compensating inductor is integrated into a patient cable or leads which connect the impedance measuring subsystem to the patient-connected electrode pads. In another embodiment a compensating inductor is embedded into an integrated electrode PadSet. In another embodiment, a modification of a Howland circuit which consists of capacitors $C_1$ and $C_2$ with values chosen to compensate for parasitic capacitances Cc is used (see FIG. 39).

To achieve high clinical relevancy and good definition of respiratory curves, the impedance measurement subsystem should to be able to determine small variations in patient impedances on top of a relatively high baseline background with a high resolution. Therefore, there are stringent requirements on the absolute and relative impedance measurement errors. To obtain sufficient precision one or more of the following design solutions can be used: (1) the electronic design can be based on high precision/low temperature drift electronic components; (2) a high precision analog divider can be used to obtain the ratio between measured voltage and monitored source current, compensating for variations in the source current; (3) the same voltage can be used for source current generation and as an ADC reference, compensating for variations in the reference voltage; (4) external calibrated impedance standards can be used to calibrate and verify the impedance measurement subsystem performance. The calibrated system is preferably connected to the impedance standard with the same trunk cables used for patient measurements, providing verification of overall system performance. (5) The impedance measuring subsystem can have a built-in calibrated impedance standard, allowing on-site verification and recalibration. In one embodiment built-in standard is attached to the system via an external service port. The calibration is conducted by connecting the "patient" end of trunk cable back to the service port on the device and running calibration procedure available through the device's GUI. (6) The calibration can be completed by varying impedance of the built-in standard over the whole range of the measured patient impedances to derive a device model, which can be used during patient measurements to achieve high-precision results. (7) The temperature model of the device can be derived by placing the device into a thermostat and measuring drift in the measured value as a function of internal device temperature. The internal device temperature can be monitored via a built-in thermal sensor. During patient measurement, a measurement correction is calculated using the thermal sensor's reading and applied to the measured values.

Active Acoustic System

For acoustic measurement of lung volumes, preferably the device comprises at least one speaker and at least one microphone. Preferably the at least one speaker and microphone are arranged as a net, vest, or array. Preferably the at least one speaker switches between discrete frequencies or broadcasts broad spectrum noise. Preferably, numerous speakers are active simultaneously, broadcasting different acoustic signals. Preferably, numerous microphones are active simultaneously and record the measured acoustic properties of the thorax which can be correlated to lung volume as well pathologies of the lungs. Preferably, the microphones also record sounds that originate in the lungs such as wheezing, squawks, and crackles, which can be indicators of numerous chronic and acute pulmonary diseases. Preferably the lung sounds are recorded and identified as they are modified by the active signal. Preferably an algorithm analyzes the number and position of wheezes, squawks, and crackles to predict asthma and other pulmonary diseases. In one embodiment, acoustic data are combined with impedance data to help time the acoustic measurements relative to the respiratory cycle. In one embodiment acoustic data are combined with impedance data for the purposes of diagnosis or monitoring of disease. An example of this is congestive heart failure where stiffness creates characteristic changes in impedance curves and there are also changes in lung sounds associated with congestive heart failure. Combination of the data provides additional information.

Figure 20:
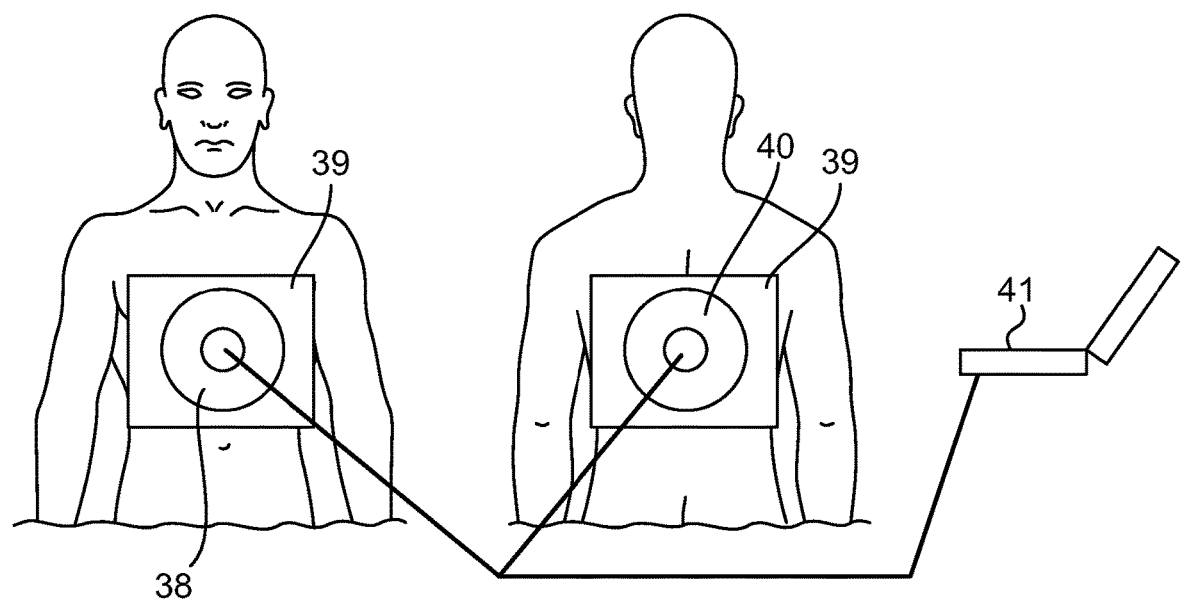
FIG. 20 is a preferred embodiment of the invention that utilizes a speaker and a microphone.

Referring now to FIG. 20, there is shown a device in which a speaker 38 is attached to the chest of a patient, and insulated with sound dampening foam 39. A microphone 40 is attached to the patient's back and is insulated with sound dampening foam. Both the speaker and the microphone are functionally connected to a programmable element 41, for example a computer with installed analysis software such as MATLAB. The output element provides data relating to the patient's respiration to the operator in real time. The speaker generates an acoustic signal which is recorded by the microphone. Signal generation and recording are timed and synchronized by the programmable element. Analysis software uses features of the recorded sound wave to evaluate the acoustic properties of the thorax, which can be used to estimate lung volume. Said signal features include but are not limited to: frequency-dependent phase shift, and amplitude attenuation. Preferably, the speaker switches between discrete frequencies of sound or generates broad spectrum white noise.

In another embodiment of the device, the microphone is also used to detect sounds which originate within the lungs such as crackles, squawks and wheezes. In one embodiment, the programmable element of the device will employ software algorithms to detect associate acoustic patterns and inform physicians. In one embodiment, the acoustic system will interface with an impedance based system as well.

Figure 21:
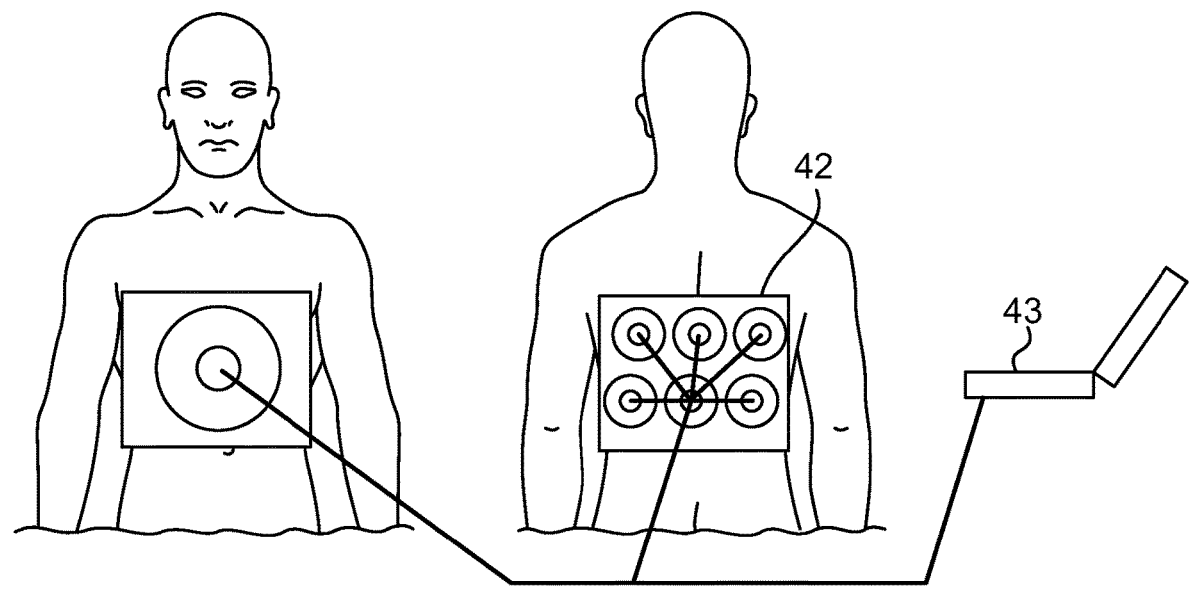
FIG. 21 is a preferred embodiment of the invention that utilizes a speaker and an array of microphones.

Referring now to FIG. 21, there is shown an embodiment of the device in which an array of microphones 42 is used to record transmitted sound from different regions of the thorax. Preferably microphones record simultaneously. Preferably, the programmable element 43 selects the microphone with the best signal to noise ratio for analysis. Preferably, the programmable element combines the data from different channels in order to maximize the accuracy of lung volume estimates and localize pathologies of the lungs including tumor formation, bleeding, and tissue degradation.

Figure 22:
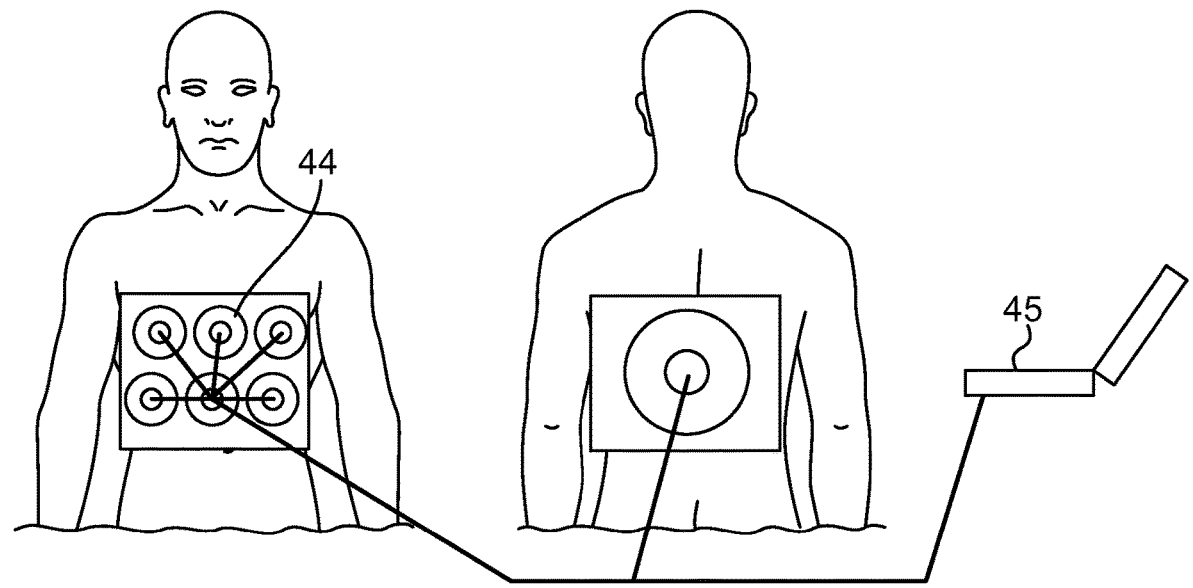
FIG. 22 is a preferred embodiment of the invention that utilizes an array of speakers and a microphone.

Referring now to FIG. 22, there is shown an embodiment of the device in which an array of speakers 44 is used to generate acoustic waves. Preferably the programmable element 45 controls each of the speakers individually, and switches between speakers to allow the device to measure acoustic properties of the thorax in many different directions. Preferably, the programmable element will activate each speaker simultaneously with signals of unique frequencies so that the signal from each speaker can be separated in the recorded signals. Preferably, the programmable element combines the data from different channels in order to maximize the accuracy of lung volume estimates and localize pathologies of the lungs including tumor formation, bleeding, and tissue degradation.

Patient Data Entry

Preferably, the device software maintains a user-friendly GUI (Graphical User Interface). Preferably, the GUI contains a color coding system to aid operators in quickly making diagnoses and decisions for patient care. In one embodiment, the GUI presents a numerical RVM measurement. In one embodiment the GUI presents a respiratory sufficiency index (RSI). In one embodiment, the GUI presents a respiratory waveform.

In the software present in all embodiments of the device, patient data is preferably recorded by the user prior to testing. The user is prompted to enter patient data. The data recorded includes any or all of the following: patient height, weight, chest circumference during maximum inspiration, chest circumference during normal end-expiration, age, gender, ethnicity, and smoking history. In one embodiment, posture when testing is also input into the device within the programmable GUI. Variations in posture may lead to different breathing patterns and tidal volumes. The device accepts posture inputs such as supine and seated and standing. The ability to test patients in multiple postures is helpful with noncompliant patients such as neonates or obtunded patients.

In one embodiment, the device calculates BMI. In a preferred embodiment, an algorithm in the device or on a look up table calculates a "calibration coefficient" that corrects for patient size and body habitus to provide a universal calibration to deliver an absolute measurement. The calibration coefficient may be obtained by combining patient information with the data recorded off the probes applied. Preferably, the physical location of the probes is also entered. During the data acquisition, the calibration algorithm may validate the data and their consistency with the patient information entered, and may suggest combination of the input parameters that is most consistent with the data recorded, as well as a suggestion for the operator to re-check the patient's information. As data is being acquired, the calibration algorithm may suggest and/or perform re-adjustment based on signal pattern recorded off probes, and/or provided by an operator as normal or abnormal. In another embodiment, the device calculates BSA or another index of body shape or size. In one embodiment, the system displays predictive values for patient results based on the aforementioned patient data. In one embodiment, the device also provides a percentage comparison against these values within displayed results to further inform the clinician of patient parameters or condition based on standard tables of spirometric data created by Knudsen, Crapo, or others. In one embodiment, the patient's demographics and/or body measurements are entered and the device suggests the lead configuration and/or the spacing of the leads and/or the size or characteristics of the lead for that patient.

In one embodiment, the device assesses signal variation and adjusts display parameters, calibration parameters and or intermediate calculations in response to the variation. In one embodiment the device assesses variation in one or more features of the signal including baseline, mean, minimum, maximum, dynamic range, amplitude, rate, depth, or second or third order derivatives of any items in the list.

In one embodiment, the device calculates a calibration coefficient to convert a raw or processed impedance trace to a respiratory volume trace. In one embodiment, the calibration coefficient is calculated from a range of physiological and demographic parameters. In one embodiment, the device of the invention automatically adjusts the calibration coefficient in response to variation in the parameters. In one embodiment, the device automatically adjusts the calibration coefficient in response to one or more of: respiratory rate, baseline impedance, or mean impedance.

In one embodiment, the device includes one or more of, respiratory rate, baseline impedance, or mean impedance in the calculation of the coefficient, or a correction factor for the calibration coefficient. In embodiments in which the calibration coefficient is based on a time-variable parameter, such as respiratory rate, baseline impedance or mean impedance, the device automatically adjusts the calibration coefficient to account for the variation in the parameter.

In one embodiment, the device adjusts the calibration coefficient based on the assessment of variation in the signal. In one embodiment where the calibration coefficient is used to convert a raw impedance signal to a respiratory volume trace, the calibration coefficient is based partially on respiratory rate.

In one embodiment, the device adjusts the display of a dataset in response to variation in the dataset. The dataset is made up of a raw signal from a sensor, a processed signal from a sensor, or the calculated metrics or parameters.

In one embodiment, the device adjusts the minimum of the y-axis on a displayed chart in response to variation in the dataset. In one embodiment, the minimum of the y-axis on a displayed chart is equal to the minimum of the dataset. In one embodiment the minimum of the y-axis on the displayed chart is equal to the minimum of the dataset within a specific window. In one embodiment, the window over which the relevant minimum of the dataset is calculated is the same as the window over which the data is displayed. In one embodiment, the minimum of the y-axis on the displayed chart is equal to the minimum of the dataset within the display window minus a coefficient or percentage of the minimum value.

In one embodiment, the device adjusts the range of the y-axis of the displayed dataset is to account for variation in the dataset. In one embodiment the range of the y-axis of a displayed dataset is equal to the dynamic range of the dataset. In one embodiment the range of the y-axis of the displayed dataset is equal to the dynamic range of the dataset within a specific window. In one embodiment, the y-axis of the displayed dataset is equal to the dynamic range of the dataset within a specific window, plus a constant, or a percentage of the dynamic range.

In one embodiment, the device adjusts the range of the y-axis of a displayed dataset based on statistics of a feature of the dataset. In one embodiment, the device sets the range of the y-axis to be equal to the mean amplitude of the signal plus the standard deviation of the amplitude of the signal within a specified window multiplied by a coefficient. In one embodiment, the device adjusts the range of the y-axis of a displayed dataset to be equal to the mean amplitude of the signal plus the variance of the amplitude of the signal within a specified window multiplied by a coefficient. In one embodiment, the device calculates the amplitude of respirations in the dataset. The device then removes outliers at the high end, low end or which have features which appear unrelated to the intended measured parameter. The device then adjusts the range of the y-axis to be equal to the mean of the amplitude of the dataset plus the standard deviation of the dataset multiplied by a coefficient.

In one embodiment, the device automatically adjusts the midpoint of the y-axis of a chart of a dataset in response to variation in the dataset. In one embodiment, the device sets the y-axis to be equal to the mean of the dataset within a specific window. In another embodiment, the device sets the y-axis to the equal to the median of the dataset within a specific window. In one embodiment, the device sets the midpoint of the y-axis to the result of a function of the statistics of the dataset.

Calibration Method

The calibration coefficient is calculated in a novel way. In the preferred embodiment, the device contains circuitry and software that automatically calibrates the device. In one embodiment, calibration is aided by data acquired through bioelectrical impedance analysis, a process which measures tissue impedance on one or more channels at various frequencies. In this embodiment, data from bioelectrical impedance analysis may be used to calculate certain characteristics of the subject including, but not limited to, hydration level, baseline impedance and body composition. A low level of hydration causes the electrical impedance of the body to be greater. A high level of fat in the body would also cause an increase in the average electrical impedance of the body, but likely a decrease in overall impedance as electricity passes through the path of least resistance. Muscle is much more vascular than fat and contains more conductive electrolytes, so a muscular patient's body would have much lower electrical impedance than a similarly size person who was not very muscular. Scaling the calibration factor based on these inputs makes it more accurate.

Calibration of the device of the invention preferably comprises predictions for respiratory rate, tidal volume and minute ventilation based on the metabolic requirements of body tissue. Predictions preferably involve multiplying the patient's measured body weight, or ideal body weight by a volume of air, or volume of air per minute required by a unit of body weight. The ideal body weight is determined from a patient's height, race, and/or age and may further be determined with one or more of the Devine, Robinson, Hamwi, and Miller formulas.

In one embodiment, the calibration coefficient is calculated from a patient's demographic information, including but not limited to: sex, age, and race. In another embodiment, the calibration coefficient is calculated from a patient's physiological measurements including but not limited to body type, height, weight, chest circumference measured at different points of the respiratory cycle, body fat percent, body surface area, and body mass index. In another embodiment the calibration coefficient is calculated based on the measured value of the ECG signal recorded at different points. In more detail, the ECG is recorded by electrodes at various locations on the thorax and abdomen. In one embodiment, the differential voltage recordings at different electrodes are used to calculate the average baseline impedance and estimate the resistivity of the patient's thorax in various directions. In another embodiment the calibration coefficient is calculated based on the patient's baseline impedance to an external current source as measured between electrodes in a bipolar configuration, tetrapolar configuration or other configuration comprising 2 or more leads. The locations of these electrodes are placed in a range of configurations over the whole body. In another embodiment, demographic characteristics are combined with baseline impedance measurements for calibration. In another embodiment anatomic information is combined with baseline impedance measurements for calibration. In a preferred embodiment, known volumes recorded on a spirometer or ventilator are combined with demographic information and baseline impedance. In such embodiments, the system may simultaneously measure impedance and volume (using a spirometer, ventilator, or other similar device). The system then computes a specific transformation between impedance and volume as an input to the conversion algorithm In another embodiment, a dynamic calibration based on additional parameters obtained using the impedance measuring subsystem and consisting of overall patient impedance (including skin and fat layer impedances), internal organs impedance (baseline impedance) and its variations, and the shape of the respiratory curve is implemented.

Ongoing or intermittent checks of calibration are preferably undertaken. In a preferred embodiment of the device, calibration is recalculated with the recording of each sample. In another embodiment, the device is regularly recalibrated based on a timer function. In another embodiment, the device is recalibrated whenever the baseline impedance varies from the baseline by a certain threshold such as 10%. In another embodiment, the device is recalibrated whenever tidal volume or minute volume varies from baseline levels or predicted levels by a certain threshold, such as 20%, where predicted values are calculated using the formulas published by Krappo, Knudson, and others.

Ongoing or intermittent checks of calibration may be undertaken. Preferably this involves an internal check to internal phantom.

Preferably ongoing or intermittent checks of baseline impedance are be used to recalibrate or reaffirm calibration. Preferably ongoing or intermittent readings from each hemithorax individually or in combination are used to recalibrate or provide data for recalibration.

Preferably, recalibration is performed automatically or by alerting a caregiver of required modification or requiring additional steps to be taken by the caregiver, such as recalibrating with a ventilator or spirometer.

In one embodiment calibration is done through measurement electrode pairs. In another embodiment, calibration is done through additional electrodes. In another embodiment, calibration is done all or in part by repurposing measurement electrodes and using the sensor as the delivery electrodes and the delivery electrodes as the sensor electrodes.

Preferably the calibration electrodes are placed in specific locations and/or at specific distances apart on the abdomen and thorax. In another embodiment, one or more of the leads are placed a specified distance apart on the forehead. In another embodiment of the device, the magnitude of the ICG signal across an acceptable electrode configuration with or without an estimation of the heart volume is used to determine the baseline impedance and calibrate the RVM data to respiratory volume. Preferably the calibration coefficient is calculated using a combination of the 5 previously mentioned methods.

Universal Calibration

While relations between respiratory and impedance variations are highly linear, the "scaling factor" between those values vary significantly from one patient to another. There is also day-to-day variation for the same patient. The day-to-day variations are correlated to some extent with physiological parameters measured by the RMV device and can be significantly compensated for. The residual day-to-day variations for the same patient are smaller than typical measurement error. In a preferred embodiment, this residual variation can be managed with existing ancillary measurements. In a preferred embodiment, this residual variation can be managed using ongoing or intermittent recalibration by any of the methods previously described.

In one embodiment, the "scaling factor" varies between patients by about an order of magnitude. In a preferred embodiment, this factor can be determined precisely by preliminary calibration with a spirometer or ventilator data or other data set. In a preferred embodiment, the RMV device is used for measurement of respiratory parameters without preliminary calibration. Preferably, a reliable procedure of deducing this factor from measurable patient physiological parameters is used for calibration. Such procedure allows the determination of the "scaling parameter" with sufficient precision to satisfy measurement requirements for all proposed device applications.

In one embodiment, measurements of respiratory motion derived from a technology including impedance plethysmography, accelerometers placed on the body, video images, acoustic signals or other means of tracking motion of the thorax, abdomen or other body parts is calibrated or correlated with another technology that assesses respiratory status. In a preferred embodiment, respiratory motion detection derived from impedance measurements is calibrated with spirometry. In one embodiment respiratory motion detection is calibrated or correlated with end tidal CO2 measurements. In one embodiment, respiratory motion detection is calibrated or correlated with ventilator measurements of flow and/or volume. In one embodiment, respiratory motion is calibrated with a full-body plethysmograph. In one embodiment, baseline RVM measurements of a given patient are taken in conjunction with standard spirometry measurements and a calibration coefficient for that particular patient is derived. Later in the postoperative period or otherwise, the calibration coefficients are used to obtain quantitative lung volume measurements for that patient. In a preferred embodiment, such calibration coefficients are combined with current baseline impedance or other physiologic measurements for ongoing or intermittent calibration. In one embodiment, preoperative measurements are used to derive a calibration coefficient which is then used, alone or in combination with other data, to obtain quantitative lung volume measurements to use in management of the patient after surgery or in other situations. In another embodiment, the calibration coefficient is derived from lung volume or flow measurements obtained on an intubated patient from measurements recorded from a mechanical ventilator.

Preferably the device is linked to a spirometer, ventilator or pneumotachometer to provide volume or flow calibration. Preferably, the device is linked to a spirometer or ventilator or pneumotachometer to provide volume calibration. In one embodiment, the operator will run the patient through a brief breathing test regimen of one or more of the following: at least one tidal breathing sample, at least one forced vital capacity (FVC) sample, at least one measurement of minute ventilation sample, and at least one maximum voluntary ventilation (MVV) sample. The device will be calibrated based on the results of the spirometer tests relative to the impedance measurements. In a preferred embodiment, calibration will be implemented from measurements taken during tidal breathing. In particular, for patients who are unable to comply with the procedure, a simple tidal breathing sample will be taken, which requires no coaching or compliance. The tidal breathing sample is collected over 15 seconds, 30 seconds, 60 seconds, or another time frame.

In one embodiment, a calibration coefficient for a given individual is calculated based on combined spirometry and RVM data and applied to deliver an absolute volume measurement for RVM measurements taken at a future time. Preferably, this absolute volume measurement will be validated or modified at the future time using calibration capabilities intrinsic to the hardware and current measurements derived from the device. In a preferred embodiment, an algorithm is applied to RVM data based on patient demographics, existing normal spirometry data for varying patient demographics found in the work of Knudsen, Crapo, and others and/or other anatomic or physiologic measurements to provide a universal calibration to deliver absolute volume measurements without the need for individual calibration with a spirometer or ventilator.

Preferably, the device may be used in conjunction with ECG or ICG data to produce further calibration of impedance data by utilizing parameters derived ECG and ICG such as heart rate and SNR. Preferably, ECG or ICG data will help validate proper electrode placement. In another embodiment, the electrical activity of the heart is used to enhance the device calibration. Preferably the device can measure the following cardiac, pulmonary and other physiology parameters and features: Heart Rate (HR), baseline impedance, impedance magnitude, Pre-ejection Period (PEP), Left Ventricular Ejection Time (LVET), Systolic Time Ration (STR), Stroke Volume (SV), Cardiac Output (CO), Cardiac Index (CI), Thoracic Fluid Content (TFC), Systolic Blood Pressure (SBP), Diastolic Blood Pressure (DBP), Mean Arterial Pressure (MAP), Mean Central Venous Pressure (CVP), Systemic Vascular Resistance (SVR), Rate Pressure Product (RPP), Heather Index (HI), Stroke Volume Index (SVI), and Waveform Accuracy Value (WAV). Baseline values calculated from patient characteristics for these features are utilized to derive the calibration coefficient as well as calculate an index of overall respiratory sufficiency. Conversely, RVM data can be used to enhance accuracy or utility of ICG data such as Heart Rate (HR), baseline impedance, impedance magnitude, Pre-ejection Period (PEP), Left Ventricular Ejection Time (LVET), Systolic Time Ration (STR), Stroke Volume (SV), Cardiac Output (CO), Cardiac Index (CI), Thoracic Fluid Content (TFC), Systolic Blood Pressure (SBP), Diastolic Blood Pressure (DBP), Mean Arterial Pressure (MAP), Mean Central Venous Pressure (CVP), Systemic Vascular Resistance (SVR), Rate Pressure Product (RPP), Heather Index (HI), Stroke Volume Index (SVI), and Waveform Accuracy Value (WAV).

In particular, for patients who are unable to comply with a more complicated procedure, a simple tidal breathing sample of respirations at rest is taken, which requires no coaching or compliance. Analysis of these data provides information relative to pulmonary physiology and respiratory status that could not otherwise be obtained.

Figure 8:
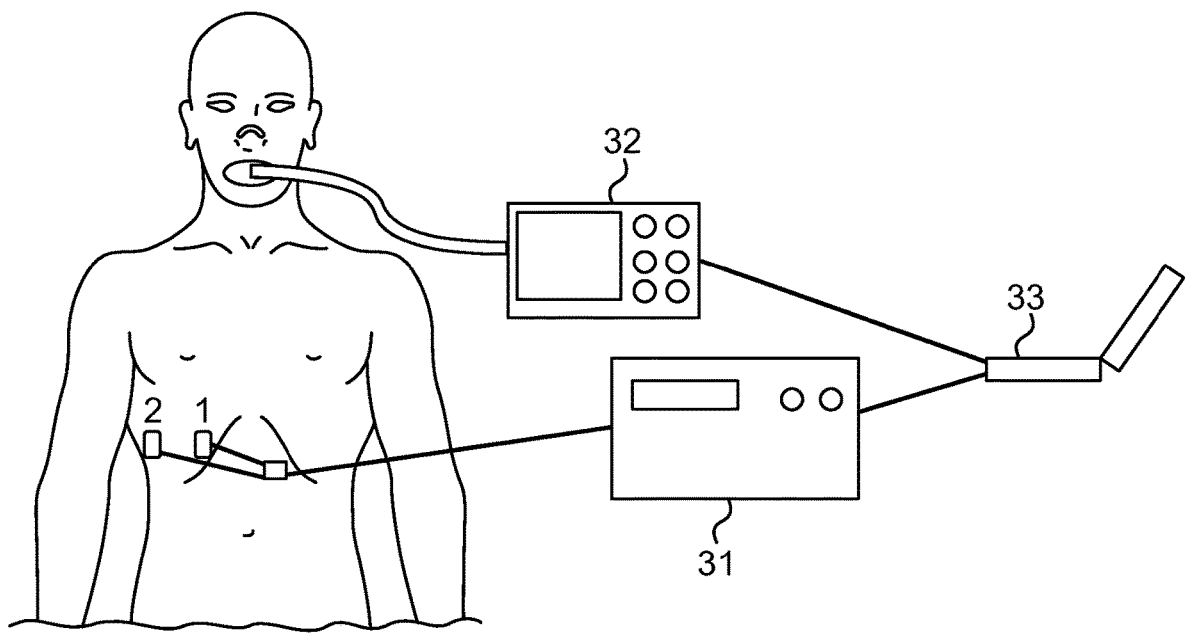
FIG. 8 is a perspective view of a four-lead embodiment of the invention connected to a spirometer.
Figure 9:
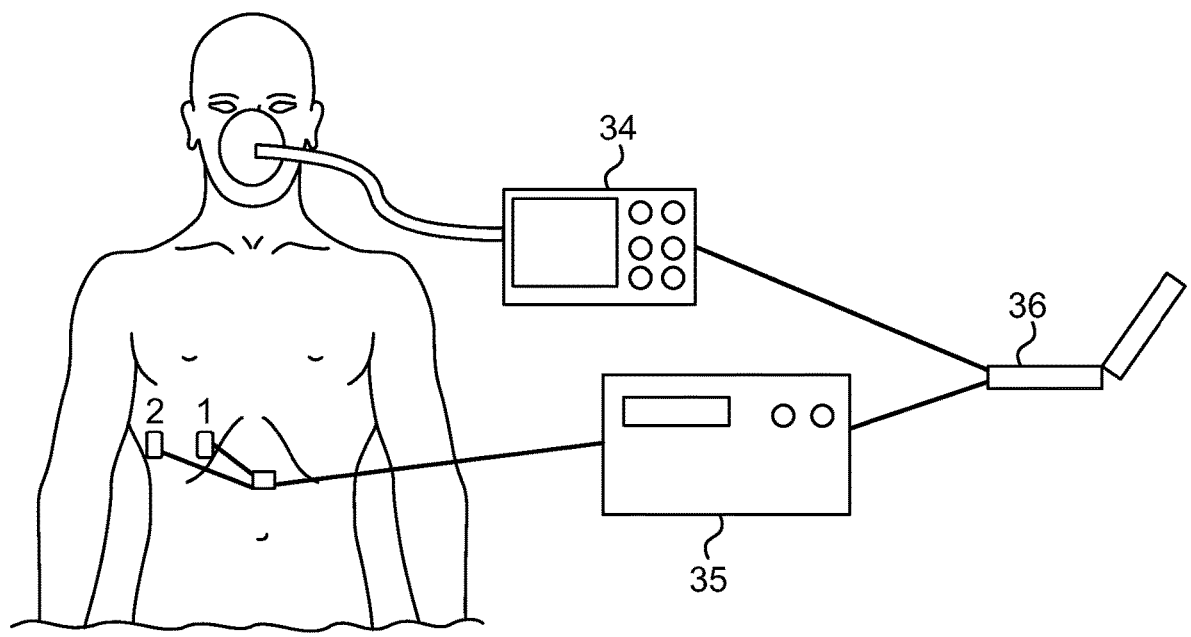
FIG. 9 is a perspective view of a four-lead embodiment of the invention connected to a ventilator.
Figure 10:
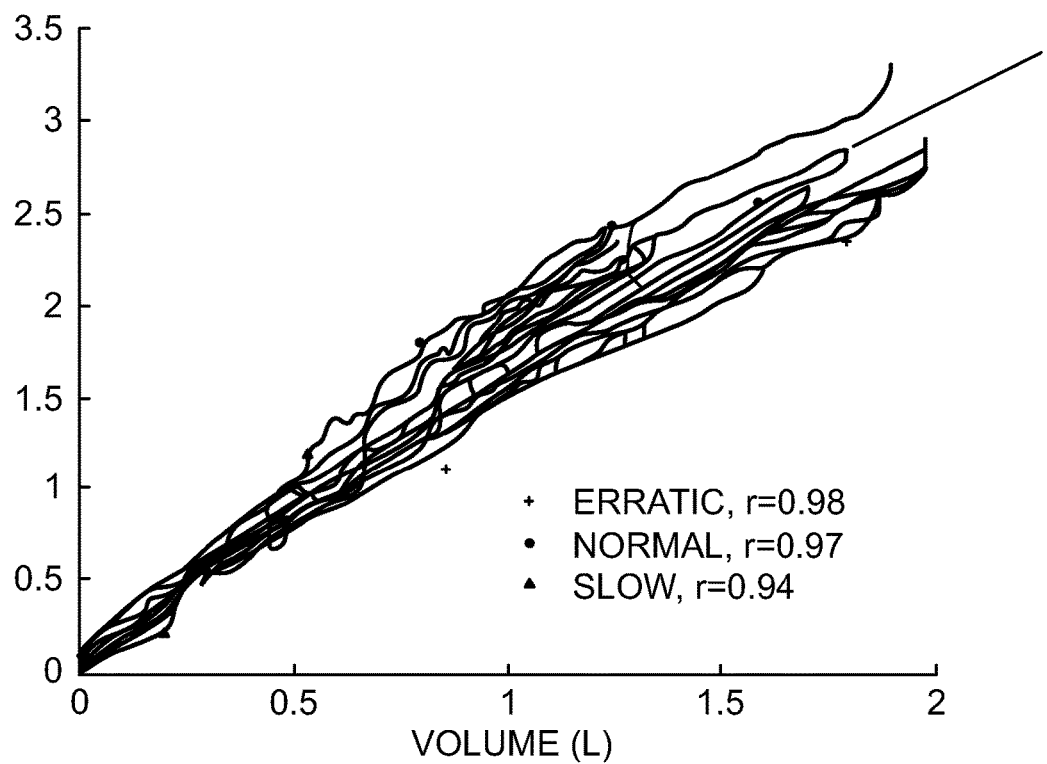
FIG. 10 is an RVM measurement (impedance) versus volume plot for slow, normal, and erratic breathing maneuvers.
Figure 11:
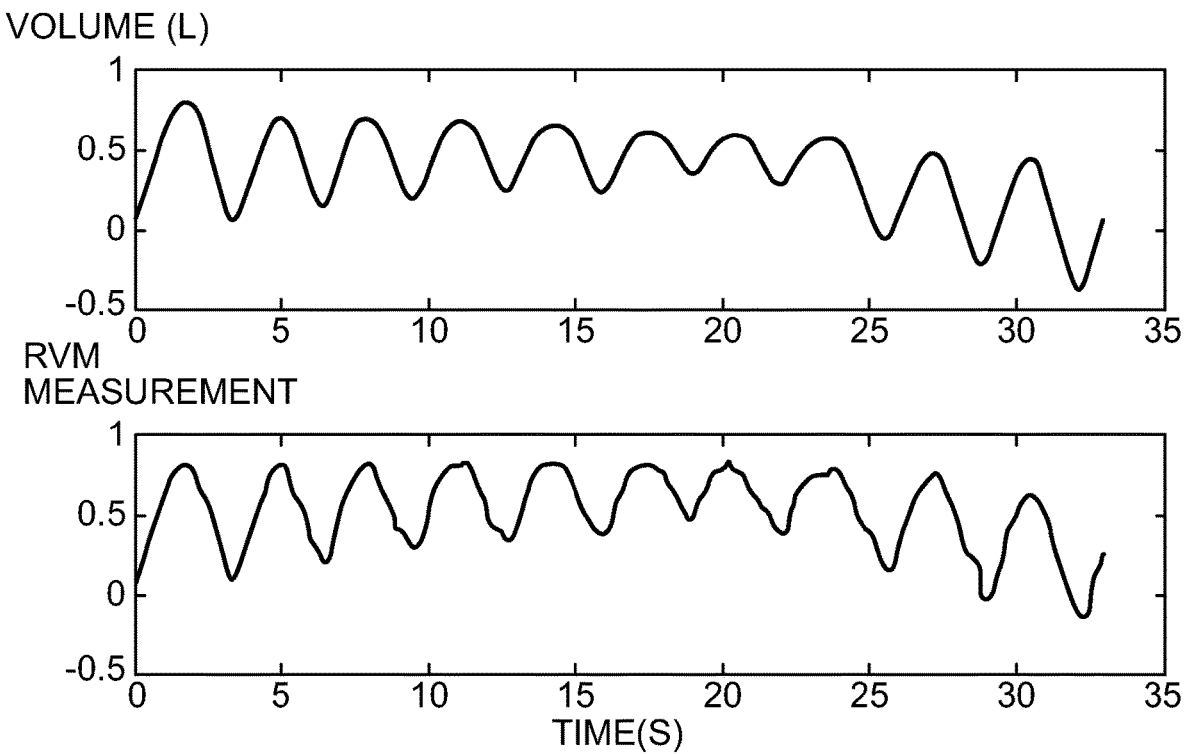
FIG. 11 is a set of RVM and volume plots against time for normal breathing.
Figure 12:
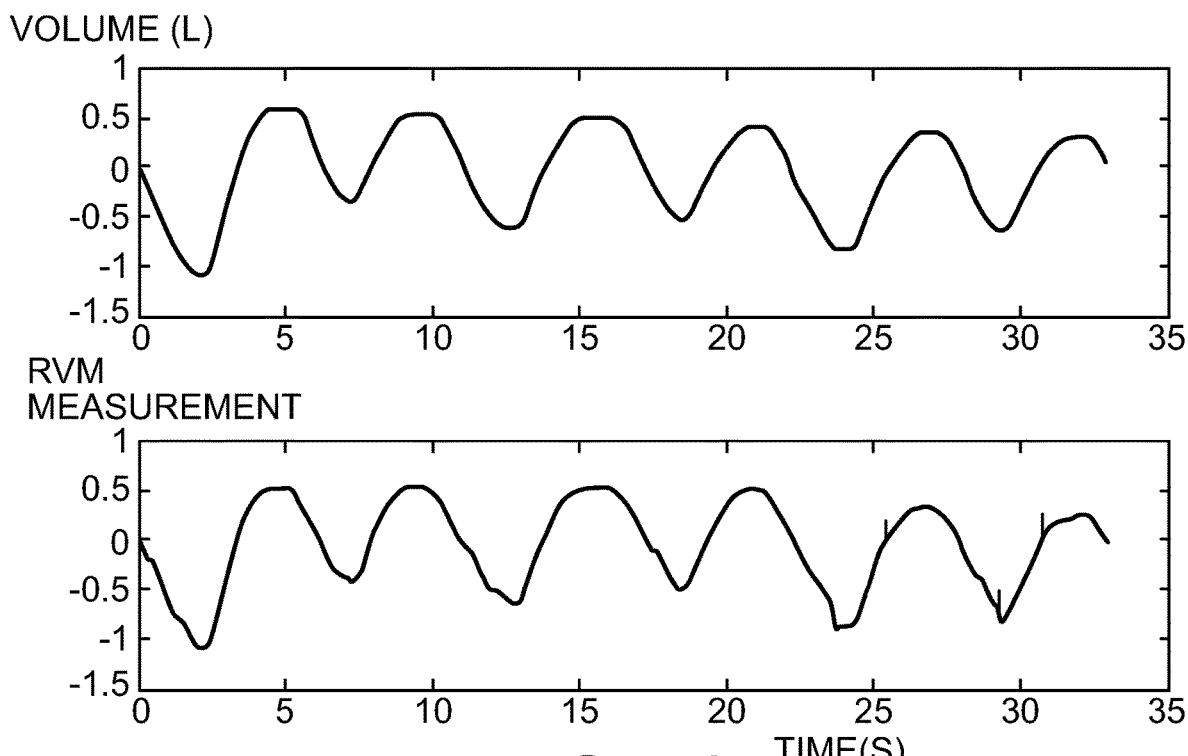
FIG. 12 is a set of RVM and volume plots against time for slow breathing.
Figure 13:
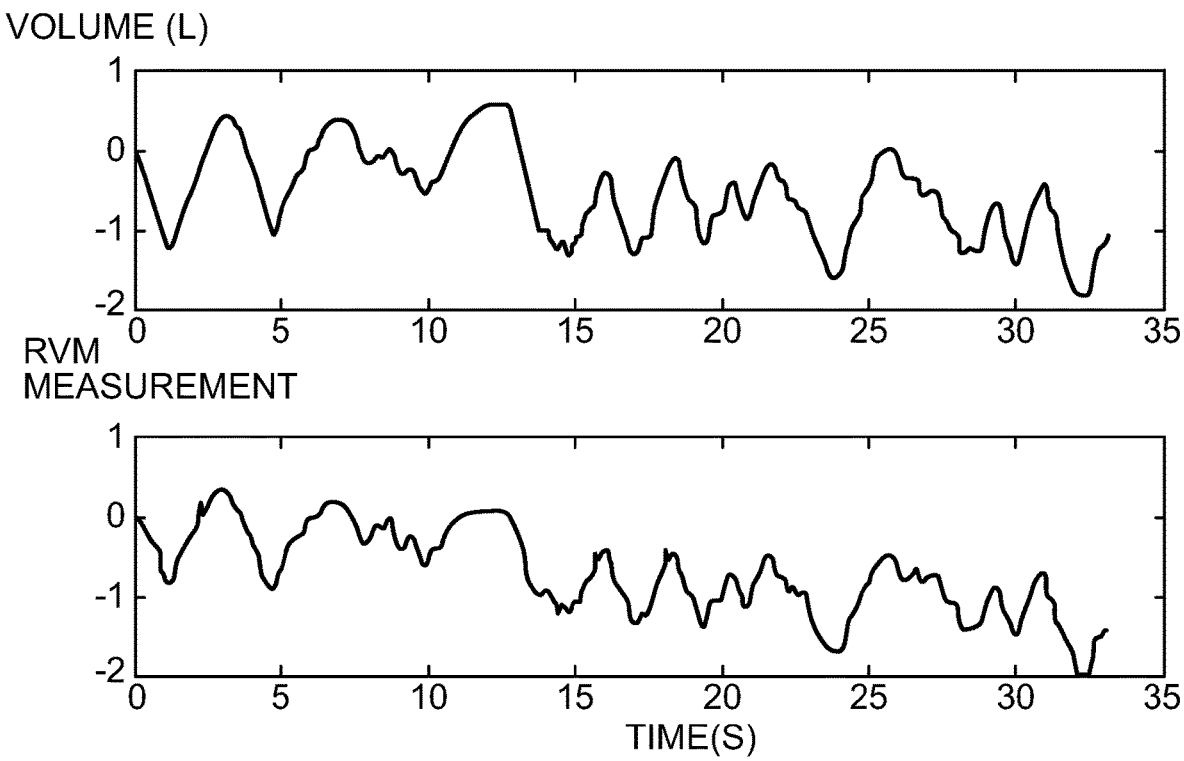
FIG. 13 is a set of RVM and volume plots against time for erratic breathing.

Referring now to FIG. 8, there is shown an impedance plethysmograph 31 and a spirometer 32 both functionally connected to the same programmable element 33. Volume data from the spirometer is preferably sampled simultaneously or nearly simultaneously with the impedance reading of the impedance plethysmograph. Referring now to FIG. 9, there is shown a patient who is connected to a ventilator 34 as well as the impedance plethysmograph 35, both functionally connected to a programmable element 36. The volume of the ventilator is sampled simultaneously with the impedance reading of the impedance plethysmograph. Referring now to the graph in FIG. 10, there is shown a graph of volume versus impedance for a given patient undergoing various breathing maneuvers while data was simultaneously collected using the impedance plethysmograph and a spirometer. The trace represented by FIG. 11 with volume over time is normal breathing. The trace represented by FIG. 12 is slow breathing and the trace represented FIG. 13 is erratic breathing. In one embodiment, the slope of the line of best fit 37 is used as the RVM calibration coefficient to compute volume from impedance. In another embodiment, an algorithm utilizing the slope, shape and/or other curve characteristics and/or other demographic or body habitus characteristics of the patient is used to calculate the calibration coefficient.

In one embodiment a simple numerical value is obtained from a ventilator or spirometer for tidal volume or minute ventilation for use in calibration of the device. One embodiment is comprised of a combined system in which RVM and volume measurements are taken simultaneously, nearly simultaneously, or sequentially by means of a spirometer, pneumotachometer, ventilator or similar device and the combined data utilized to create an individual calibration coefficient for the calculation of absolute volume from RVM measurements for a given individual.

Example:

One method of calibration has already been utilized in a small-scale study. Measurements of height, weight, chest circumference at maximum inspiration and normal expiration, distance from suprasternal notch to xiphoid, distance from under mid-clavicle to end of rib cage in midaxillary line, distance from end of rib cage to iliac crest in midaxillary line, and abdominal girth at umbilicus were taken and recorded. Electrodes were positioned at the Posterior Left to Right, Posterior Right Vertical, and Anterior-Posterior, and ICG configuration discussed above. The four probes of the impedance measurement device were connected to the electrodes that corresponded to one of the configurations above. The ICG position was connected first and only used to measure resting ICG of the subject in a supine position. The leads were then reconfigured to connect to the Posterior Left to Right position. Once the leads were positioned correctly and the subject was supine, the subject performed breathing tests which were measured simultaneously by the impedance measurement device and a spirometer for a sampling time of about 30 seconds. The breathing tests performed were normal tidal breathing (3 runs), erratic breathing (2 runs), slow breathing (2 runs), Forced Vital Capacity (FVC) (3 runs), and Maximum Ventilatory Volume (MVV) (2 runs). FVC and MVV were performed according to ATS procedures. Normal, erratic, and slow tests were measured by a bell spirometer, and FVC and MVV were measured by a turbine spirometer. Preferably, the calibration can be run all together on any type of spirometer that meets ATS standards. Once all breathing tests were complete, the leads were repositioned to a new configuration, and the tests were run again until all configurations had been tested. The data was collected on PC for the impedance data and turbine spirometer data, and on another PC for the bell spirometer data. The data was then merged onto one PC and loaded into MATLAB. Preferably, MATLAB or other software packages that utilize signal processing are used. Preferably, the data is loaded onto a PC or other computing station. Once the data was merged, the impedance and volume data from each breathing test were matched together using a GUI-based program. Correlation coefficients and calibration coefficients were produced for each of the test runs by comparing the impedance and volume traces using MATLAB. This data then was utilized in Excel to predict calibration coefficients based on patient characteristics. Preferably, the data can be imported into and analyzed in any software with a statistical package.

Figure 14:
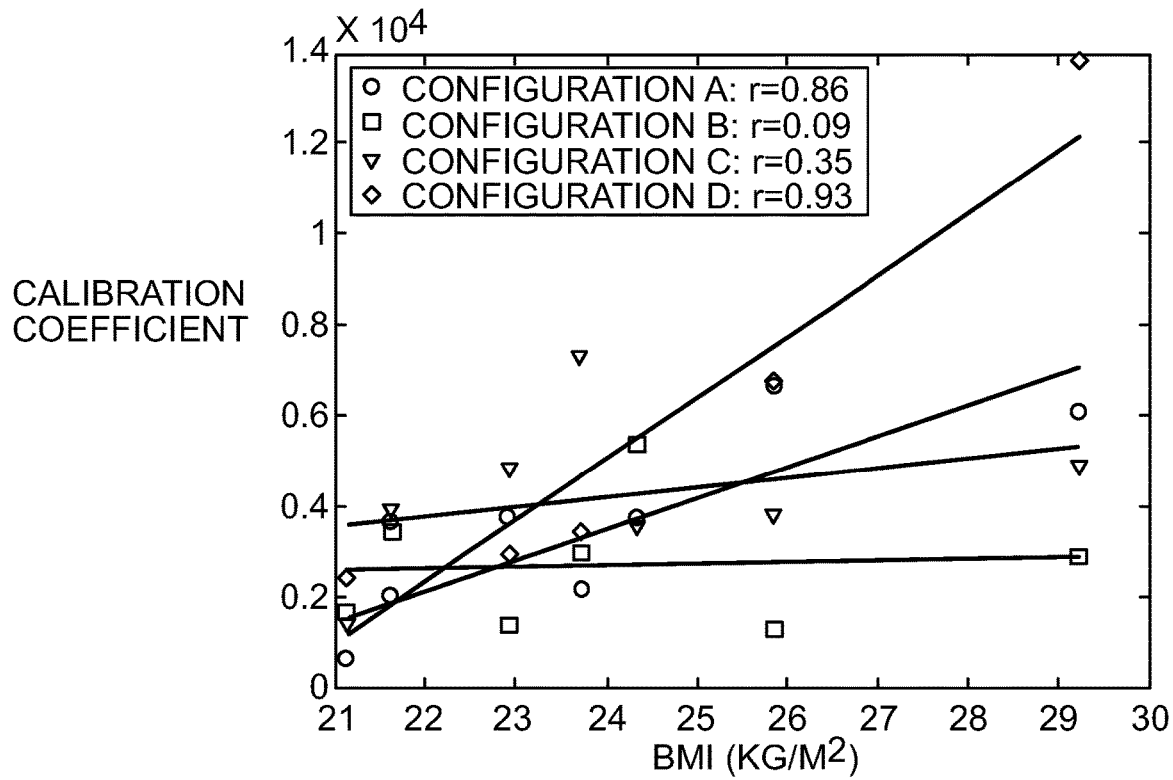
FIG. 14 is a plot of calibration coefficients against BMI for four different electrode configurations.

Referring now to FIG. 14, depicted is a graph of BMI versus the calibration coefficient for 7 patients. BMI is shown on the x-axis, and calibration coefficient is shown on the y-axis. The linear relationship between height and the calibration coefficient in configuration D (PRR placement as described earlier) is indicative of its utility in determining the calibration coefficient. Other physiological parameters such as height weight, body surface area, race, sex, chest circumference, inter-mammary distance, age also have important relationships with the calibration coefficient, and in one embodiment any or all of these parameters aid in accurate determination of the calibration coefficient. A combination of statistical analysis and an expert system is used to determine a given patient's correlation coefficient based on the input of said physiological parameters. Such methods may include principal component analysis, artificial neural networks, fuzzy logic, and genetic programming and pattern analysis. In a preferred embodiment, test data from a pilot study is used to train the expert systems. In a preferred embodiment, existing data regarding patient demographics and pulmonary function are used to train the expert system. Preferably, a combination of test data from a pilot study and existing pulmonary function datasets are use to train the expert system.

Figure 15:
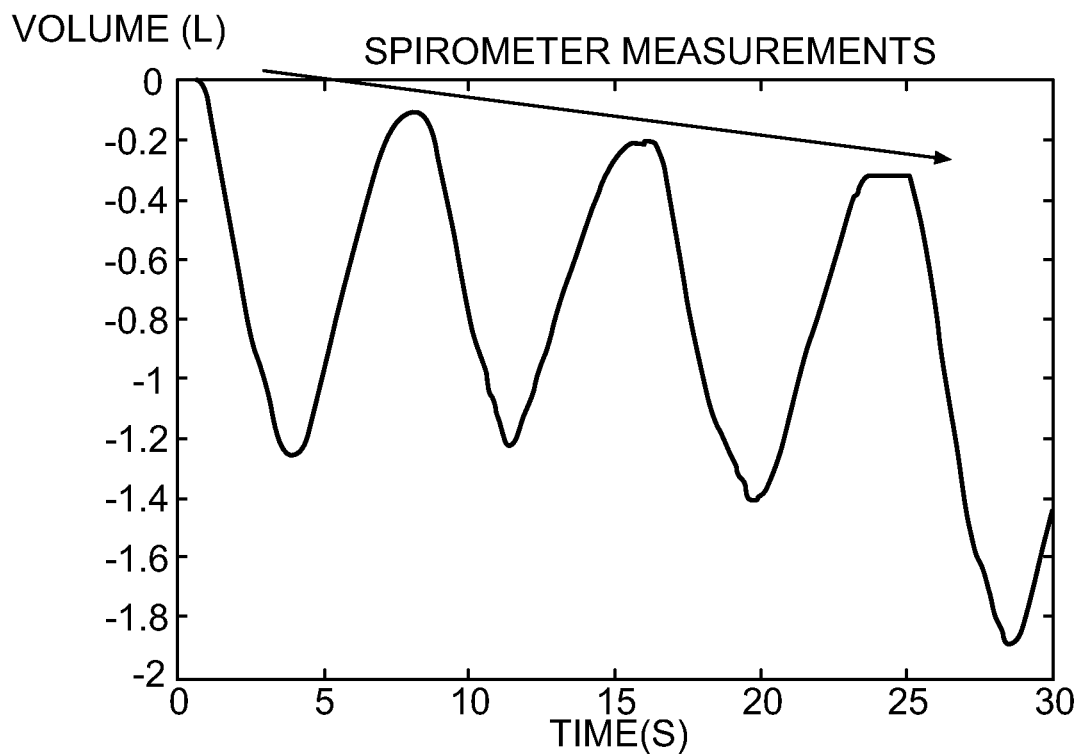
FIG. 15 is a spirometry plot that exhibits volume drift.
Figure 16:
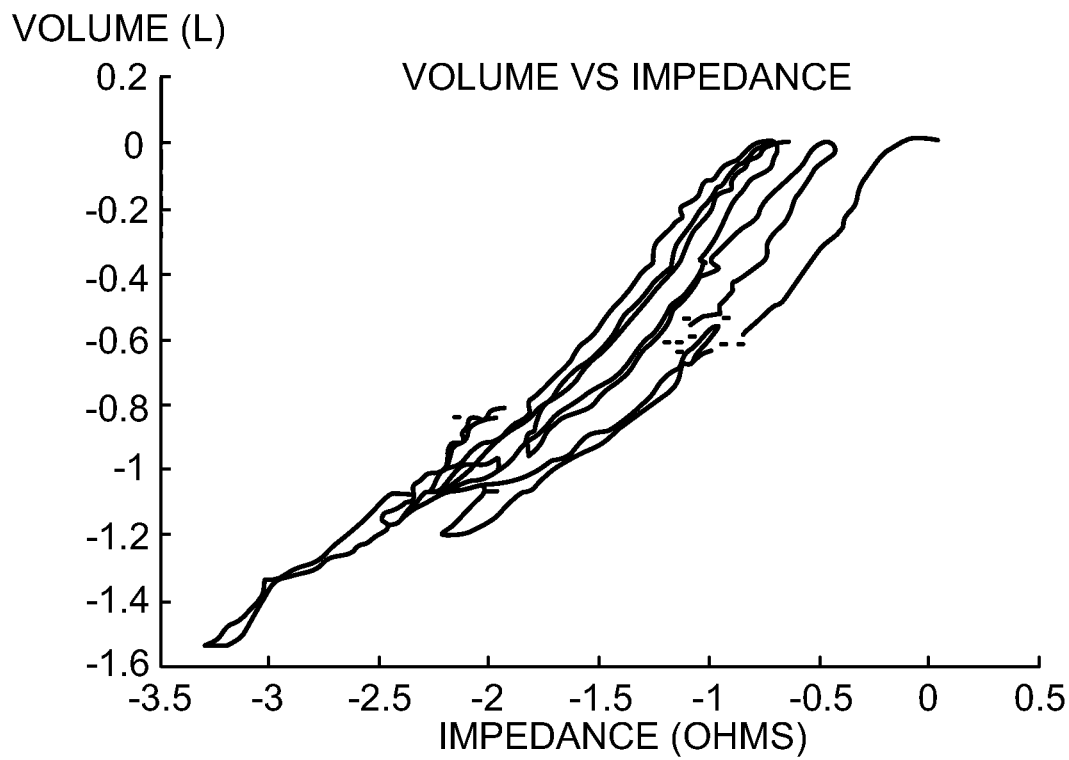
FIG. 16 is a volume vs. impedance plot that is affected by volume drift.
Figure 17:
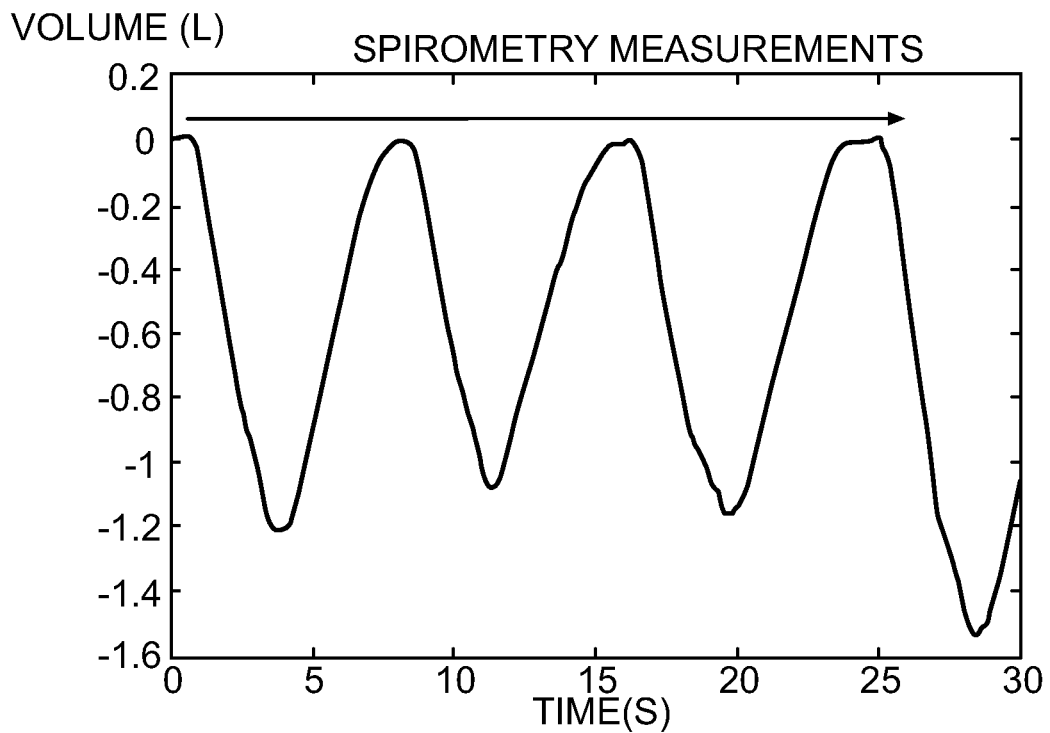
FIG. 17 is a spirometry plot that is corrected for volume drift.
Figure 18:
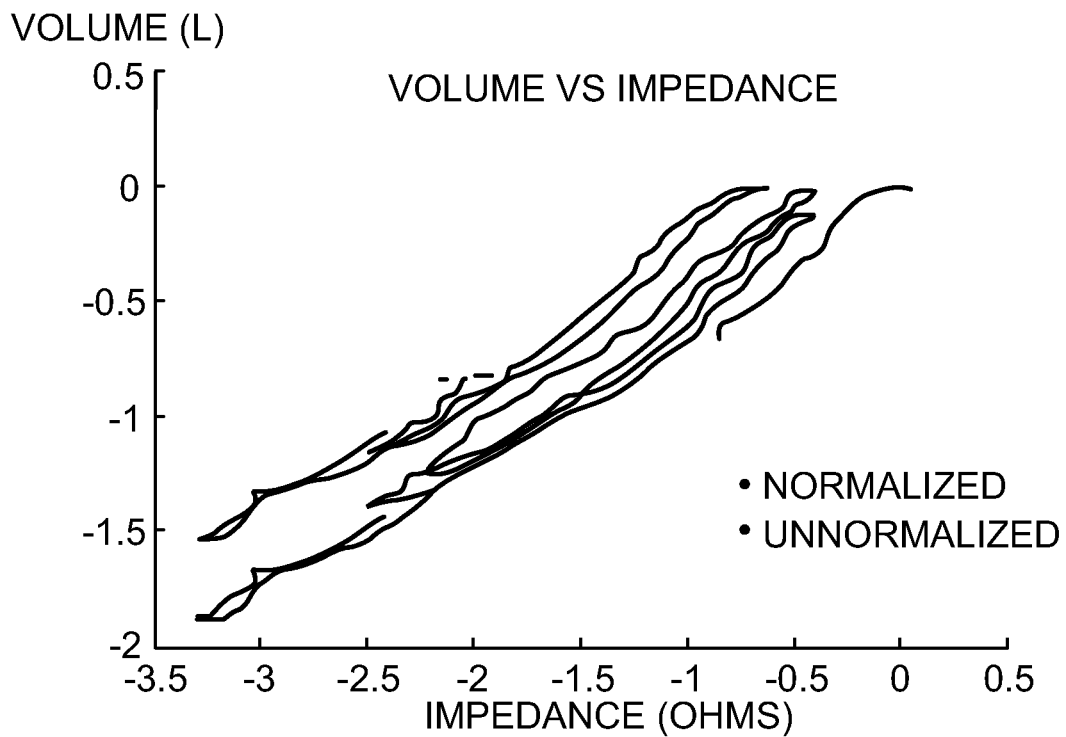
FIG. 18 is a plot of volume vs. impedance, comparing data that is uncorrected and corrected for volume drift.

One problem that is encountered with some spirometers is volume drift, where a greater amount of air is inspired rather than expired. Additionally, prolonged spirometry testing provides increase in resistance to pulmonary flow that can alter the physiology and/or can change the respiratory flows and/or volumes. These patterns can disrupt the correlation coefficient for the test by altering the volume so that it trends downwards while the impedance trace stays constant. FIG. 15 shows a volume curve that exhibits volume drift. FIG. 16 shows a volume versus impedance curve for that set where the volume drift damages the fit of the plot. In one embodiment, the device corrects for the problem by subtracting out a line with a constant slope value. After using this mean flow method, the curves do not trend up or down as seen in FIG. 17 and the volume versus impedance data stays much tighter as seen in FIG. 18, and the volume versus impedance data stays much tighter, giving higher correlations and better correlation coefficients. In one embodiment, volume drift subtraction is used in calibration. In one embodiment volume drift subtraction is used in deriving the calibration coefficient. The same utility is also achieved by differentiating the volume curve to get flow, subtracting the DC offset between intervals that have the same lung volume at the start and end point, and then integrating to get flow without the drift artifact.

In another embodiment of the device, the calibration coefficient is determined by comparing the RVM data trace and calculated values compared to predicted values for the patient's tidal volume, FVC, FEV1 etc. based on standard tables of spirometric data created by Knudsen, Crapo, or others known to those skilled in the art.

Data Analysis

Figure 19:
FIG. 19 is a flow chart that describes data analysis for the invention.

Referring now to FIG. 19, there is shown a flow chart that displays the progression of data through the analysis software. Raw data is recorded by the impedance meter, digitized using an analog to digital converter, and inputted to the programmable element through a standard data port. Data processing strips the signal of noise and motion artifacts. Analysis algorithms calculate the volume trace as well as medically relevant information including but not limited to: frequency and time domain plots of the impedance and/or calculated volume traces, respiratory rate, tidal volume, and minute ventilation. In one embodiment, the analysis algorithm to convert impedance into volume traces utilizes either calibration in conjunction with spirometer or ventilator data, or in another embodiment, calibration based on physiological parameters. The algorithm produces a correlation coefficient which, when multiplied with the impedance data, converts the impedance scale into a volume scale. In addition, the algorithms take variability of the above metrics into account and automatically calculate a standardized index of respiratory sufficiency (RSI). This RSI contains information that integrates information from one or more measurements and/or utilizes the range of acceptable values of the following measurements individually and in combination to provide a single number related to respiratory sufficiency or insufficiency: respiratory rate, respiratory volume, respiratory curve characteristics, respiratory variability or complexity as previously prescribed.

In one embodiment, one of the following methods are used in calculation of the RSI: change in patient status from previous measurement, second derivative of change in patient status from previous measurements, multivariate analysis, pattern analysis, spectral analysis, neural networks, self-teaching system for individual, self-teaching system for patient population.

In one embodiment, the RSI also includes data from the following: oxygen saturation, TcpO2, TcpCO2, end tidal CO2, sublingual CO2, heart rate, cardiac output, oncotic pressure, skin hydration, body hydration, and BMI. The advantage of this index is that it can be understood by untrained personnel and it can be linked to alarms to notify physicians or other caregivers in case of rapidly deteriorating health. After computation, processed metrics pass to the output module, which may be embodied as a printer or displayed on a screen or delivered by oral, visual, or textual messaging.

In one embodiment, the device notes a pattern in the curve recorded during the inspiratory or expiratory phase of respiration. In one embodiment, the device notes a pattern in the respiratory variability in rate, volume and/or location of respiration. In one embodiment the pattern is noted in the shape of the respiratory curve. In one embodiment, the pattern analysis includes the values derived from the slope of inspiration. In one embodiment, the pattern analysis includes the values derived from the slope of expiration. In one embodiment, the pattern analysis includes a combination of parameters which could include any or all of the following: respiratory rate, minute ventilation, tidal volume, slope of inspiration, slope of expiration, respiratory variability. In one embodiment, these parameters are used within the calculation of a Respiratory Health Index (RHI) that provides a standardized quantitative measure of adequacy of ventilation. In one embodiment, the RHI is coupled with alarms that sound either when respiration falls below what is deemed as adequate, or within the range that is deemed adequate, if the patient experiences a very sudden change. In one embodiment, the device provides information to calculate an RHI. Preferably the device calculates and displays the RHI. In one embodiment, the Respiratory Health Index is compared against a universal calibration based on patient characteristics. In one embodiment, the RHI provides quantitative data with the system calibrated to a specific patient.

Figure 27:
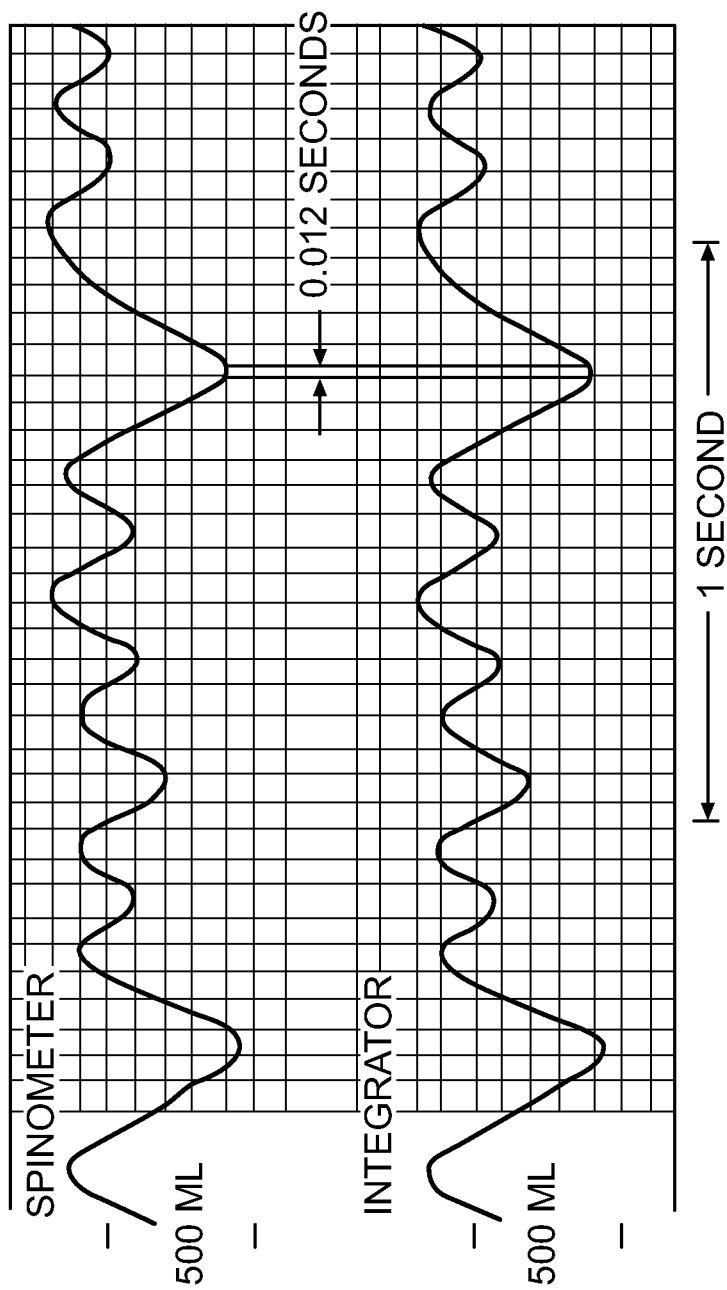
FIG. 27 shows graphs of impedance versus time and volume versus time for simultaneously recorded data.

Referring now to FIG. 27, the time delay or phase lag of an impedance signal and a volume signal is shown. In this particular figure, the delay was found to be 0.012 seconds. Phase lag between volume and impedance signals is an important issue that is addressed in one embodiment. There is a time lag between impedance and volume signals due to the elastic and capacitive nature of the pleura and lung tissue, which creates a slight delay between the diaphragm moving and air flowing in the lung. In one embodiment, this phase difference is used as a measure of lung stiffness and airway resistance. Frequency phase analysis allows the user to find the phase angle. A larger phase offset is indicative of a high degree of airway resistance to motion. Calculation of the phase angle is accomplished by comparing simultaneously recorded and synchronized RVM curves with flow, volume or pressure curves recorded by a spirometer, pneumotachometer, ventilator or similar device. In one embodiment the phase lag between volume and impedance signals is a component of the algorithm that is used to calibrate the system to a given individual. In one embodiment the phase lag is used to calibrate the system for a universal calibration. When calculating the calibration coefficient using an external pressure, flow, or volume measuring device, the leading curve is shifted by the magnitude of the phase lag so as to correlate temporally with the trailing curve. This embodiment increases the accuracy of the calibration algorithm. When no external pressure, flow, or volume measuring device is used for calibration, a virtual phase lag is calculated based on patient characteristics, including demographic information, physiological measurements, and pulmonary function test metrics.

In one embodiment, phase lag is corrected for by RVM algorithms in aligning both impedance and volume. In one embodiment, phase lag data is presented independently as a standardized index to demonstrate a measure of lung compliance and stiffness. In one embodiment, phase lag data is integrated within the Respiratory Health Index as a measure of respiratory status.

In one embodiment, frequency domain analysis is applied to the RVM measurements. Preferably, at least one frequency domain plot such as a Fourier transform is displayed to the operator. Preferably, at least one 2-dimensional frequency domain image of the RVM data such as a spectrograph is displayed to the operator, where one dimension is frequency and the other is time, and the magnitude of the signal at each location is represented by color. Preferably, the frequency domain information is used to assess respiratory health or pathologies. Preferably, an alarm will alert a medical professional if the frequency domain data indicates rapid deterioration of patient health.

In a preferred embodiment, RVM measurements are used as the basis for complexity analysis. In one embodiment, complexity analysis is performed on the RVM signal alone. Preferably, RVM measurements are used in combination with other physiologic measurements such as heart rate, urine output, EKG signal, impedance cardiogram, EEG or other brain monitoring signal.

In a preferred embodiment, RVM measurements are utilized as a component of complexity analysis in combination with data provided by a device used to treat or monitor the patient including: the ventilator measurement of the patient generated respiratory pressure, the ventilator measurement of the patient generated respiratory flow, the ventilator measurement of the patient generated respiratory volume, the ventilator measurement of the ventilator generated respiratory pressure, the ventilator measurement of the ventilator generated respiratory flow, the ventilator measurement of the ventilator generated respiratory volume an infusion pump, or other devices used to treat the patient, RVM measurements may be used to quantify breath-to-breath variability. One embodiment of the device is used to define a specified point along the respiratory curve with which to calculate breath-to-breath variability in respiratory rate such as the peak of inspiration or nadir of expiration. Preferably, peaks or nadirs of each respiration are automatically identified. In one embodiment, the device provides data with describing breath-to-breath variability in volume inspired. In one embodiment, the device provides data describing breath-to-breath variability or complexity in the slope or other characteristics of the respiratory volume or flow curve. In one embodiment, the device provides data with which to calculate variability or complexity associated with the location of respiratory effort, such as chest vs. abdominal or one hemithorax vs. the other, by collecting data from different locations on the body with the same or different electrode pairings. Preferably, the device calculates breath-to-breath variability or complexity of one or more of these parameters. Preferably, the device presents the variability or complexity analysis in a form that is easy to interpret by the user. In one embodiment, the device combines data from more than one source of variability or complexity among the following: respiratory rate, respiratory volume, location of respiratory effort, slope or other characteristic of the respiratory volume or flow curves, to provide an advanced assessment of respiratory function. In one embodiment, the device analyzes the variability or complexity data intermittently or continuously and presents the data at intervals such as every 10 minutes, every 30 minutes, or every hour. Preferably, the device presents the variability analysis in less than 10 minutes, less than 5 minutes, less than 1 minute, or in near real time. In one embodiment, the variability or complexity of any of the respiratory parameters may be quantified by linear or nonlinear analysis methods. Preferably, the variability or complexity of any of the respiratory parameters may be quantified by nonlinear dynamical analysis. In one embodiment, approximate entropy is used by the device for data analysis. In one embodiment, variability or complexity analysis of the data is combined with volume data to provide a combined index of respiratory function. In one embodiment, variability or complexity analysis data is combined with other parameters and presented as a Respiratory Sufficiency Index or a Respiratory Health Index.

In a preferred embodiment, RVM measurements or the complexity analysis of the RVM signal is utilized as at least a part of the information used in goal directed therapy. In a preferred embodiment, RVM measurements or the complexity analysis of the RVM signal provide information for decision support. In a preferred embodiment RVM measurements or the complexity analysis of RVM signal is utilized as at least a part of the patient data required for a controlled loop system.

Use in Imaging

In one embodiment of the device, the respiratory cycle is measured by one or more methods including but not limited to impedance pneumography, end tidal $CO_2$, or pulse oximetry while the heart is imaged or otherwise measured using echocardiography which may be embodied as 2D echo, 3D echo or any other type of echocardiography. Time series data from the echocardiogram is marked as having a certain accuracy rating based on the respiratory motion recorded by the respiratory monitor. In one embodiment, echocardiography data below an accuracy threshold is discarded. In another embodiment, echocardiography data is weighted based on its accuracy rating where the least accurate data is weighted lowest. The device generates a composite image or video of the heart and cardiac motion based on the most accurate echocardiogram data. In one embodiment, echocardiography data is recorded over more than one cardiac cycle, then after analysis and accuracy rating, the best data is used for generating a composite image of the heart or video of the cardiac cycle.

Other embodiments include combining respiratory cycle measurement and quantification with other cardiac imaging techniques for the purpose of improving accuracy. The methods of cardiac imaging may include Doppler flow measurements, radionuclide study, gated CT, and gated MRI. Other embodiments include combining respiratory cycle measurement by RVM with other diagnostic or therapeutic modalities of the chest, abdomen, and other body parts, including diagnostic CT or MRI, catheter directed therapy, directed cardiac ablation, radioablation of tumor, radiation of tumor. In a preferred embodiment, RVM and cardiac impedance data are utilized together for timing of data collection or data analysis of diagnostic imaging or anatomically directed therapy.

In another embodiment of the device, the respiratory impedance measurements or data from complexity analysis of RVM measurements are used to generate an image of the lungs. In another embodiment of the device, data from complexity analysis of RVM measurements and cardiac impedance measurements are used to generate an image of the heart and lungs. In the preferred embodiment, the heart and lungs are imaged simultaneously. In one embodiment, the device is used for generating 2D images, videos, or models of the heart and/or lungs. In the preferred embodiment, the device generates 3D images, videos or models of the heart and/or lungs.

Detecting Pathologies and Improving Monitoring

In one embodiment, the device provides RVM data which, with our without variability or complexity analysis, is used to aid in decision making such as extubation or intubation for mechanical ventilation. In one embodiment the device provides RVM data which, with or without variability or complexity analysis, aids in decision making regarding drug administration or other therapeutic intervention. In one embodiment, the device uses variability or complexity information alone or with volume data as part of an open or closed loop control system to adjust ventilatory settings. In one embodiment, the device uses variability or complexity information, alone or with volume data or other analysis of the respiratory curve provided by RVM, as part of an open or closed loop control system to adjust doses of medications. This embodiment is useful for premature infants to optimize the management of a pressure ventilator, and for patients with uncuffed endotrachial tubes. In one embodiment, the device uses variability or complexity information, alone or with volume data or other analysis of the respiratory curve provided by RVM, as part of a patient management system that monitors patient status, recommends medication delivery, and, then, reassesses the patient to direct further action.

In one embodiment the device uses variability or complexity analysis of the RVM signal alone, volume data alone, curve analysis alone, or any of these in combination to trigger alarms indicating change in patient status. In another embodiment, symbol-distribution entropy and bit-per-word entropy are used to measure the probability of patterns within the time series. In another embodiment, similarity of distributions methodology is used. In one embodiment, the device sounds an alarm when it detects a change in respiratory complexity or a respiratory complexity below a specified threshold or more constrained breathing patterns associated with pulmonary pathology or disease states. In one embodiment, the device sounds an alarm when it detects a change in a combined measurement of respiratory and heart rate complexity beyond a specified threshold.

In one embodiment, RVM measurements are integrated into an open or closed feedback loop to report adequacy of ventilation by ensuring safe dosage of medication by monitoring ventilation for warning signs of respiratory arrest. In a preferred embodiment, RVM is integrated into a system with a ventilator providing an open or closed feedback loop by which ventilator adjustments are made. Differences between RVM measurements and ventilator or spirometer generated volume or flow measurements can be used to provide information for diagnosis and guidance of therapy. By using RVM monitoring with or without additional information from end tidal $CO_2$ or pulse oximetry measurements, this embodiment automatically weans the patient by gradually decreasing ventilatory support and observing RVM and other parameters and alerts the physician of readiness for extubation, or alerts for failure to progress. This combined system with either pulse oximetry or ETCO2 or both could be used as an open or closed loop system to deliver narcotics or other respiratory depressant drugs such as benzodiazepines or propofol.

In one embodiment, the analysis algorithm detects the presence of specific respiratory patterns maintained in the expert system database and informs the physician or other health care provider about the possibility of associated pathology. In one embodiment, the respiratory pattern for a given pathology is recognized and in a preferred embodiment, quantified. In another embodiment the pathology is localized.

In a preferred embodiment, the device recognizes a specific patterns related to respiratory volume, curve, variability or complexity or other analysis of RVM data.

In one embodiment, the device recognizes the pattern associated with impending respiratory failure or respiratory arrest and delivers an audible and/or visible alert or warning. In one embodiment, the device analyzes the respiratory data or the trend in the data and makes a recommendation for intubation and mechanical ventilation. In one embodiment, the device analyses the respiratory pattern data and adjusts the level of infusion of a narcotic or other respiratory depressant drug such as propafol.

In one embodiment, the device recognizes the respiratory pattern associated with a specific disease entity or pathology such as congestive heart failure, or asthma or COPD or narcotic induced respiratory depression or impending respiratory failure. In one embodiment, the device alerts the physician to this pathology. In one embodiment the device quantifies the degree of the pathology. In one embodiment, the device recognizes a pattern of congestive heart failure and provides data regarding the trending toward improvement or deterioration with time or as associated therapeutic intervention.

Preferably, the impedance measuring element of the device can produce Impedance Cardiograph (ICG) measurements. Preferably, the device detects impedance variability associated with heart rate variability. Preferably the device detects impedance variability associated with variability of the respiratory waveform or other respiratory parameter and utilizes the heart rate and respiratory rate, volume or waveform variability to predict cardiac, respiratory and pulmonary complications. Preferably, the device maintains alarms for predetermined limits associated with unsafe pulmonary variability or complexity or combined heart rate and respiratory variability or complexity.

In another embodiment, End Tidal $CO_2$ ($ETCO_2$) is used in addition to or instead of subjective assessment to determine the RVM baseline. In one embodiment, RVM is coupled with $ETCO_2$ measurements to provide additional information regarding respiratory status.

In another embodiment RVM is coupled with pulse oximetry to provide information about both ventilation/respiration and oxygenation. A more complex RVM system couples standard RVM measurements with both or either $ETCO_2$ or pulse oximetry. This combined device provides further information about breathing for sedated patients and enhances patient monitoring.

In a preferred embodiment, measurments of lung volumes and minute ventilation are used to assess the adequacy of the patient after extubation in a quantitative way. Minute ventilation is specifically used for patients undergoing surgery. Preferably, a preoperative measurement of tidal volume or minute ventilation is obtained as a baseline for the specific patient. Preferably the baseline is used post-operatively as a comparison between preoperative and postoperative respiratory status. The trend of tidal volume or minute ventilation is used to monitor a patient during surgery or a procedure or during post-operative recovery in the Post Anesthesia Care Unit, in the Intensive Care Unit, or on the hospital floor. This trend gives an accurate measure of differences and changes in the patient's breathing from preprocedure baseline and can denote when the patient returns to a baseline level of breathing. In a preferred embodiment, the device directly aids the physician to make an appropriate extubation decision by defining an adequate level of breathing specific to that patient. In one embodiment, absolute lung volumes are compared with precalibrated data derived from patient characteristics, and are used in determining the presence of restrictive and/or obstructive lung disease and other respiratory conditions. Absolute volume data can be especially useful within the PACU and ICU as a complement to existing quantitative data.

Use in PCA feedback and Drug Dosing Optimization

One use of the device is to use cardiac and/or respiratory data measured and recorded by one, several, or a combination of the technologies listed herein, to determine the effect of one or more drugs or other medical interventions on the patient. In an embodiment, the respiratory monitor is used to judge the side effects of analgesic drugs on the body and prevent or assist in the prevention of respiratory failure or other compromises due to adverse reaction or overdose.

In a preferred embodiment, the device is paired with or integrated into a patient controlled analgesia (PCA) system. This is accomplished electronically through communication between the device of the invention and an electronic PCA system, or by an integrated monitor/PCA system or by a setting in the monitor indicating that the patient is being administered PCA. In this embodiment, the administration of analgesia or anesthesia is limited based on the risk of respiratory or other complications predicted by the device. If the PCA system is not electronic, or analgesic drugs are being delivered by personnel, the device makes recommendations as to when the risk of respiratory complication is high and the dosage should be lowered.

Another embodiment of the device of the invention is a diagnostic/therapeutic platform. The monitoring device is paired with one or more of the following: pharmaceutical regimens, therapeutic regimens, use of inhaler, use of nebulizer, use of pharmaceutical targeting respiratory system, use of pharmaceutical targeting cardiovascular system, use of pharmaceutical targeting asthma, COPD, CHF, cystic fibrosis, bronchopulmonary dysplasia, pulmonary hypertension, other diseases of the lungs. This embodiment of the device is used to judge the effectiveness of possible medical and nonmedical interventions on respiratory state or respiratory health and suggest changes in regimen for optimization and/or suggest appropriate interventions when the patient is at risk for complications.

In one embodiment RVM is paired with behavioral algorithms or algorithm that includes information about any of the following patient medical status, environmental factors, and behavioral factors of a demographic group or of the patient in general. In a preferred embodiment, one of the algorithms described above could denote the necessity for obtaining an RVM measurement. More preferably, the RVM measurements are used in conjunction with behavioral/medical/environmental algorithmic data to provide information to indicate action or therapy. An example of the use of this embodiment of the device would be an algorithm which includes the patient's previous respiratory complications or chronic respiratory illness, and/or allergies as inputs along with behavioral events known to exacerbate said conditions. By including information from the patient's schedule (e.g. attending an outdoor event during allergy season, or participating in a sporting competition), the system recommends that he take an RVM measurement then makes recommendations about whether to maintain normal dosing of medication or increase it. The software can also recommend that the patient bring medication with him to the event, and generally remind the patient to take his medication. Another example could be that the patient had an asthma attack or other respiratory complication. RVM data could be utilized to assess the severity of this attack by any of the measured parameters including minute ventilation, tidal volume, time for inspiration vs. expiration (i.e. ratio), shape of the respiratory curve during normal breathing, shape of the respiratory curve during the deepest possible breath or other respiratory maneuver. The data could then prompt independently or be used in conjunction with other information to make a decision for the patient to perform an action including one of the following: do nothing, rest, use an inhaler, take a pharmaceutical, use a nebulizer, go to the hospital. Information as to the action required could be part of a behavioral or other algorithm designed for the specific patient or a group of patients with a similar disorder, patients with a similar demographic, patients with a specific medical, anatomic or behavioral profile or patients in general. Preferably, after the action, the patient is instructed to repeat the RVM measurement to assess the adequacy of therapy. Preferably his repeat measurement is compared to the measurement before the therapy or other intervention and changes are noted. Additional information from this comparison or just data taken after therapy is used alone or in combination with other patient data to make further medical decisions or recommendations for action.

For example, an asthmatic is having symptoms and decides to or is instructed by a disease management algorithm to obtain an RVM measurement. The RVM data is analyzed by the device, utilized independently or compared to his historic baseline or the last measurement taken. Based on these, with or without other patient specific inputs such as heart rate, the device recommends he use his inhaler. A second set of RVM data is then taken. The RVM data is compared to the previous RVM data taken prior to treatment. The device then follows a decision tree and tells the patient he has improved and needs no further therapy, that he needs to repeat the dosage, that he needs to call his physician, or that he immediately needs to go to the hospital. In a preferred embodiment, the RVM data is combined with behavioral algorithms developed for a demographic or for a specific patient to optimize recommendations for the patient.

PACU/ICU Usage

In one embodiment, the device is used within a Postoperative Anesthesia Care Unit (PACU) setting, as either a standalone monitor or as an accompaniment to or incorporated in an existing monitor. Within the PACU, RVM volume is calculated and compared against pre-calibrated data derived taking into account BMI, height, weight, chest circumference, and other parameters. The device is used to complement existing quantitative data that supports decision making within the PACU. In one embodiment, within the operating room, RVM data is correlated with end tidal carbon dioxide measurements to provide a more comprehensive assessment of respiratory status. RVM derived measurements including minute ventilation are used to compare a patient's status before, during, and after surgery or a procedure and to document the effect of anesthesia/narcotic induced respiratory depression. RVM is used to support more subjective assessments made by clinicians in the PACU by providing a quantitative justification for certain decisions, including the decision to re-intubate. The device also supports subjective assessment regarding patients on the hospital floor as a monitor for decline in respiratory status and an alarm for the need to re-intubate or perform another intervention to improve respiratory status. Preferably, RVM measurements will assist in regulation of narcotic pain medication, sedative drugs such as benzodiazepines, or other drugs with respiratory depressive effects. In one embodiment, the above mentioned uses regarding the RVM in a PACU setting are implemented within the ICU setting such as a Neonatal ICU, Surgical ICU, Medical ICU, Pulmonary ICU, Cardiac ICU, Coronary Care Unit, Pediatric ICU, and Neurosurgical ICU. In another embodiment, the RVM device is used in the setting of a step down unit or standard hospital bed to follow respiratory status.

Later in the postoperative period or otherwise, measurements of the respiratory pattern, including tidal volumes, respiratory rate, minute ventilation, variability in interbreath interval or volume, or RVM signal complexity can be compared to baseline values measured before surgery. This can directly aid the extubation decision by defining what is an adequate level of breathing specific to that patient. In another embodiment of the device, RVM monitoring identifies problems that are commonly associated with ventilators, such as poor endotracheal tube positioning, hyperventilation, hypoventilation, rebreathing and air leaks. The system also identifies air leaks through a chest tube or cuffless tube. Air leaks would cause a downward trend to appear on any direct volume measurement which would not be present on the impedance trace, thus the device can detect and report air leaks in devices which directly measure volume or flow. In a preferred embodiment, the system identifies abnormalities and trends specific to a hemithorax such as those related to the following pathologies: pneumothorax, pulmonary contusion, rib fractures, hemothorax, chylothorax, hydrothorax, and pneumonia.

In one embodiment, the device is used during Monitored Anesthesia Care (MAC) to monitor respiratory status, assist in drug and fluid administration, provide indication of impending or existing respiratory compromise or failure, and assist in the decision to intubate if necessary.

In another embodiment of the device, RVM monitoring identifies problems that are commonly associated with ventilators, such as poor endotracheal tube positioning, hyperventilation, hypoventilation, rebreathing and air leaks. In one embodiment RVM measurements are combined with data derived from the ventilator to provide additional data regarding physiology. An example of this is that differences can be recorded in RVM measurements vs. inspired or expired flows or volumes measured on the ventilators to assess "work of breathing" in a quantitative fashion.

In another embodiment, RVM measurements are taken after surgery in a patient who is still under the effects of anesthesia or pain medication to monitor patient recovery. Recording a baseline tidal volume curve for a patient during normal preoperative conditions provides a comparison baseline for monitoring during and after surgery. Returning to a similar tidal volume curve is one signal of respiratory recovery after being taken off a ventilator. In this embodiment of the invention, the device is used to evaluate the success of extubation and determine if reintubation is necessary. The invention described herein allows these measurements to be taken noninvasively and without being in the stream of inspired/expired air or impeding airway flow or contaminating the airway circuit.

In one embodiment, the device is used within outpatient surgicenters, specifically geared towards patients receiving Monitored Anesthesia Care, including patients undergoing orthopedic procedures, cataract surgery and endoscopy of the upper and lower GI tract.

Diagnostic Usage

In one embodiment, the device is used to quantify respiratory parameters during performance based tests. In a preferred embodiment, the device is used to quantify respiratory parameters in tests of cardiovascular function including stress tests. In a preferred embodiment, the device is used in combination with one of the following tests to assess impact of the test on respiration. In a preferred embodiment, the device reports effects of exercise or a particular drug like dopamine on the overall physiology or metabolism of the body as reflected by changes in respiratory volumes, patterns, rate or combinations thereof including advanced analysis of breath-to-breath variability/complexity, fractal or entropy based analyses as described elsewhere. In a preferred embodiment, the device is used to evaluate the safety of a given level of exercise or pharmacologic stress.

In a preferred embodiment, variability or complexity analysis of RVM measurements is undertaken in concert with standard pulmonary function testing. In a preferred embodiment, variability or complexity analysis of RVM measurements is undertaken with or without heart rate variability/complexity analysis in concert with standard cardiovascular physiology testing such as stress testing, walking tests for claudication, or other performance based testing.

In a preferred embodiment, the device is used to evaluate the effects of drugs on the respiratory system including bronchodilators for diagnostic purposes, monitoring of therapeutics, optimization including effects on both heart and lungs. More preferably, the device above combines respiratory information obtained by impedance or other methods described with EKG information about heart rate, heart rate variability, EKG evidence of ischemia or arrhythmia. In a preferred embodiment, the device is used to evaluate the effects of bronchoconstrictors as in a provocative test. In various embodiments, the device obtains continuous or intermittent RVM measurements. In a preferred embodiment, the device provides trending of RVM data.

In a preferred embodiment, the device is used to evaluate the effects of metabolic stimulants, cardiovascular drugs including beta blockers, alpha adrenergic agonists or blockers, beta adrenergic agonists or blockers. In a preferred embodiment, the device is used during a stress test to demonstrate level of effort placed or to demonstrate an unsafe condition relative to the pulmonary system to terminate or modify the test. Stress Introduced to the patient is created by various means including but not limited to, exercise and/or the delivery of a drug. In a preferred embodiment, the device indicates or works with other technologies described earlier to indicate the level of overall exercise. In a preferred embodiment, the device is used as a free-standing device for measuring the effects of exercise or other stimulant on the pulmonary system.

In another embodiment of the device, the respiratory information is combined with cardiac information to define the level of exertion related to EKG changes associated with cardiac disease. In another embodiment of the device, the system combines respiratory information with cardiac information to determine the level of exertion of an athlete.

In another embodiment, the device provides warning of potential negative impact of the level of exercise on overall health or on cardiac status, with or without pairing respiratory signals with cardiac impedance or EKG measurements in the home, athletic field, military environment or out of hospital setting. One embodiment of the device is a holter monitor which outputs values for one or more of the following: respiratory effort, level of activity, state of physiology, or metabolism associated with different rhythms, depolarization or other cardiac pathophysiology.

One embodiment of the invention is similar to a holter monitor which monitors one or more physiological parameters over hours to days in a hospital, home, or other setting. One embodiment of the device is combined with a holter monitor or critical care monitor which specifically monitors decompensation effects related to heart failure. A similar embodiment of the device monitors and outputs measurements of "lung water". In one embodiment, the device is included in a disease management system for congestive heart failure.

In a most preferred embodiment, the device provides a continuous measurement which can be run for long periods of time and can deliver a time curve demonstrating the effects of exercise or a drug for diagnosis, therapeutic monitoring or drug development.

One embodiment of the device provides trending data over minutes to hours to days for patients with a variety of disease states including chronic obstructive pulmonary disease, congestive heart failure, pulmonary hypertension, pulmonary fibrosis, cystic fibrosis, interstitial lung disease, restrictive lung disease, mesothelioma, post thoracic surgery, post cardiac surgery, post thoracotomy, post thoracostomy, post rib fracture, post lung contusion, post pulmonary embolus, cardiac ischemia, cardiomyopathy, ischemic cardiomyopathy, restrictive cardiomyopathy, diastolic cardiomyopathy, infectious cardiomyopathy, hypertrophic cardiomyopathy. Preferably the device provides information about changes in respiration in these disease states related to interventions or provocative testing procedures.

In one embodiment of the device of the invention, the system is used to diagnose various diseases. In a preferred embodiment, the device is used to assess the risk of developing pneumonia. In another embodiment, the device is used to assess the risk that a pneumonia therapy is not effective, and suggest corrective action. Another embodiment of the invention is used for the evaluation of functional deterioration or recovery associated with diseases including but not limited to: pneumonia, heart failure, cystic fibrosis, interstitial fibrosis, hydration levels, congestion due to heart failure, pulmonary edema, blood loss, hematoma, hemangioma, buildup of fluid in the body, hemorrhage, or other diseases. This information may be used for diagnosis as above or be integrated with respiratory volume measurements or other physiological measurements that may be measured by the device or input into the device to provide a comprehensive respiratory sufficiency index (cRSI).

In one embodiment, disease specific modules can be created to gather disease specific information, employ disease specific algorithms and deliver either optimized respiratory volume data or respiratory diagnostic data related to the specific disease. In a preferred embodiment of the invention, respiratory curve analysis is used to diagnose medical conditions. In one embodiment, the system utilizes provocative tests to determine measurements or estimates of one or more of the following: tidal volume, residual volume, expiratory reserve volume, inspiratory reserve volume, inspiratory capacity, inspiratory vital capacity, vital capacity, functional residual capacity, residual volume, forced vital capacity, forced expiratory volume, forced expiratory flow, forced inspiratory flow peak expiratory flow, and maximum voluntary ventilation. In this embodiment, diagnostic tools such as flow volume loops are generated by software running on the system for diagnosis of various cardiopulmonary or other disorders.

Respiratory curve analysis can also be used to assess cardiopulmonary or other disorders without provocative tests. In one embodiment, an algorithm monitors trends in TV, MV and RR to provide a metric of respiratory sufficiency or respiratory sufficiency index (RSI). In another embodiment, an algorithm analyzes individual breaths as an input to diagnose respiratory conditions. In this embodiment, one or more of the following parameters are calculated on a breath by breath basis: inspiratory time ($I_t$), expiratory time ($E_t$), $I_t:E_t$ ratio, percent inspiratory time, tidal impedance, tidal volume and area under the curve. In this embodiment, the various parameters are outputted through the system's user interface or printable report for the user to assess respiratory disease state. In a preferred embodiment, an algorithm analyzes the parameters to act as a diagnostic aid. In this embodiment, the system outputs an index of disease severity or a positive/negative reading for the disease.

In one embodiment, the device is implanted. In a preferred embodiment, the device is powered from a pacemaker-like battery. In one embodiment the device is combined with a pacemaker or defibrillator. In one embodiment the device is adjusted or calibrated or interrogated using an external component.

Other embodiments and technical advantages of the invention are set forth below and may be apparent from the drawings and the description of the invention which follow, or may be learned from the practice of the invention.

Other embodiments and uses of the invention will be apparent to those skilled in the art from consideration of the specification and practice of the invention disclosed herein. All references cited herein, including all publications, U.S. and foreign patents and patent applications, including International Application No. PCT/US2008/76224 filed Sep. 12, 2008, U.S. application Ser. No. 12/677, 16 filed Mar. 9, 2010, U.S. Provisional No. 60/971,642 filed Sep. 12, 2007, and U.S. Provisional No. 60/973,292 filed Sep. 18, 2007, are specifically and entirely incorporated by reference. The term comprising, where ever used, is intended to include the terms consisting and consisting essentially of. Furthermore, the terms comprising, including, and containing are not intended to be limiting. It is intended that the specification and examples be considered exemplary only with the true scope and spirit of the invention indicated by the following claims.

The invention claimed is:

1. A device for assessing a patient, the device comprising:
   a sensor array comprised of a set of impedance measurement electrodes adapted to be placed in one or more tetrapolar configurations on the chest of the patient for acquiring a bioimpedance signal from the patient;
   a programmable element coupled to the sensor array and having acquisition circuitry;
   wherein the programmable element:
   determines a Respiratory Variation Monitoring (RVM) calibration coefficient based on the patient's bioimpedance signal and demographic information of the patient;
   adjusts the acquisition circuitry based on the calibration coefficient;
   determines signal variation in the bioimpedance signal;
   adjusts the acquisition circuitry for the signal variation; and
   analyzes the bioimpedance signal using the RVM calibration coefficient to determine a respiratory volume and/or respiratory flow parameter of the patient; and
   a visual and/or audible alarm coupled to the programmable element or a medical therapy system coupled to the programmable element, wherein the alarm or medical therapy system is activated upon the respiratory volume and/or respiratory flow parameter exceeding a predetermined threshold.

2. The device of claim 1, wherein the calibration coefficient is further based on at least one of: physiological measurements of the patient, measured ECG signals of the patient, baseline impedance levels of the patient, measurements from a spirometer, and measurements from a ventilator.

3. The device of claim 1, wherein the respiratory volume and/or respiratory flow parameter is associated with a measurement of one or more of the patient's respiratory rate, the patient's respiratory pressure, the patient's end tidal CO2, the patient's sublingual CO2, the patient's intensity of respiration, a measurement that assesses variability, variation, or complexity in at least one of the patient's respiratory rate, the patient's respiratory pressure, the patient's respiratory flow, a patient's end tidal CO2, the patient's sublingual CO2, the patient's intensity of respiration, a measurement of at least one of the shape of the patient's respiratory curve, change in the shape of the patient's respiratory curve, a respiratory curve based on the patient's inhaled volume, a respiratory curve based on the patient's exhaled volume, a respiratory curve based on the patient's inhaled pressure, a respiratory curve based on the patient's exhaled pressure, a respiratory curve based on the patient's inhaled flow, a respiratory curve based on the patient's exhaled flow, a respiratory curve based on motion of the patient's chest as measured by imaging, a respiratory curve based on motion of the patient's chest as measured by contact sensors placed on the chest, a respiratory curve based on motion of the patient's abdomen as measured by imaging, a respiratory curve based on motion of the patient's abdomen as measured by contact sensors placed on the abdomen, a respiratory curve based on motion of both the patient's chest and abdomen as measured by imaging, a respiratory curve based on motion of the patient's chest and abdomen as measured by contact sensors placed on the chest and abdomen, variation of the patient's interbreath intervals, phase lag between the patient's impedance and volume signal, variation of phase lag between the patient's impedance and volume signal, a measurement that assesses variability, variation, or complexity at least one of the shape of the patient's respiratory curve, change in the shape of the patient's respiratory curve, a respiratory curve based on the patient's inhaled volume, a respiratory curve based on the patient's exhaled volume, a respiratory curve based on the patient's inhaled pressure, a respiratory curve based on the patient's exhaled pressure, a respiratory curve based on the patient's inhaled flow, a respiratory curve based on the patient's exhaled flow, a respiratory curve based on motion of the patient's chest as measured by imaging, a respiratory curve based on motion of the patient's chest as measured by contact sensors placed on the chest, a respiratory curve based on motion of the patient's abdomen as measured by imaging, a respiratory curve based on motion of the patient's abdomen as measured by contact sensors placed on the abdomen, a respiratory curve based on motion of both the patient's chest and abdomen as measured by imaging, a respiratory curve based on motion of the patient's chest and abdomen as measured by contact sensors placed on the chest and abdomen, variation of the patient's interbreath intervals, phase lag between the subject's impedance and volume signal, variation of phase lag between the subject's impedance and volume signal, and combinations thereof.

4. The device of claim 2, wherein the physiological measurement of the patient comprises at least one measurement selected from the group consisting of a calculation or estimation of the patient's viability, of the patient's injury severity, an assessment of the patient's likelihood of collapsing, an assessment of the patient's likelihood of suffering respiratory failure, an assessment of the patient's depth of anesthesia, an assessment of the patient's drug dosage level, an assessment of the patient's likelihood of cardiopulmonary failure, an assessment of the likelihood of equipment failure for equipment associated with treating the patient, and combinations thereof.

5. The device of claim 1, wherein the impedance measurement electrodes are remote probes placed on the thorax or abdomen of the patient, and wherein the programmable element is further programmed to analyze one or more remote probe data sets collected from the one or more remote probes.

6. The device of claim 5, wherein an impedance measurement is based on a plurality of remote probe data sets, and wherein the programmable element is further programmed or configured to enhance at least one of the plurality of remote probe data sets, or to stabilize at least one of the plurality of remote probe data sets, or to analyze each of the plurality of remote probe data sets for dynamic range and signal to noise ratio (SNR) values.

7. The device of claim 1, wherein the programmable element further correlates the respiratory volume and/or respiratory flow parameter with a predefined respiratory condition.

8. The device of claim 1, wherein the programmable element further determines an index of respiratory sufficiency which is used as a diagnostic or monitoring tool.

9. The device of claim 1, further comprising a patient controlled analgesia system coupled to the programmable element.

10. The device of claim 9, wherein the programmable element, based on the determined respiratory volume and/or respiratory flow parameter of the patient, at least one of determines the effect of one or more drugs or medical interventions on the patient, provides information supporting extubating the patient, suggests extubating the patient, provides information supporting adjusting the patient's therapies or medications, suggests adjusting the patient's therapies or medications, provides information supporting adjusting ventilator settings, suggests adjusting ventilator settings, provides information supporting adjusting weaning the patient off ventilation, suggests weaning the patient off ventilation, provides information to assesses a patients status before, during, or after surgery or medical procedure, monitors for air leaks, monitors for improper ventilation, monitors exercise, monitors stress levels, and monitors disease or medical condition.

11. The device of claim 1, further comprising an alarm that delivers an alert upon detection of inadequate contact with the patient.

12. The device of claim 1, further comprising two demodulators, wherein the first demodulator filters a signal with a generator signal as a carrier and the second demodulator filters the signal with 90-degree phase rotating circuitry before demodulation.

13. The device of claim 1, further comprising simultaneously measuring at least one of an electrocardiogram, an impedance cardiography and impedance pneumography.

14. The device of claim 1, further comprising at least one impedance measurement electrode implanted in the body.

15. The device of claim 1, wherein the impedance measurement electrodes comprise one or more measurement channels placed on the abdomen or thorax of the patient.

16. The device of claim 1, wherein the calibration coefficient is derived from one or more of the following patient specific measurements: total body impedance, bioelectrical impedance measurements, average or baseline impedance on the measurement channel, ECG signal acquired at various locations, anthropomorphic measurements.

17. The device of claim 1, further comprising adaptive electronics controlled by a microprocessor and different amplifiers, wherein the adaptive electronics maintain the gains on the different amplifiers to prevent the signal from going out of range.

18. The device of claim 17, wherein the microprocessor tracks and adjusts the set gains at each of the amplifiers.

19. The device of claim 1, wherein the programmable element controls, via a closed loop, at least one of a ventilator and an analgesia device.

20. The device of claim 1, wherein the at least one determined respiratory volume and/or respiratory flow parameter of the patient is combined with at least one of pulse oximetry or capnography.

21. The device of claim 1, wherein adjusting the acquisition circuitry for the signal variation comprises automatically changing parameters of the y-axis of a display chart of a dataset.

22. The device of claim 1, wherein adjusting the acquisition circuitry for the signal variation comprises automatically recalculating or adjusting the calibration coefficient when there is a change in at least one of baseline impedance, mean impedance, and respiratory rate.

23. The device of claim 1, wherein the volume and/or flow parameter is minute ventilation of the patient.

24. The device of claim 1, wherein anatomic locations of the at least one tetra polar configuration are: a first pair of electrodes located near a sternal notch of the patient and a second pair of electrodes placed in a region of the right mid-axillary line aligned with the xiphoid process.

25. The device of claim 1, wherein anatomic locations of the at least one tetra polar configuration are: at least one electrode placed on the patient's mid-clavicular line, at least one electrode placed on the patient's mid-axillary line, and at least one electrode placed on the patient's xiphoid process.

* * * * *